"(12) United States Patent
Townes et al.

US009175311B2

(10) Patent No.: US 9,175,311 B2
(45) Date of Patent: Nov. 3, 2015

(54) POLYCISTRONIC VECTOR FOR HUMAN INDUCED PLURIPOTENT STEM CELL PRODUCTION

(75) Inventors: Tim Townes, Birmingham, AL (US); Kevin M. Pawlik, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 13/480,753

(22) Filed: May 25, 2012

(65) Prior Publication Data

US 2013/0017596 A1 Jan. 17, 2013

Related U.S. Application Data

(62) Division of application No. 12/640,767, filed on Dec. 17, 2009, now abandoned.

(60) Provisional application No. 61/138,260, filed on Dec. 17, 2008.

(51) Int. Cl.
| | |
|---|---|
| *C12N 15/867* | (2006.01) |
| *C12N 15/861* | (2006.01) |
| *C12N 15/87* | (2006.01) |
| *C12N 15/79* | (2006.01) |
| *C12N 15/86* | (2006.01) |
| *C12N 5/074* | (2010.01) |

(52) U.S. Cl.
CPC .............. *C12N 15/86* (2013.01); *C12N 5/0696* (2013.01); *C12N 2501/602* (2013.01); *C12N 2501/603* (2013.01); *C12N 2501/604* (2013.01); *C12N 2510/00* (2013.01); *C12N 2740/15043* (2013.01); *C12N 2800/30* (2013.01)

(58) Field of Classification Search
CPC ........... A01K 67/0271; A01K 2207/12; A01K 2217/058; A01K 2217/15; A01K 2217/203; A01K 2217/206; A01K 2217/30; A01K 2227/10; A01K 2267/02; A01K 67/02; A01K 67/0275; A01K 2267/0331; A01K 48/00; A01K 38/00; C12N 5/0696; C12N 15/86; C12N 2510/00; C12N 2501/604; C12N 2800/30; C12N 2501/602; C12N 2501/603; C12N 2740/15043
USPC ................... 435/320.1; 536/23.1, 23.5, 23.53
See application file for complete search history.

(56) References Cited

U.S. PATENT DOCUMENTS

| | | |
|---|---|---|
| 2003/0219866 A1 | 11/2003 | Kruijer |
| 2006/0222636 A1 | 10/2006 | Rambukkana |
| 2008/0076176 A1 | 3/2008 | Dominko et al. |
| 2011/0151447 A1* | 6/2011 | Park et al. ..................... 435/6.1 |
| 2011/0236966 A1* | 9/2011 | Mostoslavsky et al. ....... 435/325 |
| 2012/0028821 A1* | 2/2012 | Jaenisch et al. .................. 506/9 |

FOREIGN PATENT DOCUMENTS

WO   WO2007/069666    6/2007

OTHER PUBLICATIONS

Zufferey et al (Journal of Virology, 1998, 72, 9873-9880.*
Hanna et al Science, 2007, 318, 1920-1923, online Dec. 6, 2007.*
Nakagawa et al (Nature Biotechnology, 2008, 26, 101-106.*
Hasegawa et al (Stem cells Jul. 2007;25(7)1707-12.*
Wu et al Blood. 2006;108:1183-1188.*
Lauth et al (Nucleic acid research, 2002, 30, 21, 1-7.*
Donnelly et al Journal of General Virology, 2001, 82, 1027-1041.*
Hoist et al (Nature Methods, 2006, 191-197.*
Szymczak et al (Nature Biotech, 2004, 589-594).*
NCBI accession Nos.NM__002701, pp. 1-5.*
NCBI accession Nos. SOX2: NM__003106, pp. 1-4.*
NCBI accession Nos. KLF4: NM__004235, 1-4.*
NCBI accession Nos. NM 002701, pp. 1-5 , May 4, 2014.*
NCBI accession Nos. SOX2: NM__003106, pp. 1-4 , May 5, 2014.*
NCBI accession Nos. KLF4: NM__004235, 1-4 , May 25, 2014.*
Wu et al., "Correction of sickle cell disease by homologous recombination in embryonic stem cells," Blood 108:1183-8 (2006).
Yamanaka, "Induction of pluripotent stem cells from mouse fibroblasts by four transcription factors," Cell Proliferation 41:51-6 (2008).
Yu et al., "Induced pluripotent stem cell lines derived from human somatic cells," Science 318:1917-20 (2007).
Yu et al., "Induced pluripotent stem cell lines derived from human somatic cells," Science 318:1917-20 (2007) Supporting Material.
Zufferey et al., "Self-inactivating lentivirus vector for safe and efficient in vivo gene delivery," J. Virol. 72:9873-80 (1998).
Abstract for NIH Grant No. 1R03HL096268-01, Awarded Dec. 9, 2008.
Aasen et al., "Efficient and rapid generation of induced pluripotent stem cells from human keratinocytes," Nat. Biotech. 26:1276-84 (2008).
Adhikary and Eilers, "Transcriptional regulation and transformation by Myc proteins," Nat. Rev. Mol. Cell. Bio. 6:635-45 (2005).
Aoi et al., "Generation of pluripotent stem cells from adult mouse liver and stomach cells," Science 321:699-702 (2008).
Avilion et al., "Multipotent cell lineages in early mouse development depend on SOX2 function," Gene Dev. 17:126-40 (2003).
Balzer and Moss, "Localization of the developmental timing regulator Lin28 to mRNP complexes, P-bodies and stress granules," RNA Biol. 4:16-25 (2007).
Brambrink et al., "Sequential expression of pluripotentcy markers during direct reprogramming of mouse somatic cells," Cell Stem Cell 2:151-9 (2008).
Carey et al., "Reprogramming of murine and human somatic cells using a single polycistronic vector," Proc. Natl. Acad. Sci. USA 106:157-162 (2009).

(Continued)

*Primary Examiner* — Anoop Singh
(74) *Attorney, Agent, or Firm* — Kilpatrick Townsend & Stockton LLP

(57) ABSTRACT

Methods of producing induced pluripotent stem (iPS) cells are provided. For example, a method of producing an iPS cell from a differentiated cell, which includes transforming the differentiated cell with a first vector comprising a nucleic acid sequence comprising a nucleic acid sequence encoding an Oct4, a nucleic acid sequence encoding a Sox2, and a nucleic acid sequence encoding a Klf4. Each of the nucleic acid sequences are separated from each other by a first and second viral 2A sequence. The method described can further comprise culturing the transformed cell under conditions that allow for the production of an iPS cell and isolating the cultured iPS cell.

15 Claims, 17 Drawing Sheets

(56) References Cited

OTHER PUBLICATIONS

Chang et al., "Polycistronic lentiviral vector for "hit and run" reprogramming of adult skin fibroblasts to induced pluripotent stem cells," Stem Cells 27:1042-9 (2009).

Chinnasamy et al., "Multicistronic lentiviral vectors containing the FMDV 2A cleavage factor demonstrate robust expression of encoded genes at limiting MOI," Virol. J. 3:14 (2006).

Dimos et al., "Induced pluripotent stem cells generated from patients with ALS can be differentiated into motor neurons," Science 321:1218-21 (2008).

Donnelly et al., "Analysis of the aphthovirus 2A/2B polyprotein 'cleavage' mechanism indicates not a proteolytic reaction, but a novel translational effect: a putative ribosomal 'skip,'" J. Gen. Virol. 82:1013-25 (2001).

Donnelly et al., "The 'cleavage' activities of foot-and-mouth disease virus 2A site-directed mutants and naturally occurring '2A-like' sequences," J. Gen. Virol. 82:1027-41 (2001).

Eminli et al., "Reprogramming of neural progenitor cells into induced pluripotent stem cells in the absence of exogenous Sox2 expression," Stem Cells 26:2467-74 (2008).

Felipe et al., "Use of the 2A sequence from foot-and-mouth disease virus in the generation of retroviral vectors for gene therapy," Gene Therapy 6:198-208 (1999).

Fernandez et al., "Genomic targets of the human c-Myc protein," Gene Dev. 17:1115-29 (2003).

Florin et al., "Cre recombinase-mediated gene targeting of mesenchymal cells," Genesis 38:139-44 (2004).

Hanna et al., "Treatment of sickle cell anemia mouse model with iPS cells generated from autologous skin," Science 318:1920-3 (2007).

Hanna et al., "Direct reprogramming of terminally differentiated mature B lymphocytes to pluripotentcy," Cell 133:250-64 (2008).

Holst et al., "Generation of T-cell receptor retrogenic mice," Nat. Protoc. 1:406-17 (2006).

Huangfu et al., "Induction of pluripotent stem cells from primary human fibroblasts with only Oct4 and Sox2," Nat. Biotechnol. 26:1269-75 (2008).

Kim et al., "Pluripotent stem cells induced from adult neural stem cells by reprogramming with two factors," Nature 454:646-50 (2008).

Levasseur et al., "Correction of a mouse model of sickle cell disease: lentiviral/antisickling-globin gene transduction of unmobilized, purified hematopoietic stem cells," Blood 102:4312-9 (2003).

Li et al., "Murine embryonic stem cell differentiation is promoted by SOCS-3 and inhibited by the zinc finger transcription factor Klf4," Blood 105:635-7 (2005).

Lowry et al., "Generation of human induced pluripotent stem cells from dermal fibroblasts," Proc. Natl. Acad. Sci. USA 105:2883-8 (2008).

Maherali et al., "Directly reprogrammed fibroblasts show global epigenetic remodeling and widespread tissue contribution," Cell Stem Cell 1:55-70 (2007).

Meissner et al., "Direct reprogramming of genetically unmodified fibroblasts into pluripotent stem cells," Nat. Biotech. 25:77-81 (2007).

Miyoshi et al., "Development of a self-inactivating lentivirus vector," J. Virol. 72:8150-7 (1998).

Mohamadnejad and Swenson, "Induced pluripotent cells mimicking human embryonic stem cells," Arch. Iranian Med. 11:125-8 (2008).

Nakagawa et al., "Generation of induced pluripotent stem cells without Myc from mouse and human fibroblasts," Nat. Biotech. 26:101-6 (2008).

Nichols et al., "Formation of pluripotent stem cells in the mammalian embryo eepends on the POU transcription factor Oct4," Cell 95:379-91 (1998).

Niwa et al., "Quantitative expression of Oct-3/4 defines differentiation, dedifferentiation or self-renewal of ES cells," Nat. Genet. 24:372-6 (2000).

Okita et al., "Generation of germline-competent induced pluripotent stem cells," Nature 448:313-7 (2007).

Okita et al., "Generation of mouse induced pluripotent stem cells without viral vectors," Science 322:949-53 (2008).

Okita et al., "Generation of mouse induced pluripotent stem cells without viral vectors," Science 322:949-53 (2008) Supporting Material.

Park et al., "Reprogramming of human somatic cells to pluripotentcy with defined factors," Nature 451:141-7 (2008).

Park et al., "Disease-specific induced pluripotent stem cells," Cell 134:1-10 (2008).

Park et al., "Generation of human-induced pluripotent stem cells," Nat. Protoc. 3:1180-6 (2008).

Qi and Pei, "The magic of four: induction of pluripotent stem cells from somatic cells by Oct4, Sox2, Myc and Klf4," Cell Research 17:578-80 (2007).

Rajasingh et al., "Cell-free embryonic stem cell extract-mediated derivation of multipotent stem cells from NIH3T3 fibroblasts for functional and anatomical ischemic tissue repair," Circ. Res. 102:e107-17 (2008).

Rossant, "The magic brew," Nature 448:260-2 (2007).

Sauer, "Inducible gene targeting in mice using the Cre/lox system," Methods 14:381-92 (1998).

Schnutgen et al., "A directional strategy for monitoring Cre-mediated recombination at the cellular level in the mouse," Nat. Biotech. 21:562-5 (2003).

Silva et al., "Promotion of reprogramming to ground state pluripotentcy with defined factors," PLoS Biol. 6:e253 (2008).

Somner et al., "Induced pluripotent stem cell generation using a single lentiviral stem cell cassette," Stem Cells 27:543-9 (2009).

Stadtfeld et al., "Defining molecular cornerstones during fibroblast to iPS cell reprogramming in mouse," Cell Stem Cell 2:230-40 (2008).

Stadtfeld et al., "Induced pluripotent stem cells generated without viral integration," Science 322:945-9 (2008).

Stadtfeld et al., "Reprogramming of pancreatic beta cells into induced pluripotent stem cells," Curr. Biol. 18:890-4 (2008).

Szymczak et al., "Correction of multi-gene deficiency in vivo using a single 'self-cleaving' 2A peptide-based retroviral vector," Nat. Biotech. 22:589-94 (2004).

Takahashi and Yamanaka, "Induction of pluripotent stem cells from mouse embryonic and adult fibroblast cultures by defined factors," Cell 126:663-76 (2006).

Takahashi et al., "Induction of pluripotent stem cells from adult human fibroblasts by defined factors," Cell 131:861-72 (2007).

Takahashi et al., "Induction of pluripotent stem cells from fibroblast cultures," Nat. Protoc. 2:3081-9 (2007).

Townes, "Gene replacement therapy for sickle cell disease and other blood disorders," Hematology 2008:193-6 (2008).

Varas et al., "Fibroblast derived induced pluripotent stem cells show no common retroviral vector insertion," Stem Cells 27:300-6 (2009).

Viswanathan et al., "Selective blockade of microRNA processing by Lin28," Science 320:97-100 (2008).

Wang et al., "Requirement of Nanog dimerization for stem cell self-renewal and pluripotency," Proc. Natl. Acad. Sci. USA 105:6326-31 (2008).

Wernig et al., "In vitro reprogramming of fibroblasts into a pluripotent ES-cell-like state," Nature 448:318-24 (2007).

Wernig et al., "c-Myc is dispensible for direct reprogramming of mouse fibroblasts," Cell Stem Cell 2:10-2 (2008).

Wernig et al., "Neurons derived reprogrammed fibroblasts functionally integrate into the fetal brain and improve symptoms of rats with Parkinson's disease," Proc. Natl. Acad. Sci. USA 105:5856-61 (2008).

* cited by examiner

2A Peptide
GSGATNFSLLKQAGDVEENPGP

```
Primer OCT4-F               OCT4
       NotI    SwaI          M  A  G  H  L  A  S  D  F  A  F
       CACACAGCGGCCGCATTTAAATCCACCatggcgggacacctggcttcggatttcgccttc
   1   ----------+---------+---------+---------+---------+---------+  60
       GTGTGTCGCCGGCGTAAATTTAGGACCtaccgccctgtggaccgaagcctaaagcggaag S  P  P  P  G  G  G  D  G  P  G  G  P  E  P  G  W  V  D
        tcgcccctccaggtggtggaggtgatgggccagggggccggagccgggctgggttgat
   61   ----------+---------+---------+---------+---------+---------+  120
        agcggggaggtccaccacctccactacccggtccccggcctcggcccgacccaacta P  R  T  W  L  S  F  Q  G  P  P  G  G  P  G  I  G  P  G  V
        cctcggacctggctaagcttccaaggccctcctggagggccaggaatcgggccggggtt
   121  ----------+---------+---------+---------+---------+---------+  180
        ggagcctggaccgattcgaaggttccgggaggacctcccggtccttagcccggccccaa G  P  G  S  E  V  W  G  I  P  P  C  P  P  P  Y  E  F  C  G
        gggccaggctctgaggtgtggggattcccccatgccccccgccgtatgagttctgtggg
   181  ----------+---------+---------+---------+---------+---------+  240
        cccggtccgagactccacaccccctaagggggtacggggggcggcatactcaagacacc G  M  A  Y  C  G  P  Q  V  G  V  G  L  V  P  Q  G  G  L  E
        gggatggcgtactgtgggcccaggttggagtggggctagtgccccaaggcggcttggag
   241  ----------+---------+---------+---------+---------+---------+  300
        ccctaccgcatgacacccggggtccaacctcaccccgatcacggggttccgccgaacctc T  S  Q  P  E  G  E  A  G  V  G  V  E  S  N  S  D  G  A  S
        acctctcagcctgagggcgaagcaggagtcggggtggagagcaactccgatggggcctcc
   301  ----------+---------+---------+---------+---------+---------+  360
        tggagagtcggactcccgcttcgtcctcagccccacctctcgttgaggctaccccggagg P  E  P  C  T  V  T  P  G  A  V  K  L  E  K  E  K  L  E  Q
        ccggagccctgcaccgtcacccctggtgccgtgaagctggagaaggagaagctggagcaa
   361  ----------+---------+---------+---------+---------+---------+  420
        ggcctcgggacgtggcagtgggggaccacggcacttcgacctcttcctcttcgacctcgtt N  P  E  E  S  Q  D  I  K  A  L  Q  K  E  L  E  Q  F  A  K
        aaccccggaggagtcccaggacatcaaagctctgcagaaagaactcgagcaatttgccaag
   421  ----------+---------+---------+---------+---------+---------+  480
        ttggggcctcctcaggtcctgtagtttcgagacgtctttcttgagctcgttaaacggttc L  L  K  Q  K  R  I  T  L  G  Y  T  Q  A  D  V  G  L  T  L
        ctcctgaagcagaagaggatcacccctgggatatacacaggccgatgtggggctcaccctg
   481  ----------+---------+---------+---------+---------+---------+  540
        gaggacttcgtcttctcctagtgggaccctatatgtgtccggctacaccccgagtgggac
```

FIG. 7A

```
                G  V  L  F  G  K  V  F  S  Q  T  T  I  C  R  F  E  A  L  Q
      ggggttctatttgggaaggtattcagccaaacgaccatctgccgctttgaggctctgcag
541   ---------+---------+---------+---------+---------+---------+ 600
      ccccaagataaaccCttccataagtcggtttgctggtagacggcgaaactccgagacgtc L  S  F  K  N  M  C  K  L  R  P  L  L  Q  K  W  V  E  E  A
      cttagcttcaagaacatgtgtaagctgcggcccttgctgcagaagtgggtggaggaagct
601   ---------+---------+---------+---------+---------+---------+ 660
      gaatcgaagttcttgtacacattcgacgccgggaacgacgtcttcacccacctccttcga D  N  N  E  N  L  Q  E  I  C  K  A  E  T  L  V  Q  A  R  K
      gacaacaatgaaaatcttcaggagatatgcaaagcagaaaccctcgtgcaggcccgaaag
661   ---------+---------+---------+---------+---------+---------+ 720
      ctgttgttactttTagaagtcctctatacgtttcgtctttgggagcacgtccgggctttc R  K  R  T  S  I  E  N  R  V  R  G  N  L  E  N  L  F  L  Q
      agaaagcgaaccagtatcgagaaccgagtgagaggcaacctggagaatttgttcctgcag
721   ---------+---------+---------+---------+---------+---------+ 780
      tcttTcgcttggtcatagctcttggctcactctccgttggacctcttaaacaaggacgtc C  P  K  P  T  L  Q  Q  I  S  H  I  A  Q  Q  L  G  L  E  K
      tgcccgaaacccacactgcagcagatcagccacatcgcccagcagcttggctctgagaag
781   ---------+---------+---------+---------+---------+---------+ 840
      acgggctttgggtgtgacgtcgtctagtcggtgtagcgggtcgtcgaacccgagctcttc D  V  V  R  V  W  F  C  N  R  R  Q  K  G  K  R  S  S  S  D
      gatgtggtccgagtgtggttctgtaaccggcgccagaagggcaagcgatcaagcagcgac
841   ---------+---------+---------+---------+---------+---------+ 900
      ctacaccaggctcacaccaagacattggccgcggtcttcccgttcgctagttcgtcgctg Y  A  Q  R  E  D  F  E  A  A  G  S  P  F  S  G  G  P  V  S
      tatgcacaacgagaggattttgaggctgctgggtctcctttctcaggggaccagtgtcc
901   ---------+---------+---------+---------+---------+---------+ 960
      atacgtgttgctctcctaaaactccgacgacccagaggaaagagtcccctggtcacagg F  P  L  A  P  G  P  H  F  G  T  P  G  Y  G  S  F  H  F  T
      tttcctctggccccagggccccattttggtacccaggctatgggagccctcacttcact
961   ---------+---------+---------+---------+---------+---------+ 1020
      aaggagaccggggtcccggggtaaaaccatgggtccgatacccTcgggagtgaagtga A  L  Y  S  S  V  P  F  P  E  G  E  A  F  P  P  V  S  V  T
      gcactgtactcctcggtccctttccctgaggggaagcctttcccccTgTcTccgtcacc
1021  ---------+---------+---------+---------+---------+---------+ 1080
      cgtgacatgaggagccagggaaagggactcccccTtcggaaaggggggacagaggcagtgg
```

FIG. 7B

```
                                    PTV1 2A peptide          Primer SOX2-F
         T  L  G  S  P  M  H  S  N  G  S  G  A  T  N  F  S  L  L  K
         actctgggctctcccatgcattcaaacGGATCCGGAGCCACGAACTTCTCTCTGTTAAAG
1081     ---------+---------+---------+---------+---------+---------+ 1140
         tgagacccgagagggtacgtaagtttgCCTAGGCCTCGGTGCTTGAAGAGAGACAATTTC
             Primer OCT4-R ↓  SOX2
         Q  A  G  D  V  E  E  N  P  G  ▼P  M  Y  N  M  M  E  T  E  L
         CAAGCAGGAGATGTTGAAGAAAACCCCGGGCCTatgtacaacatgatggagacggagctg
1141     ---------+---------+---------+---------+---------+---------+ 1200
         GTTCGTCCTCTACAACTTCTTTTGGGGCCCGGAtacatgttgtactacctctgcctcgac K  P  P  G  P  Q  Q  T  S  G  G  G  G  N  S  T  A  A  A
         aagccgccgggcccgcagcaaacttcggggggcggcggcggcaactccaccgcggcggcg
1201     ---------+---------+---------+---------+---------+---------+ 1260
         ttcggcggccgggcgtcgtttgaagccccccgccgccgccgttgaggtggcgccgccgc A  G  G  N  Q  K  N  S  P  D  R  V  K  R  P  M  N  A  F  M
         gccggcggcaaccagaaaaacagcccggaccgcgtcaagcggcccatgaatgccttcatg
1261     ---------+---------+---------+---------+---------+---------+ 1320
         cggccgccgttggtcttttgtcgggcctggcgcagttcgccgggtacttacggaagtac V  W  S  R  G  Q  R  R  K  M  A  Q  E  N  P  K  M  H  N  S
         gtgtggtcccgcgggcagcggcgcaagatggcccaggagaacccaagatgcacaactcg
1321     ---------+---------+---------+---------+---------+---------+ 1380
         cacaccagggcgcccgtcgccgcgttctaccgggtcctcttgggttctacgtgttgagc E  I  S  K  R  L  G  A  E  W  K  L  L  S  E  T  E  K  R  P
         gagatcagcaagcgcctgggcgccgagtggaaacttttgtcggagacggagaagcggccg
1381     ---------+---------+---------+---------+---------+---------+ 1440
         ctctagtcgttcgcggacccgcggctcaccttgaaaacagcctctgcctcttcgccggc F  I  D  E  A  K  R  L  R  A  L  H  M  K  E  H  P  D  Y  K
         ttcatcgacgaggctaagcggctgcgagcgctgcacatgaaggagcacccggattataaa
1441     ---------+---------+---------+---------+---------+---------+ 1500
         aagtagctgctccgattcgccgacgctcgcgacgtgtacttcctcgtgggcctaatattt Y  R  P  R  R  K  T  K  T  L  M  K  K  D  K  Y  T  L  P  G
         taccggccccggcggaaaaccaagacgctcatgaagaaggataagtacacgctgcccggc
1501     ---------+---------+---------+---------+---------+---------+ 1560
         atggccggggccgccttttggttctgcgagtacttcttcctattcatgtgcgacgggccg G  L  L  A  P  G  G  N  S  M  A  S  G  V  G  V  G  A  G  L
         gggctgctggccccggcgggcaatagcatggcgagcggggtcggggtgggcgccggcctg
1561     ---------+---------+---------+---------+---------+---------+ 1620
         cccgacgaccggggccgcccgttatcgtaccgctcgccccagccccaccgcggccggac
```

FIG. 7C

```
              G  A  G  V  N  Q  R  M  D  S  Y  A  H  M  N  G  W  S  N  G
              ggcgcggcgtgaaccagcgcatggacagttacgcgcacatgaacggctggagcaacggc
      1621    ---------+---------+---------+---------+---------+---------+ 1680
              ccgcgccgcacttggtcgcgtacctgtcaatgcgcgtgtacttgccgacctcgttgccg S  Y  S  M  M  Q  D  Q  L  G  Y  P  Q  H  P  G  L  N  A  H
              agctacagcatgatgcaggaccagctgggctacccgcagcacccgggcctcaatgcgcac
      1681    ---------+---------+---------+---------+---------+---------+ 1740
              tcgatgtcgtactacgtcctggtcgacccgatgggcgtcgtgggcccggagttacgcgtg G  A  A  Q  M  Q  P  M  H  R  Y  D  V  S  A  L  Q  Y  N  S
              ggcgcagcgcagatgcagcccatgcaccgctacgacgtgagcgccctgcagtacaactcc
      1741    ---------+---------+---------+---------+---------+---------+ 1800
              ccgcgtcgcgtctacgtcgggtacgtggcgatgctgcactcgcgggacgtcatgttgagg M  T  S  S  Q  T  Y  M  N  G  S  P  T  Y  S  M  S  Y  S  Q
              atgaccagctcgcagacctacatgaacggctcgcccacctacagcatgtcctactcgcag
      1801    ---------+---------+---------+---------+---------+---------+ 1860
              tactggtcgagcgtctggatgtacttgccgagcgggtggatgtcgtacaggatgagcgtc Q  G  T  P  G  M  A  L  G  S  M  G  S  V  V  K  S  E  A  S
              cagggcaccoctggcatggctcttggctccatgggttcggtggtcaagtccgaggccagc
      1861    ---------+---------+---------+---------+---------+---------+ 1920
              gtcccgtggggaccgtaccgagaaccgaggtacccaagccaccagttcaggctccggtcg S  S  P  P  V  V  T  S  S  S  H  S  R  A  P  C  Q  A  G  D
              tccagccccctgtggttacctcttcctcccactccagggcgccctgccaggccggggac
      1921    ---------+---------+---------+---------+---------+---------+ 1980
              aggtcggggggacaccaatggagaaggagggtgaggtcccgcgggacggtccggccoctg L  R  D  M  I  S  M  Y  L  P  G  A  E  V  P  E  P  A  A  P
              ctccgggacatgatcagcatgtatctccccggcgccgaggtgccggaacccgccgccccc
      1981    ---------+---------+---------+---------+---------+---------+ 2040
              gaggccctgtactagtcgtacatagaggggccgcggctccacggccttgggcggcggggg S  R  L  H  M  S  Q  H  Y  Q  S  G  P  V  P  G  T  A  I  N
              agcagacttcacatgtcccagcactaccagagcggcccggtgccggcacggccattaac
      2041    ---------+---------+---------+---------+---------+---------+ 2100
              tcgtctgaagtgtacagggtcgtgatggtctcgccgggccacggccgtgccggtaattg PTV1 2A peptide      Primer KLF4-F
              G  T  L  P  L  S  H  M  G  S  G  A  T  N  F  S  L  L  K  Q
              ggcacactgcccctctcacacatgGGATCCGGAGCCACGAACTTCTCTCTGTTAAAGCAA
      2101    ---------+---------+---------+---------+---------+---------+ 2160
              ccgtgtgacggggagagtgtgtacCCTAGGCCTCGGTGCTTGAAGAGAGACAATTTCGTT
              Primer SOX2-R
```

FIG. 7D

```
                               ↓     KLF4
      A  G  D  V  E  E  N  P  G  P  M  A  V  S  D  A  L  L  P  S
      GCAGGAGATGTTGAAGAAAACCCCGGGCCTatggctgtcagcgacgcgctgctcccatct
2161  ------------+----------+----------+----------+----------+----------+ 2220
      CGTCCTCTACAACTTCTTTTGGGGCCCGGAtaccgacagtcgctgcgcgacgagggtaga F  S  T  F  A  S  G  P  A  G  R  E  K  T  L  R  Q  A  G  A
      ttctccacgttcgcgtctggcccggcgggaagggagaagacactgcgtcaagcaggtgcc
2221  ------------+----------+----------+----------+----------+----------+ 2280
      aagaggtgcaagcgcagaccgggccgcccttccctcttctgtgacgcagttcgtccacgg P  N  N  R  W  R  E  E  L  S  H  M  K  R  L  P  P  V  L  P
      ccgaataaccgctggcgggaggagctctcccacatgaagcgacttccccagtgcttccc
2281  ------------+----------+----------+----------+----------+----------+ 2340
      ggcttattggcgaccgccctcctcgagagggtgtacttcgctgaaggggtcacgaaggg G  R  P  Y  D  L  A  A  A  T  V  A  T  D  L  E  S  G  G  A
      ggccgcccctatgacctggcggcggcgaccgtggccacagacctggagagcggcggagcc
2341  ------------+----------+----------+----------+----------+----------+ 2400
      ccggcggggatactggaccgccgccgctggcaccggtgtctggacctctcgccgcctcgg G  A  A  C  G  G  S  N  L  A  P  L  P  R  R  E  T  E  E  F
      ggtgcggcttgcggcggtagcaacctggcgcccctacctcggagagagaccgaggagttc
2401  ------------+----------+----------+----------+----------+----------+ 2460
      ccacgccgaacgccgccatcgttggaccgcggggatggagcctctctctggctcctcaag N  D  L  L  D  L  D  F  I  L  S  N  S  L  T  H  P  P  E  S
      aacgatctcctggacctggactttattctctccaattcgctgacccatcctccggagtca
2461  ------------+----------+----------+----------+----------+----------+ 2520
      ttgctagaggacctggacctgaaataagagaggttaagcgactgggtaggaggcctcagt V  A  A  T  V  S  S  S  A  S  A  S  S  S  S  P  S  S  S
      gtggccgccaccgtgtcctcgtcagcgtcagcctcctcttcgtcgtcgccgtcgagcagc
2521  ------------+----------+----------+----------+----------+----------+ 2580
      caccggcggtggcacaggagcagtcgcagtcggaggagaagcagcagcggcagctcgtcg G  P  A  S  A  P  S  T  C  S  F  T  Y  P  I  R  A  G  N  D
      ggccctgccagcgcgccctccacctgcagcttcacctatccgatccgggccgggaacgac
2581  ------------+----------+----------+----------+----------+----------+ 2640
      ccgggacggtcgcgcgggaggtggacgtcgaagtggataggctaggcccggcccttgctg P  G  V  A  P  G  G  T  G  G  G  L  L  Y  G  R  E  S  A  P
      ccggggcgtggcgccggcggcacgggcggaggcctcctctatggcagggagtccgctccc
2641  ------------+----------+----------+----------+----------+----------+ 2700
      ggccccgcaccgcggccgccgtgcccgcctccggaggagataccgtccctcaggcgaggg
```

FIG. 7E

```
            P  P  T  A  P  F  N  L  A  D  I  N  D  V  S  P  S  G  G  F
         cctccgacggctcccttcaacctggcggacatcaacgacgtgagccccteggggcggcttc
   2701  ---------+---------+---------+---------+---------+---------+ 2760
         ggaggctgccgagggaagttggaccgcctgtagttgctgcactcggggagcccgccgaag V  A  E  L  L  R  P  E  L  D  P  V  Y  I  P  P  Q  Q  P  Q
         gtggccgagctcctgcggccagaattggacccgtgtacattccgccgcagcagccgcag
   2761  ---------+---------+---------+---------+---------+---------+ 2820
         caccggctcgaggacgccggtcttaacctgggccacatgtaaggcggcgtcgtcggcgtc P  P  G  G  G  L  M  G  K  F  V  L  K  A  S  L  S  A  P  G
         ccgccaggtggcgggctgatgggcaagttcgtgctgaaggcgtcgctgagcgcccctggc
   2821  ---------+---------+---------+---------+---------+---------+ 2880
         ggcggtccaccgcccgactacccgttcaagcacgacttccgcagcgactcgcggggaccg S  E  Y  G  S  P  S  V  I  S  V  S  K  G  S  P  D  G  S  H
         agcgagtacggcagcccgtcggtcatcagcgtcagcaaaggcagccctgacggcagccac
   2881  ---------+---------+---------+---------+---------+---------+ 2940
         tcgctcatgccgtcgggcagccagtagtcgcagtcgtttccgtcgggactgccgtcggtg P  V  V  V  A  P  Y  N  G  G  P  P  R  T  C  P  K  I  K  Q
         ccggtggtggtggcgccctacaacggcgggccgccgcgcacgtgccccaagatcaagcag
   2941  ---------+---------+---------+---------+---------+---------+ 3000
         ggccaccaccaccgcgggatgttgccgcccggcggcgcgtgcacggggttctagttcgtc E  A  V  S  S  C  T  H  L  G  A  G  P  P  L  S  N  G  H  R
         gaggcggtctcttcgtgcacccacttgggcgctggacccccctctcagcaatggccaccgg
   3001  ---------+---------+---------+---------+---------+---------+ 3060
         ctccgccagagaagcacgtgggtgaacccgcgacctgggggagagtcgttaccggtggcc P  A  A  H  D  F  P  L  G  R  Q  L  P  S  R  T  T  P  T  L
         ccggctgcacacgacttccccctggggcggcagctccccagcaggactacccgacccctg
   3061  ---------+---------+---------+---------+---------+---------+ 3120
         ggccgacgtgtgctgaaggggggaccccgccgtcgagggggtcgtcctgatgggctgggac G  L  E  E  V  L  S  S  R  D  C  H  P  A  L  P  L  P  P  G
         ggtcttgaggaagtgctgagcagcagggactgtcaccctgccctgccgcttcctccggc
   3121  ---------+---------+---------+---------+---------+---------+ 3180
         ccagaactccttcacgactcgtcgtccctgacagtgggacgggacggcgaaggagggccg F  H  P  H  P  G  P  N  Y  P  S  F  L  P  D  Q  M  Q  P  Q
         ttccatccccaccggggcccaattaccatccttcctgcccgatcagatgcagccgcaa
   3181  ---------+---------+---------+---------+---------+---------+ 3240
         aaggtaggggtgggcccggggttaatggtaggaaggacgggctagtctacgtcggcgtt
```

FIG. 7F

```
            V  P  P  L  H  Y  Q  E  L  M  P  P  G  S  C  M  P  E  E  P
         gtcccgccgctccattaccaagagctcatgccacccggttcctgcatgccagaggagccc
  3241   ---------+---------+---------+---------+---------+---------+ 3300
         cagggcggcgaggtaatggttctcgagtacggtgggccaaggacgtacggtctcctcggg K  P  K  R  G  R  R  S  W  P  R  K  R  T  A  T  H  T  C  D
         aagccaaagaggggaagacgatcgtggccccggaaaaggaccgccacccacacttgtgat
  3301   ---------+---------+---------+---------+---------+---------+ 3360
         ttcggtttctcccctttctgctagcaccggggccttttcctggcggtgggtgtgaacacta Y  A  G  C  G  K  T  Y  T  K  S  S  H  L  K  A  H  L  R  T
         tacgcgggctgcggcaaaacctacacaaagagttcccatctcaaggcacacctgcgaacc
  3361   ---------+---------+---------+---------+---------+---------+ 3420
         atgcgcccgacgccgttttggatgtgtttctcaagggtagagttccgtgtggacgcttgg H  T  G  E  K  P  Y  H  C  D  W  D  G  C  G  W  K  F  A  R
         cacacaggtgagaaaccttaccactgtgactgggacggctgtggatggaaattcgcccgc
  3421   ---------+---------+---------+---------+---------+---------+ 3480
         gtgtgtccactctttggaatggtgacactgaccctgccgacacctacctttaagcgggcg S  D  E  L  T  R  H  Y  R  K  H  T  G  H  R  P  F  Q  C  Q
         tcagatgaactgaccaggcactaccgtaaacacacggggcaccgcccgttccagtgccaa
  3481   ---------+---------+---------+---------+---------+---------+ 3540
         agtctacttgactggtccgtgatggcatttgtgtgcccgtggcgggcaaggtcacggtt K  C  D  R  A  F  S  R  S  D  H  L  A  L  H  M  K  R  H  F
         aaatgcgaccgagcatttccaggtcggaccacctcgccttacacatgaagaggcatttt
  3541   ---------+---------+---------+---------+---------+---------+ 3600
         tttacgctggctcgtaaaaggtccagcctggtggagcggaatgtgtacttctccgtaaaa
                                                 Primer KLF4-R
          *  SwaI    SalI
         taaATTTAAATGTCGACTGTGTG
  3601   ---------+---------+---- 3623
         attTAAATTTACAGCTGACACAC
```

FIG. 7G

POLYCISTRONIC VECTOR FOR HUMAN INDUCED PLURIPOTENT STEM CELL PRODUCTION

CROSS-REFERENCE TO RELATED APPLICATIONS

This application is a divisional of U.S. application Ser. No. 12/640,767, filed Dec. 17, 2009, now abandoned which claims the benefit of U.S. Provisional Application No. 61/138,260, filed on Dec. 17, 2008.

STATEMENT REGARDING FEDERALLY FUNDED RESEARCH

This invention was made with government support under Grant No. RO1-HL057619 from the National Institutes of Health. The United States government has certain rights in this invention.

BACKGROUND

Embryonic stem (ES) cells have the ability to grow indefinitely while maintaining pluripotency and the ability to differentiate into a multitude of different cell types. Because of these two qualities, human ES cell therapies have been proposed for regenerative medicine and tissue replacement after injury or disease. However, there are ethical difficulties regarding the use of human embryos for the isolation of human ES cells as well as problems with tissue rejection following transplantation of foreign ES cells in patients.

SUMMARY

Methods of producing induced pluripotent stem (iPS) cells are provided. For example, methods of producing an iPS cell from a differentiated cell are provided. The methods include the step of transforming the differentiated cell with a first vector comprising a nucleic acid sequence comprising a nucleic acid sequence encoding an Oct4, a nucleic acid sequence encoding a Sox2, and a nucleic acid sequence encoding a Klf4. Each of the nucleic acid sequences are separated by a first and second nucleic acid sequence encoding a viral 2A sequence.

Also provided are methods of producing an iPS cell, wherein the vector used to produce the cell is deleted from the genome of the iPS cell. For example, the methods include the step of transforming the differentiated cell with a first vector comprising a nucleic acid sequence comprising a nucleic acid sequence encoding an Oct4, a nucleic acid sequence encoding a Sox2, and a nucleic acid sequence encoding a Klf4. Each of the nucleic acid sequences are separated by a first and second nucleic acid sequence encoding a viral 2A sequence. The vector further comprises a loxP sequence. The methods further include the step of transforming the iPS cell with a second vector. The second vector comprises a nucleic acid sequence encoding a Cre recombinase. Expression of the Cre recombinase results in the deletion of the first retroviral vector from the genome of the cells.

Also provided are vectors comprising a nucleic acid sequence encoding an Oct4, a nucleic acid sequence encoding a Sox2, and a nucleic acid sequence encoding a Klf4, and cells comprising the vector. Each of the nucleic acid sequences are separated from each other by a first and second nucleic acid sequence encoding a viral 2A sequence.

Also provided are kits comprising a first vector and a second vector. The first vector comprises a nucleic acid sequence encoding an Oct4, a nucleic acid sequence encoding a Sox2, and a nucleic acid sequence encoding a Klf4. Each of the nucleic acid sequences are separated from each other by a first and second viral 2A sequence. The second vector comprises a nucleic acid sequence encoding a Cre recombinase.

Further provided are methods of treating or preventing a disease associated with a genetic mutation in a subject. The methods comprise selecting a subject with a disease associated with a genetic mutation; isolating differentiated cells from the subject; transforming the differentiated cells with a vector comprising an unmutated nucleic acid sequence of interest; culturing the transformed cells under conditions that allow for the production of a population of iPS cells; screening the iPS cells for correction of the genetic mutation; and administering the iPS cells to the subject, wherein administration of the iPS cells treats or prevents the disease associated with the genetic mutation in the subject. The vector comprises a nucleic acid sequence comprising (i) an unmutated nucleic acid sequence of interest and homologous nucleic acid sequences flanking the genetic mutation, (ii) a nucleic acid sequence encoding a Cre recombinase operably linked to an inducible promoter, (iii) a first and second loxP sequence, (iv) a nucleic acid sequence encoding an Oct4, (v) a nucleic acid sequence encoding a Sox2, and (vi) a nucleic acid sequence encoding a Klf4. Each of the nucleic acid sequences, (iv)-(vi), are separated by a first and second nucleic acid sequence encoding a viral 2A sequence.

DESCRIPTION OF DRAWINGS

FIG. 1 shows the Oct4, Sox2, Klf4 (OSK) lentiviral vector for reprogramming adult skin fibroblasts to iPS cells.

FIG. 2 shows images of iPS cell colonies.

FIG. 3 shows RT-PCR analysis and Bisulfite sequence analysis of isolated iPS cells.

FIG. 4 shows a vector map and Southern blot hybridization of iPS-1 cellular DNA.

FIG. 5 shows teratomas and chimeras derived from iPS cells.

FIG. 6 shows a vector map and Southern blot hybridization of iPS-1 and iPS-2 cellular DNA after OSK vector deletion.

FIGS. 7A-G show the nucleotide (SEQ ID NO:7 for top strand and SEQ ID NO:8 for bottom strand) and amino acid (SEQ ID NO:9) sequences of the polycistron encoded by the vector. Underlined and labeled are primers used to create the polycistron. The Oct4, Sox2, Klf4 and PTV1 2A sequences are denoted.

DETAILED DESCRIPTION

Figures 1A, 1B:
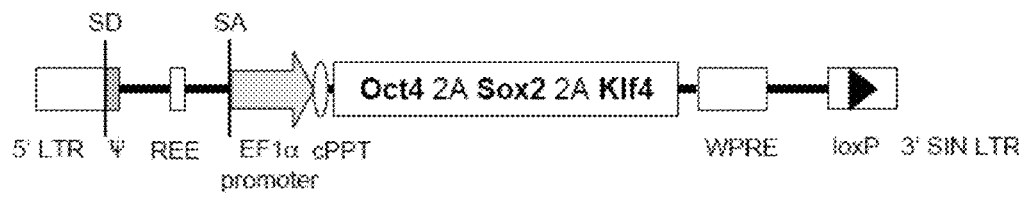
FIG. 1A shows a diagram of the vector.
FIG. 1B shows the amino acid sequence of the 2A polypeptide with a 3-amino acid GSG linker (SEQ ID NO:1)

A number of studies have been published detailing the production of induced pluripotent stem (iPS) cells from differentiated, embryonic and adult, mammalian cells (Takahashi and Yamanaka, Cell 1126:663-76 (2006); Meissner et al., Nat. Biotech. 25(10):1177-81 (2007); Takahashi et al., Cell 131:861-72 (2007); and Park et al., Nature 451:141-7 (2008)). In each of these publications, four transcription factors, Oct-3/4, Sox2, Klf4, and c-Myc, were introduced to the differentiated cells through retroviral transduction to produce iPS cells from differentiated somatic cells. Alternatively, it was found that another combination of factors, which include Oct-3/4, Sox2, Nanog, and Lin28, were capable of reprogramming somatic cells to iPS cells that exhibit the essential characteristics of embryonic stem (ES) cells (Yu et al., Science 18:1917-20 (2007)).

Oct4 and Sox2 are core transcription factors that function in the maintenance of pluripotentcy in early embryos and embryonic stem (ES) cells (Nichols et al., Cell 95:379-391 (1998); Niwa et al., Nat. Genet. 24:372-6 (2000); and Avilion et al., Gene Dev. 17:126-40 (2003)). Klf4 has been shown to contribute to the long-term maintenance of the ES cell phenotype and the rapid proliferation of ES cells in culture (Li et al., Blood 105:635-7 (2005)). Nanog is a transcription factor that is important in early development and stem cell pluripotentcy as it activates ES cell critical factors and represses differentiation-promoting genes (Wang et al., Proc. Natl. Acad. Sci. USA 105:6326-31 (2008)). Lin28 is a marker of undifferentiated human embryonic stem cells and has been shown to bind mRNAs in the cytoplasm as well as block the production of mature let-7 microRNA in mouse embryonic stem cells (Balzer and Moss, RNA Biology 4:16-25 (2007); Viswanathan et al., Science 320:97-100 (2008)). The c-Myc protein is also a transcription factor, as well as a tumor-related factor, and has many targets that enhance proliferation and transformation (Adhikary and Eilers, Nat. Rev. Mol. Cell. Bio. 6:635-45 (2005)) with many of these downstream targets potentially having roles in the generation of iPS cells. Additionally, c-Myc may globally induce histone acetylation (Fernandez et al., Genes Dev. 17:1115-29 (2003)), to allow other transcription factors to bind to their specific target loci. In the case of iPS cell production, expression of c-Myc would result in histone acetylation, thus allowing Oct3/4 and Sox2 to target the genes necessary to create a stem cell-like cell.

The use of retroviruses to incorporate Oct3/4, Sox2, Klf4, and c-Myc into the cells is both advantageous and deleterious. The advantages of using a retrovirus is that the virus integrates into the genome of the cell and thus is genetically transferred to the progeny when the cell undergoes cell division. This allows for the continued expression of these factors as differentiated cells undergo the transition to an iPS cell. In spite of these advantages, Takahashi et al. found that each iPS clone contained three to six retroviral integrations for each factor, creating the possibility of more than 20 retroviral integration sites per iPS clone, which increases the risk of tumorigenesis (Takahashi et al., Cell 131:861-72 (2007)). In fact, approximately 20% of mice derived from iPS cells developed tumors. This was attributable, at least in part, to the reactivation of the c-Myc retrovirus (Okita et al., Nature 448:313-7 (2007)).

The methods and compositions provided herein are designed to produce iPS cells that reduce the risk of insertional mutagenesis by allowing for the removal or deletion of vectors once the iPS cells have been generated or by using vectors that do not integrate into the cellular genome.

As used herein, the term induced pluripotent stem (iPS) cell encompasses any cell that has been reprogrammed to phenotypically resemble a pluripotent stem cell. An iPS cell is derived from a non-pluripotent cell but is capable of reproducing itself. An iPS cell is also capable of terminal differentiation into a cell-type normally found in the relevant system, tissue, or organ. An iPS cell is similar to an ES cell in morphology, proliferation, and pluripotentcy. For example, an iPS cell and an ES cell express the same markers. Examples of these markers include Oct3/4, Nanog, E-Ras, Cripto, Dax1, Fgf4, stage-specific embryonic antigen 1 (SSEA1), SSEA3, SSEA4, alkaline phosphatase, tumor-related antigen (TRA)-1-60, TRA-1-81, and Zfp296.

Provided herein are vectors for producing iPS cells. Thus, provided herein is a first vector comprising a nucleic acid sequence encoding an Oct4, a nucleic acid sequence encoding a Sox2, and a nucleic acid sequence encoding a Klf4. Each of the nucleic acid sequences are separated by a first and second nucleic acid sequence encoding a viral 2A sequence. The first nucleic acid sequence encoding a viral 2A sequence is the same as or different from the second nucleic acid sequence encoding a viral 2A sequence. Optionally, the first vector comprises SEQ ID NO:7. Optionally, the first vector comprises a nucleic acid sequence encoding SEQ ID NO:9.

Optionally, the first vector comprises SEQ ID NO:43. The vector comprising SEQ ID NO:43 was deposited with the American Type Culture Collection, 10801 University Boulevard, Manassas, Va. 20110-2209 in accordance with the Budapest Treaty on Oct. 6, 2009, and has accession number PTA-10385.

Optionally, Oct4, Sox2, and Klf4 are human. Optionally, Oct4, Sox2, and Klf4 are non-human (e.g., rodent, canine, or feline). There are a variety of sequences that are disclosed on Genbank, at www.pubmed.gov and these sequences and others are herein incorporated by reference in their entireties as are individual subsequences or fragments contained therein. As used herein, Oct4 refers to the Oct4 transcription factor and homologs, variants, and isoforms thereof. For example, the nucleotide and amino acid sequences of human Oct4 can be found at GenBank Accession Nos. BC117435 and AAI17436.1, respectively. Optionally, the nucleotide and amino acid sequences of human Oct4 isoform 1 can be found at GenBank Accession Nos. NM_002701.4 and NP_002692.2, respectively. The nucleotide and amino acid sequences for human Oct4 isoform 2 can be found at GenBank Accession Nos. NM_203289.3 and NP_976034.3, respectively. As used herein, Sox2 refers to the Sox2 transcription factor and homologs, variants, and isoforms thereof. The nucleotide and amino acid sequences of human Sox2 can be found at GenBank Accession Nos. BC013923 and AAH13923.1, respectively. Optionally, the nucleotide and amino acid sequences of human Sox2 can be found at GenBank Accession Nos. NM_003106.2 and NP_003097.1, respectively. As used herein, Klf4 refers to the Klf4 transcription factor and homologs, variants, and isoforms thereof. The nucleotide and amino acid sequences of human Klf4 can be found at GenBank Accession Nos. BC029923 and AAH29923.1, respectively. Optionally, the nucleotide and amino acid sequences of human Klf4 can be found at GenBank Accession Nos. NM_004235.4 and NP_004226.3, respectively. Thus provided are the nucleotide sequences of Oct4, Sox2, and Klf4 comprising a nucleotide sequence at least about 70%, 75%, 80%, 85%, 90%, 95%, 98%, 99% or more identical to the nucleotide sequence of the aforementioned GenBank Accession Numbers. Also provided are amino acid sequences of Oct4, Sox2, and Klf4 comprising an amino acid sequence at least about 70%, 75%, 80%, 85%, 90%, 95%, 98%, 99% or more identical to the sequences of the aforementioned GenBank Accession Numbers.

Nucleic acids that encode the polypeptide sequences, variants, and fragments thereof are disclosed. These sequences include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequences.

As used herein, the term peptide, polypeptide or protein is used to mean a molecule comprised of two or more amino acids linked by a peptide bond. Protein, peptide, and polypeptide are also used herein interchangeably to refer to amino acid sequences. It should be recognized that the term polypeptide or protein is not used herein to suggest a particular size or number of amino acids comprising the molecule and that a polypeptide of the disclosure can contain up to several amino acid residues or more.

As with all peptides, polypeptides, and proteins, including fragments thereof, it is understood that additional modifications in the amino acid sequence of the variant Oct4, Sox2, and Klf4 polypeptides can occur that do not alter the nature or function of the peptides, polypeptides, or proteins. Such modifications include conservative amino acids substitutions and are discussed in greater detail below.

The polypeptides provided herein have a desired function. Oct4 and Sox2 are core transcription factors that regulate the expression of a defined set of target genes to maintain the pluripotentcy associated with ES cells. Klf4 is a transcription factor that regulates the expression of a defined set of target genes to maintain the long-term ES cell phenotype as well as to drive the proliferation of ES cells. The polypeptides are tested for their desired activity using the in vitro assays described herein.

The polypeptides described herein can be further modified and varied so long as the desired function is maintained. It is understood that one way to define any known modifications and derivatives or those that might arise, of the disclosed genes and proteins herein is through defining the modifications and derivatives in terms of identity to specific known sequences. Specifically disclosed are polypeptides which have at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to Oct4, Sox2, and Klf4 and variants provided herein. Those of skill in the art readily understand how to determine the identity of two polypeptides. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman, Adv. Appl. Math 2:482 (1981), by the identity alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-10 (1989); Jaeger et al., Methods Enzymol. 183: 281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and to be disclosed herein.

Protein modifications include amino acid sequence modifications. Modifications in amino acid sequence may arise naturally as allelic variations (e.g., due to genetic polymorphism), may arise due to environmental influence (e.g., by exposure to ultraviolet light), or may be produced by human intervention (e.g., by mutagenesis of cloned DNA sequences), such as induced point, deletion, insertion, and substitution mutants. These modifications can result in changes in the amino acid sequence, provide silent mutations, modify a restriction site, or provide other specific mutations. Amino acid sequence modifications typically fall into one or more of three classes: substitutional, insertional, or deletional modifications. Insertions include amino and/or terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at lease one residue has been removed and a different residues inserted in its place. Such substitutions generally are made in accordance with the following Table 1 and are referred to as conservative substitutions.

TABLE 1

Amino Acid Substitutions

| Amino Acid | Substitutions (others are known in the art) |
|---|---|
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Modifications, including the specific amino acid substitutions, are made by known methods. By way of example, modifications are made by site specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

Optionally, the vector comprises its various components in any order. Examples include from the 5' end, a nucleic acid sequence encoding a first polypeptide, the first nucleic acid encoding a viral 2A sequence, a nucleic acid encoding a second polypeptide, the second nucleic acid sequence encoding a viral 2A sequence, and a nucleic acid sequence encoding a third polypeptide. The first nucleic acid sequence encoding a viral 2A sequence is the same as or different from the second nucleic acid sequence encoding a viral 2A sequence. The first, second, and third polypeptides are selected from the group consisting of Oct4, Sox2, and Klf4, and the first, second, and third polypeptides are different from each other. Thus, for example, the first polypeptide is Oct4, the second polypeptide is Sox2, and the third polypeptide is Klf4. By way of another example, the first polypeptide is Sox2, the second polypeptide is Oct4, and the third polypeptide is Klf4.

The vector comprises in order from the 5' end, a nucleic acid sequence encoding an Oct4, a first nucleic acid sequence encoding a viral 2A sequence, a nucleic acid sequence encoding a Sox2, a second nucleic acid sequence encoding a viral 2A sequence, and a nucleic acid sequence encoding a Klf4. Optionally, the vector comprises in order from the 5' end, a nucleic acid sequence encoding an Oct4, a first nucleic acid sequence encoding a viral 2A sequence, a nucleic acid sequence encoding a Klf4, a second nucleic acid sequence encoding a viral 2A sequence, and a nucleic acid sequence encoding a Sox2. Optionally, the vector comprises in order from the 5' end, a nucleic acid sequence encoding a Sox2, a first nucleic acid sequence encoding a viral 2A sequence, a nucleic acid sequence encoding an Oct4, a second nucleic acid sequence encoding a viral 2A sequence, and a nucleic acid sequence encoding a Klf4. Optionally, the vector comprises in order from the 5' end, a nucleic acid sequence encoding a Sox2, a first nucleic acid sequence encoding a viral 2A sequence, a nucleic acid sequence encoding a Klf4, a second nucleic acid sequence encoding a viral 2A sequence, and a nucleic acid sequence encoding an Oct4. Optionally, the vector comprises in order from the 5' end, a nucleic acid sequence encoding a Klf4, a first nucleic acid sequence encoding a viral 2A sequence, a nucleic acid sequence encoding an Oct4, a second nucleic acid sequence encoding a viral 2A sequence, and a nucleic acid sequence encoding a Sox2. Optionally, the vector comprises in order from the 5' end, a nucleic acid sequence encoding a Klf4, a first nucleic acid sequence encoding a viral 2A sequence, a nucleic acid sequence encoding a Sox2, a second nucleic acid sequence encoding a viral 2A sequence, and a nucleic acid sequence encoding an Oct4.

A common strategy of positive-strand RNA viruses is to encode some, or all, of their proteins in the form of a polyprotein translated from one RNA molecule. Viruses have adapted multiple methods to allow for the production of individual protein molecules from a polyprotein. In the case of picornaviruses, all of the proteins are encoded in a single open reading frame. The picornaviral polyproteins undergo a cleavage event between the major domains of the viral genome, which are separated by viral 2A sequences. Viral 2A sequences allow for the translation of multiple polypeptides in a multicistronic RNA molecule by stimulating peptide cleavage between the polypeptides without disengaging the ribosome. The use of viral 2A sequences to produce multiple proteins from a multicistronic message is known, see, e.g., Donnelly et al., J. Gen. Virol. 82:1013-25 (2001); Donnelly et al., J. Gen. Virol. 82:1027-41 (2001); Chinnasamy et al., Virol. J. 3:14 (2006); Holst et al., Nat. Protoc. 1(1):406-17 (2006); and Szymczak et al., Nat. Biotechnol. 22(5):589-94 (2004).

Optionally, the first and second nucleic acid sequences encoding a viral 2A sequence is a picornaviral, a tetraviral 2A sequence, or a combination thereof. Optionally, the picornaviral 2A sequences are selected from the group consisting of the Enteroviral 2A sequences, Rhinoviral 2A sequences, Cardioviral 2A sequences, Aphthoviral 2A sequences, Hepatoviral 2A sequences, Erboviral 2A sequences, Kobuviral 2A sequences, Teschoviral 2A sequences, and the Parechoviral 2A sequences. Optionally, the tetraviral 2A sequences are selected from Betatetraviral 2A seqeuneces or Omegatetraviral 2A sequences. Optionally, the first and second nucleic acid sequences encoding a viral 2A sequence are picornaviral 2A sequences. Optionally, the first and second nucleic acid sequence encoding a viral 2A sequence is a Teschoviral 2A sequence. Optionally, the first nucleic acid sequence encoding a viral 2A sequence is a Cardioviral 2A sequence, and the second nucleic acid sequence encoding a viral 2A sequence is a Hepatoviral 2A sequence. Optionally, the first and second nucleic acid sequences encoding a viral 2A sequence are tetraviridae 2A sequences. Optionally, the first and second nucleic acid sequences encoding a viral 2A sequence is a Betatetraviral 2A sequence. Optionally, the first nucleic acid sequence encoding a viral 2A sequence is a Betatetraviral 2A sequence, and the second nucleic acid sequence encoding a viral 2A sequence is an Omegatetraviral 2A sequence. Optionally, the first nucleic acid sequence encoding a viral 2A sequence is a picornaviral 2A sequence, and the second nucleic acid sequence encoding a viral 2A sequence is a tetraviridae 2A sequence. Optionally, the first nucleic acid sequence encoding a viral 2A sequence is a Teschoviral 2A sequence, and the second nucleic acid sequence encoding a viral 2A sequence is a Betatetraviral 2A sequence. Optionally, the first nucleic acid sequence encoding a viral 2A sequence is a tetraviridae 2A sequence, and the second nucleic acid sequence encoding a viral 2A sequence is a picornaviral 2A sequence. Optionally, the first nucleic acid sequence encoding a viral 2A sequence is a Betatetraviral 2A sequence, and the second nucleic acid sequence encoding a viral 2A sequence is a Teschoviral 2A sequence. Optionally, the first and second nucleic acid sequences encoding a viral 2A sequence comprise a nucleic acid sequence encoding the amino acid sequence ATNFSLLKQAGDVEENPGP (SEQ ID NO:2). Optionally, the first and second nucleic acid sequences encoding a viral 2A sequence comprise a nucleic acid sequence encoding the amino acid sequence EGRGSLLTCGDVEENPGP (SEQ ID NO:3). Optionally the first nucleic acid sequence encoding a viral 2A sequence comprises a nucleic acid sequence encoding the amino acid sequence ATNFSLLKQAGDVEENPGP (SEQ ID NO:2), and the second nucleic acid sequence encoding a viral 2A sequence comprises a nucleic acid sequence encoding the amino acid sequence EGRGSLLTCGDVEENPGP (SEQ ID NO:3).

Optionally the first and second nucleic acid sequences encoding a viral 2A sequence comprises a nucleic acid sequence encoding an amino acid linker. The amino acid linker can be 1 to 10 amino acids in length. The amino acid linker can be 1 to 5 amino acids in length. The amino acid linker can be 1 to 3 amino acids in length. The amino acid linker is preferably 3 amino acids in length. The amino acid linker is, for example, GSG (SEQ ID NO:4). Optionally the first and second nucleic acid sequences encoding a viral 2A sequence with an amino acid linker comprise a nucleic acid sequence encoding the amino acid sequence GSGATNFSLLKQAGDVEENPGP (SEQ ID NO:1). Optionally the first and second nucleic acid sequences encoding a viral 2A sequence with an amino acid linker comprise a nucleic acid sequence encoding the amino acid sequence GSGEGRGSLLTCGDVEENPGP (SEQ ID NO:5).

The provided vector, for example, can be a retroviral vector. Retroviral vectors are able to integrate efficiently into the genomic DNA of cells. Integration into the genomic DNA allows for the continuous expression of the transgene and additionally allows for the transmission of the transgene to progeny cells when the cells divide. Another advantage of retroviral vectors is that they have the ability of being able to transduce a wide range of cell types from different animal species. Examples of retroviral vectors are known. See, e.g., Coffin et al., Retorviruses, Cold Spring Harbor Laboratory Press, Cold Spring Harbor, N.Y. (1997).

Optionally, the retroviral vector is a lentiviral vector. Lentiviral vectors are capable of infecting non-dividing cells. Optionally, the lentiviral vector is a lentiviral self-inactivating (SIN) vector. Lentiviral SIN vectors overcome the risk of activating cellular oncogenes when they are randomly integrated into the host genome. The lentiviral SIN vector is generated by deleting viral enhancer and promoter sequences within the vector, so that integration into the genome does not result in the activation of cellular oncogenes driven by the viral promoter and enhancer sequences. Methods of making and using the lentiviral SIN vectors are known. See, e.g., Miyoshi et al., J. Virol. 72(10):8150-7 (1998) and Zufferey et al., J. Virol. 72(12):9873-80 (1998).

Optionally, the retroviral vector contains a loxP sequence (e.g., ATAACTTCGTATAATGTATGCTATACGAAGTTAT (SEQ ID NO:6)). The loxP nucleic acid sequence is generally a 34 base pair nucleic acid sequence derived from Bacteriophage P1 that is used in combination with Cre recombinase to allow for site specific recombination. When a nucleic acid sequence contains a loxP sequence, the location of the loxP sequence is referred to as a loxP site. Usually, a nucleic acid sequence contains two loxP sites. The loxP sites are located on either side of a nucleic acid sequence to be removed from, for example, the genome of a cell. Expression of Cre recombinase in the cell promotes a recombination event that results in the deletion of the genomic DNA that is present in between the loxP sites. Specifically, the Cre recombinase binds and catalyzes the cleavage and strand exchange of DNA at two loxP sites, excising the nucleic acid between the loxP sites, and leaving a single loxP site in the genome. Examples of the Cre/lox system are known. See, e.g., Sauer, Methods 14(4): 381-92 (1998); Florin et al., Genesis 38(3):139-44; and Schnutgen et al., Nat. Biotechnol. 21(5):562-5 (2003).

Optionally, the loxP sequence is located in the 3' long terminal repeat of the vector. Retroviral integration into the genome of a cell occurs in a three part process. First the retroviral RNA is reverse transcribed by a virally encoded RNA reverse transcriptase to form a RNA-DNA hybrid helix. The reverse transcriptase uses the newly synthesized DNA as a template to synthesize the complementary DNA, while degrading the RNA template. The resulting DNA duplex is integrated into the genome of the cell with the loxP sequence in the 3' long terminal repeat of the retroviral vector copied into the 5' long terminal repeat during reverse transcription and then integrated into the genome. This provides a loxP sequence at either end of the integrated lentiviral vector; therefore, making it possible to remove the integrated retroviral vector by expression of Cre recombinase. Optionally, provided is a second vector comprising a nucleic acid encoding a Cre recombinase. Expression of the Cre recombinase results in the deletion of the first vector from the genome of the iPS cells.

Optionally, the vector is designed to correct a genetic mutation associated with a disease and to produce induced pluripotent stem (iPS) cells. The vector comprises a nucleic acid sequence comprising (i) a nucleic acid sequence encoding an Oct4, (ii) a nucleic acid sequence encoding a Sox2, and (iii) a nucleic acid sequence encoding a Klf4. Each of the nucleic acid sequences, (i)-(iii), are separated by a first and second nucleic acid sequence encoding a viral 2A sequence. The first nucleic acid sequence encoding a viral 2A sequence is the same as or different from the second nucleic acid sequence encoding a viral 2A sequence. The vector further comprises an unmutated nucleic acid sequence of interest and homologous nucleic acid sequences flanking the genetic mutation. An unmutated nucleic acid sequence of interest is a nucleic acid sequence lacking the genetic mutation associated with the disease. Optionally, the unmutated nucleic acid sequence of interest comprises the nucleic acid sequence encoding β-globin. Optionally, the vector further comprises a first and second loxP sequence. Optionally, the vector further comprises a nucleic acid sequence encoding a Cre recombinase operably linked to an inducible promoter. The inducible promoter, for example, can comprise a Nanog-responsive thymidine kinase promoter. Optionally, the vector can comprise a selectable marker. Optionally, the vector comprises SEQ ID NO:44.

Optionally, the nucleic acid comprising a nucleic acid sequence encoding an Oct4, a nucleic acid sequence encoding a Sox2, and a nucleic acid sequence encoding a Klf4, wherein the nucleic acid sequences are separated by a first and second nucleic acid sequence encoding a viral 2A sequence is administered by another type of vector comprising the nucleic acid. The vector based delivery is largely broken down into two classes: viral based delivery systems and non-viral based delivery systems. Such methods are known in the art and are readily adaptable for use with the methods described herein.

Provided herein are viral based expression vectors comprising the disclosed nucleic acid. Viral based delivery systems can, for example, include Adenoviral vectors, Adeno-associated viral vectors, Herpes viral vectors, Vaccinia viral vectors, Polio viral vectors, Sindbis viral vectors, and any other RNA viral vectors. Also useful are any viral families that share the properties of these listed viruses and vectors that make them suitable for use as vectors. The construction of replication-defective adenoviruses has been described (Berkner et al., J. Virology 61:1213-20 (1987); Massie et al., Mol. Cell. Biol. 6:2872-83 (1986); Haj-Ahmad et al., J. Virology 57:267-74 (1986); Davidson et al., J. Virology 61:1226-39 (1987); Zhang et al., BioTechniques 15:868-72 (1993)). The viral vectors are limited in the extent to which they can spread to other cell types, since they can replicate within an initial infected cell but are unable to form new infectious viral particles. Recombinant adenoviruses have been shown to achieve high efficiency after direct, in vivo delivery to airway epithelium, hepatocytes, vascular endothelium, CNS parenchyma and a number of other tissue sites. Other useful systems include, for example, replicating and host-restricted non-replicating vaccinia virus vectors.

Provided herein are also non-viral based expression vectors comprising the disclosed nucleic acids. Suitable vector backbones include, for example, plasmids, artificial chromosomes, BACs, YACs, or PACs. Numerous vectors and expression systems are commercially available from such corporations as Novagen (Madison, Wis.), Clonetech (Palo Alto, Calif.), Stratagene (La Jolla, Calif.), and Invitrogen/Life Technologies (Carlsbad, Calif.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

Any of the vectors provided herein can have a promoter sequence that drives the expression of the nucleic acid sequence comprising a nucleic acid sequence encoding a an Oct4, a nucleic acid sequence encoding a Sox2, and a nucleic acid sequence encoding a Klf4. Each of the nucleic acid sequences are separated from each other by a first and second viral 2A sequence. The first viral 2A sequence is the same as or different from the second viral 2A sequence. Preferred promoters controlling transcription from vectors in mammalian host cells may be obtained from various sources, for example, the genomes of viruses such as polyoma, Simian Virus 40 (SV40), adenovirus, retroviruses, hepatitis B virus and most preferably cytomegalovirus, or from heterologous mammalian promoters, e.g. beta actin promoter or EF1 promoter, or from hybrid or chimeric promoters (e.g., cytomegalovirus promoter fused to the beta actin promoter). The early and late promoters of the SV40 virus are conveniently obtained as an SV40 restriction fragment which also contains the SV40 viral origin of replication. The immediate early promoter of the human cytomegalovirus is conveniently obtained as a HindIII E restriction fragment. Of course, promoters from the host cell or related species also are useful herein.

The promoter can be an inducible promoter (e.g. chemically or physically regulated promoter). A chemically regulated promoter can, for example, be regulated by the presence of alcohol, tetracycline, a steroid, or a metal. A physically regulated promoter can, for example, be regulated by environmental factors, such as temperature and light. The promoter can be a cell type specific promoter (e.g. neuronal-specific, renal-specific, cardio-specific, liver-specific, or muscle-specific). A cell-type specific promoter is only expressed in the cell-type in which it is intended to be expressed. The promoter can be a promoter that is expressed independent of cell type. Examples of promoters that can be expressed independent of cell type include the cytomegalovirus (CMV) promoter, the Raus sarcoma virus (RSV) promoter, the adenoviral E1A promoter, and the EF-1α promoter. The promoter is preferably the EF-1α promoter.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs in length, and they function in cis. Enhancers usually function to increase transcription from nearby promoters. Enhancers can also contain response elements that mediate the regulation of transcription. While many enhancer sequences are now known from mammalian genes (globin, elastase, albumin, fetoprotein and insulin), typically one will use an enhancer from a eukaryotic cell virus for general expression. Preferred examples are the SV40 enhancer on the late side of the replication origin, the cytomegalovirus early promoter enhancer, the polyoma enhancer on the late side of the replication origin, and adenovirus enhancers.

The vectors also can include, for example, origins of replication, scaffold attachment regions (SARs), and/or markers. A marker gene can confer a selectable phenotype, e.g., antibiotic resistance, on a cell. This marker product is used to determine if the gene has been delivered to the cell and once delivered is being expressed. Examples of marker genes include the E. coli lacZ gene, which encodes β galactosidase, green fluorescent protein (GFP), and luciferase. Examples of suitable selectable markers for mammalian cells are dihydrofolate reductase (DHFR), thymidine kinase, neomycin, neomycin analog G418, hygromycin, blasticidin, and puromycin. When such selectable markers are successfully transferred into a mammalian host cell, the transformed mammalian host cell can survive if placed under selective pressure. In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or FLAG™ tag (Kodak, New Haven, Conn.) sequences typically are expressed as a fusion with the encoded polypeptide. Such tags can be inserted anywhere within the polypeptide, including at either the carboxyl or amino terminus.

Provided herein are methods for the production of iPS cells from differentiated cells. The methods include transforming the differentiated cell with a first vector comprising a nucleic acid sequence comprising a nucleic acid sequence encoding an Oct4, a nucleic acid sequence encoding a Sox2, and a nucleic acid sequence encoding a Klf4. Each of the nucleic acid sequences are separated by a first and second nucleic acid sequence encoding a viral 2A sequence. The first nucleic acid sequence encoding a viral 2A sequence can be the same as or different from the second nucleic acid sequence encoding a viral 2A sequence. Optionally, the method further includes transforming the differentiated cell with a second vector comprising a nucleic acid sequence encoding a c-Myc. Optionally, the first vector comprises a nucleic acid sequence comprising a nucleic acid sequence encoding an Oct4, a nucleic acid sequence encoding a Sox2, a nucleic acid sequence encoding a Klf4, and a nucleic acid sequence encoding a c-Myc. Each of the nucleic acid sequences are separated by a first, second, and third nucleic acid sequence encoding a viral 2A sequence. The first nucleic acid sequence encoding a viral 2A sequence can be the same as or different from the second nucleic acid sequence encoding a viral 2A sequence. The second nucleic acid sequence encoding a viral 2A sequence can be the same as or different from the third nucleic acid sequence encoding a viral 2A sequence. Optionally, the first vector comprises a nucleic acid sequence comprising a nucleic acid sequence encoding an Oct4, a nucleic acid sequence encoding a Sox2, and a nucleic acid sequence encoding a Nanog, wherein the nucleic acid sequences are each separated by a first and second nucleic acid sequence encoding a viral 2A sequence. The first nucleic acid sequence encoding a viral 2A sequence can be the same as or different from the second nucleic acid encoding a viral 2A sequence. The method further includes transforming the differentiated cell with a second vector comprising a nucleic acid sequence encoding a Lin28. Optionally, the first vector comprises a nucleic acid sequence comprising a nucleic acid sequence encoding an Oct4, a nucleic acid sequence encoding a Sox2, a nucleic acid sequence encoding a Nanog, and a nucleic acid sequence encoding a Lin28. Each of the nucleic acid sequences are separated by a first, second, and third nucleic acid sequence encoding a viral 2A sequence. The first nucleic acid sequence encoding a viral 2A sequence can be the same as or different from the second nucleic acid sequence encoding a viral 2A sequence. The second nucleic acid sequence encoding a viral 2A sequence can be the same as or different from the third nucleic acid sequence encoding a viral 2A sequence.

As used herein, the term transforming is used broadly to define a method of inserting a vector into a target cell. This can be accomplished, for example, by transfecting the vector into a target cell. Transfecting a vector into a target cell can be accomplished through the use of carriers, which can be divided into three primary classes: (cationic) polymers, liposomes, and nanoparticles. Examples of cationic polymers are DEAE-dextran and polyethylenimine, which bind the negatively charged vector and allows for the vector to be taken up by the cell through endocytosis. Liposomes are small, membrane-bounded bodies that fuse with the cell membrane and allow for the release of the vector into the cell. Nanoparticles are coupled to the vector and are shot directly into the nucleus of a cell using a gene gun. Transfections can further be divided into two categories: stable and transient transfections. Stable transfections result in the vector being permanently introduced into the cell and can be accomplished through the use of selectable marker, e.g., antibiotic resistance, as discussed herein. Transient transfections result in the vector being introduced temporarily to the cell. Alternatively, if the vector is a viral vector, it can be transfected into a host cell to produce virus, and the virus can be harvested and used to transduce the vector into the target cell. Transfection and transduction protocols are known. See, e.g., Sambrook et al., Molecular Cloning: A Laboratory Manual, $3^{rd}$ Ed., Cold Spring Harbor Press, Cold Spring Harbor, N.Y. (2001); Ausubel et al. (eds.), Current Protocols in Molecular Biology, John Wiley & Sons, Hoboken, N.J. (2004).

The differentiated cell can, for example, be obtained from a subject. The differentiated cell can be obtained and cultured from the subject by a variety of methods known and described, e.g., in Schantz and Ng, A Manual for Primary Human Cell Culture, World Scientific, Hackensack, N.J. (2004); and Human Cell Culture Protocols $2^{nd}$ Edition, (Ed. Picot, J), Humana Press, Totowa, N.J. (2004).

Optionally, the differentiated cell is a mammalian cell. The mammalian cell is optionally a human cell. Mammalian cells suitable for use in the claimed methods, include, but are not limited to epithelial cells, keratinocytes, fibroblasts, hepatocytes, neurons, osteoblasts, myocytes, kidney cells, lung cells, thyroid cells, and pancreatic cells.

Optionally, the methods further comprise culturing the transformed cell under conditions that allow for the isolation of an iPS cell or a population of iPS cells. For example, transformed cells (e.g., transformed keratinocytes) can be cultured under conditions with relatively high calcium levels. Specifically, prior to transfection, the differentiated cells are cultured under conditions with low calcium levels in the range of 0.01 mM to 0.1 mM. After transformation, the transformed cells are cultured under conditions with high calcium levels in the range of 1.0 mM to 2.0 mM. The high calcium levels promote the death of any untransformed differentiated cells but allow the survival of transformed cells that have undergone the transition to generate iPS cells. Alternatively, the transformed cells can be cultured under conditions that allow for the production of iPS cells through selection based on drug resistance. For example, the transformed vector contains a gene that will provide the transformed cells drug resistance (e.g., blasticidin, zeomycin, hygromycin, or neomycin resistance). Culturing untransformed cells in media supplemented with the selected drug promotes cell death. Culturing the transformed cells in media supplemented with the selected drug allows for the production of iPS cells.

Also provided are methods of producing iPS cells from differentiated cells comprising transforming the differentiated cells with a first retroviral vector comprising a loxP site in the 3' long terminal repeat of the vector and a nucleic acid sequence comprising a nucleic acid sequence encoding an Oct4, a nucleic acid sequence encoding a Sox2, and a nucleic acid sequence encoding a Klf4 (or any of the nucleic acid sequences described above). The nucleic acid sequences are separated from each other by a first and second nucleic acid sequence encoding a viral 2A sequence. The first nucleic acid sequence encoding a viral 2A sequence can be the same as or different from the second nucleic acid sequence encoding a viral 2A sequence. The method further comprises culturing the transformed cells under conditions that allow for the production of an iPS cell. The method can further comprise transforming the iPS cell with a second vector comprising a nucleic acid sequence encoding a Cre recombinase. Expression of the Cre recombinase results in the deletion of the first vector from the genome of the iPS cell, with the exception of a SIN LTR containing a loxP sequence. Deletion of the first vector from the genome of the iPS cell avoids or reduces the risk of insertional mutagenesis caused by the insertion of the vector into the genome. The method can further comprise isolating a population of the iPS cells lacking the first vector. The iPS cells isolated by this method are physically different from iPS cells produced by other methods, as these iPS cells lack the genomically integrated retroviral vector used to create the iPS cell.

Also provided are methods of correcting a genetic mutation of a differentiated cell prior to producing an iPS cell from the differentiated cell. The methods comprise transforming a differentiated cell with a vector comprising a nucleic acid sequence comprising (i) a nucleic acid sequence encoding an Oct4, (ii) a nucleic acid sequence encoding a Sox2, and (iii) a nucleic acid sequence encoding a Klf4, wherein each of the nucleic acid sequences, (i)-(iii), are separated by a first and second nucleic acid sequence encoding a viral 2A sequence. The vector further comprises a nucleic acid sequence comprising an unmutated nucleic acid sequence of interest and homologous nucleic acid sequences flanking the genetic mutation. Optionally, the vector further comprises a first and second loxP sequence. Optionally, the vector further comprises a nucleic acid sequence encoding a Cre recombinase operably linked to an inducible promoter. The inducible promoter can, for example, comprise a Nanog-responsive thymidine kinase promoter. Optionally, the vector comprises SEQ ID NO:44.

Optionally, the genetic mutation is a mutation in the nucleic acid sequence encoding β-globin, the nucleic acid sequence encoding cystic fibrosis transmembrane conductance regulator, the nucleic acid sequence encoding phenylalanine hydroxylase, and/or the nucleic acid sequence encoding dystrophin.

Optionally, the genetic mutation is a mutation in the nucleic acid sequence encoding β-globin. The mutation in the nucleic acid sequence encoding β-globin can, for example, result in a glutamic acid to valine substitution at the sixth amino acid of the β-globin protein. The glutamic acid to valine substitution can, for example, be caused by an A to T transversion at base pair +20 relative to the A(+1) of the ATG start codon of the nucleic acid sequence encoding β-globin. β-globin is used throughout as an example.

Further provided are iPS cells produced by these methods. iPS cells produced by these methods can, for example, be identified based on morphological characteristics of the cell (e.g., cell shape, cell composition, cellular organelle shape, and cell size). An iPS cell produced by these methods can be identified based on the expression of ES cell markers. ES cell markers can, for example, include Oct3/4, Nanog, E-Ras, Cripto, Dax1, Sox2, Fgf4, stage-specific embryonic antigen 1 (SSEA1), SSEA3, SSEA4, alkaline phosphatase, tumor-related antigen (TRA)-1-60, TRA-1-81, and Zfp296. Optionally, an iPS cell produced by these methods can be identified by comparing CpG methylation patterns in gene promoters of nontransformed, transformed, and ES cells. Optionally, an iPS cell produced by these methods can be identified based on the ability to form a teratoma comprised of cells derived from the endoderm, mesoderm, and ectoderm in an immunocompromised mouse. An iPS cell can be identified by a combination of cell morphological characteristics, expression of ES cell markers, CpG methylation patterns, and the ability to form a teratoma in an immunocompromised mouse.

Examples of analytical techniques useful in determining the expression of ES cell markers include reverse transcription-polymerase chain reaction (RT-PCR), quantitative real-time-PCR (qRT-PCR), one step PCR, RNase protection assay, primer extension assay, microarray analysis, gene chip, in situ hybridization, immunohistochemistry, Northern blot, Western blot, enzyme-linked immunosrbent assay (ELISA), enzyme immunoassay (EIA), radioimmunoassay (RIA), or protein array. These techniques are known. See, e.g., Sambrook et al., Molecular Cloning: A Laboratory Manual, 3$^{rd}$ Ed., Cold Spring Harbor Press, Cold Spring Harbor, N.Y. (2001).

Further provided are kits consisting of any of the first vectors described and a second vector comprising a nucleic acid sequence encoding a Cre recombinase. Optionally, the first vector comprises a nucleic acid sequence comprising a nucleic acid sequence encoding an Oct4, a nucleic acid encoding a Sox2, and a nucleic acid sequence encoding a Klf4. Each of the nucleic acid sequences are separated by a first and second viral 2A sequence. The first viral 2A sequence is the same as or different from the second viral 2A sequence. Optionally, directions to produce an iPS cell from a differentiated cell, a culture plate for producing the iPS cells, and/or containers for the vector or vectors are included in the kit.

Also provided herein, are methods of treating or preventing a disease or disorder in a subject at risk of developing a disease or disorder. The methods comprise isolating differentiated cells from the subject and transforming the differentiated cells with a first vector comprising a nucleic acid comprising a nucleic acid sequence encoding an Oct4, a nucleic acid sequence encoding a Sox2, and a nucleic acid sequence encoding a Klf4. Each of the nucleic acid sequences are separated by a first and second nucleic acid sequence encoding a viral 2A sequence. The first nucleic acid sequence encoding a viral 2A sequence can be the same as or different from the second nucleic acid sequence encoding a viral 2A sequence. The vector may further comprise a nucleic acid sequence comprising a therapeutic agent. Alternatively, the transformed cells may be transformed with a second vector comprising a nucleic acid sequence comprising a therapeutic agent. The method further comprises isolating a population of the iPS cells. The method further comprises administering to the subject the isolated population of iPS cells that are expressing the therapeutic agent.

The therapeutic agent can be an RNA molecule, a protein, or a DNA molecule. An RNA molecule can, for example, comprise an antisense RNA molecule, a ribozyme, a small interfering RNA (siRNA) that mediates RNA interference (RNAi), or a microRNA (miRNA) that mediates miRNA-induced translational repression. In the event the therapeutic agent is a protein, the protein can be a receptor, a signaling molecule, a transcription factor, a factor that promotes or inhibits apoptosis, a DNA replication factor, an enzyme, a structural protein, a neural protein, a heat shock protein, or a histone. In the event that the therapeutic agent is a DNA molecule, the DNA molecule can correct a defective or mutated DNA sequence within the genome of the subject. Ordinary skill in the art determines which therapeutic agents are expressed to treat a subject with or at risk of developing a disease or disorder.

Also provided are methods of treating or preventing a disease associated with a genetic mutation in a subject. The methods comprise selecting a subject with a disease associated with the genetic mutation; isolating differentiated cells from the subject; transforming the differentiated cells with a vector comprising an unmutated nucleic acid sequence of interest; culturing the transformed cells under conditions that allow for the production of a population of iPS cells; screening the iPS cells for correction of the genetic mutation; and administering an effective amount of the iPS cells to the subject. Administration of the iPS cells treats or prevents the disease associated with the genetic mutation in the subject. The vector comprising the unmutated nucleic acid sequence of interest is capable of correcting the genetic mutation associated with the disease and is capable of inducing pluripotent stem (iPS) cells. Optionally, the vector comprises a nucleic acid sequence comprising (i) an unmutated nucleic acid sequence of interest and homologous nucleic acid sequences flanking the genetic mutation, (ii) a nucleic acid sequence encoding a Cre recombinase operably linked to an inducible promoter, (iii) a first and second loxP sequence, (iv) a nucleic acid sequence encoding an Oct4, (v) a nucleic acid sequence encoding a Sox2, and (vi) a nucleic acid sequence encoding a Klf4. Each of the nucleic acid sequences, (iv)-(vi), are separated by a first and second nucleic acid sequence encoding a viral 2A sequence. The first nucleic acid sequence encoding a viral 2A sequence can be the same as or different from the second nucleic acid sequence encoding a viral 2A sequence. Optionally, the inducible promoter comprises a Nanog-responsive thymidine kinase promoter. Optionally, the vector comprises SEQ ID NO:44.

Examples of analytical techniques useful in screening an iPS cell for correction of the genetic mutation include any DNA-based sequencing assay, reverse transcription-polymerase chain reaction (RT-PCR), quantitative real-time-PCR (qRT-PCR), RNase protection assay, Southern blot, Northern blot, and restriction length polymorphism (RFLP) analysis. These techniques are known. See, e.g., Sambrook et al., Molecular Cloning: A Laboratory Manual, 3rd Ed., Cold Spring Harbor Press, Cold Spring Harbor, N.Y. (2001).

Optionally, administration of the isolated iPS cells to the subject can be done after the isolated iPS cells have been differentiated to specific types of stem cells (e.g., hematopoietic stem cells). Administration of the differentiated iPS cells to the subject can be done systemically (e.g., injection of iPS cells into the circulatory system) or it can be localized to an organ or tissue (e.g., injection of iPS cells or delivery of stem cells, optionally, on or in a scaffold/matrix to specified organ or tissue). Thus, the administered iPS cells are designed so they interact with the tissue or organ or with target cells. The method of administration is determined by one of skill in the art to be consistent with the treatment of the disease or disorder that the subject has or is at risk of developing.

Optionally, the differentiated cell is selected from the group consisting of a(n) epithelial cell, keratinocyte, fibroblast, hepatocyte, neuron, osteoblast, myocyte, kidney cell, lung cell, thyroid cell, and pancreatic cell. Optionally, the differentiated cell is a keratinocyte.

The disease associated with a genetic mutation can, for example, be selected from the group consisting of sickle cell disease, thalassemia, cystic fibrosis, phenylketonuria, and Duchenne muscular dystrophy. The genetic mutation can be corrected via targeted gene replacement and the disease is amenable to a gene/cell therapy approach.

As used herein, a subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The term does not denote a particular age or sex. Thus, adult and newborn subjects, as well as fetuses, whether male or female, are intended to be covered. As used herein, patient or subject may be used interchangeably and can refer to a subject with or at risk of developing a disease or disorder. The term patient or subject includes human and veterinary subjects.

A subject at risk of developing a disease or disorder can be genetically predisposed to the disease or condition, e.g., have a mutation in a gene that causes the disease or disorder or have a family history of the disease or disorder. Additionally, a subject at risk of developing a disease or disorder may have symptoms or signs of early onset for the disease or condition. A subject with a disease or disorder has one or more symptoms of the disease or disorder or has been diagnosed with the disease or disorder.

According to the methods taught herein, the subject is administered an effective amount of the therapeutic agent and/or iPS cells. The terms effective amount and effective dosage are used interchangeably. The term effective amount is defined as any amount necessary to produce a desired physiologic response. Effective amounts and schedules for administering the therapeutic agent and/or iPS cells may be determined empirically, and making such determination is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one or skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

As used herein the terms treatment, treat, or treating refer to a method of reducing the effects of a disease or condition or one or more symptoms of the disease or condition. Thus in the disclosed method, treatment can refer to a 10%, 20%, 30%, 40%, 50%, 60%, 70%, 80%, 90%, or 100% reduction in the severity of an established disease or condition or one or more symptoms of the disease or condition. For example, a method for treating a disease is considered to be a treatment if there is a 10% reduction in one or more symptoms of the disease in a treated subject as compared to a control. A control can refer to an untreated subject. Alternatively, a control can comprise samples from the subject prior to treatment (i.e., the levels of one or more symptoms of the disease in the subject are determined prior to treatment and compared to the levels of one or more symptoms of the disease in the subject after treatment). Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of a therapeutic agent, that occurs before or at about the same time a subject begins to show one or more symptoms of the disease or disorder, wherein the administration inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods of using the disclosed compositions. Thus, if there are a variety of additional steps that can be performed it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

The examples below are intended to further illustrate certain aspects of the methods and compositions described herein, and are not intended to limit the scope of the claims.

EXAMPLES

General Methods
Production of OSK Polycistronic Lentiviral Vectors

The complete nucleotide sequence of pKP332 (the OSK polycistronic lentiviral vector) is given by SEQ ID NO:43. The pKP332 vector was deposited with the American Type Culture Collection, 10801 University Boulevard, Manassas, Va. 20110-2209 in accordance with the Budapest Treaty on Oct. 6, 2009, and has accession number PTA-10385. The complete nucleotide and amino acid map of the polycistron encoded by the vector used is given by SEQ ID NO:7 (top strand) and SEQ ID NO:9, respectively (FIG. 7). Construction of the polycistron using PTV1 2A sequences and fusion PCR was performed essentially as described (Holst et al., Nature Protocols 1:406-17 (2006)). Briefly, human Oct4 cDNA (Open Biosystems Clone 40125986) (Open Biosystems; Huntsville, Ala.) was PCR amplified and modified with primers OCT4-F: cacacagcggccgcatttaaatccaccatggcgggacacctggcttc (SEQ ID NO:10) and OCT4-R: agaggacgaacgaaattgtctctcttcaagcaccgaggcaaacttacgtaccctctcgg (SEQ ID NO:11) to contain Not I and Swa I restriction sites at the 5' end and a Kozak consensus sequence. At the 3' end, the Oct4 stop codon was eliminated and replaced with nucleotides (nt) from PTV1 2A that will form a 22-nt overlap with the 5' end of the Sox2 amplicon. Human Sox2 cDNA (Open Biosystems Clone 2823424) (Open Biosystems; Huntsville, Ala.) was PCR amplified and modified with primers SOX2-F: ctctgttaaagcaagcaggagatgt-tgaagaaaacccgggcctatgtacaacatgatggagacgg (SEQ ID NO:12) and SOX2-R: agaggacgaacgaaattgtctctct-tcaagcaccgaggcctagggtacacactctccccgtcac (SEQ ID NO:13) to overlap with the 3' end of the Oct4 amplicon and to append 2A nt sequences upstream of the Sox2 ATG. At the 3' end, the Sox2 stop codon was eliminated and replaced with nt from PTV1 2A that will form a 22-nt overlap with the 5' end of the Klf4 amplicon. Human Klf4 cDNA (Open Biosystems Clone 5111134) (Open Biosystems; Huntsville, Ala.) was PCR amplified and modified with primers KLF4-F: ctctgttaaag-caagcaggagatgttgaagaaaacccgggcctatggctgtcagcgacgcgc (SEQ ID NO:14) and KLF4-R: gtgtgtcagctgtaaatttaaatttt-tacggagaagtacacatt (SEQ ID NO:15) to overlap with the 3' end of the Sox2 amplicon and to append 2A nt sequences upstream of the Klf4 ATG. At the 3' end, the Klf4 stop codon was retained and Swa I and Sal I restriction sites were added. After PCR, the individual amplicons were gel purified and used in a three-element fusion PCR at a 1:100:1 (Oct4:Sox2:Klf4) molar ratio along with primers OCT4-F (SEQ ID NO:10) and KLF4-R (SEQ ID NO:15) to produce a 3623 base pair (bp) amplicon containing the polycistron. The polycistron was gel purified and cloned into the general cloning vector pKP114 using the NotI and SalI restriction sites to produce pKP330 and sequenced for authenticity. Subsequently, the polycistron was removed from pKP330 as a Swa I (Roche; Indianapolis, Ind.) fragment and subcloned into a Swa I site downstream of the EF1α promoter in the lentiviral vector pDL 171 (Levasseur et al., Blood 102:4312-9 (2003)) to produce the OSK polycistronic lentiviral vector pKP332, which was sequenced for authenticity.

By the same strategy, a second polycistronic lentival vector, pKP333, was produced that substitutes the PTV1 2A peptide between Sox2 and Klf4 with the *Thosea asigna* virus 18 amino acid 2A-like sequence and a GSG linker (underlined): <u>GSG</u>EGRGSLLT CGDVEENPGP (SEQ ID NO:5).

The complete nucleotide sequence of pKP360 (the OSK polycistronic lentiviral vector designed to correct β-globin mutation) is given by SEQ ID NO:44. To create this vector, a 6938 base pair (bp) loxP-SalI-NBS-TK-Cre/GFP-EF1α-OCT4-2A-SOX2-2A-KLF4-AscI-loxP DNA fragment is inserted into the second intron of the human β-globin gene contained within a bacterial artificial chromosome (BAC) by recombineering in DY380 *E. coli* cells. In a second recombineering step, a capture vector containing an MC1-driven herpes simplex virus thymidine kinase (HSV tk) gene is used to extract a 16,890 bp sequence from the BAC. The captured sequence consists of 5602 bp of human β-globin 5' homology, the 6938 bp insert sequence, and 4350 bp of human β-globin 3' homology. The first and second β-globin exons are contained within the 5' homology and the third exon is contained within the 3' homology. pKP360 contains a unique NotI restriction site at nucleotide #21049 for vector linearization prior to transfection. The HSV tk gene is used as a negative selection marker for random integration of the vector. Briefly, following transfection with pKP360 of differentiated cells isolated from a sickle cell disease (SCD) patient, 3 classes of cells results: (1) cells that do not receive the vector; these cells remain differentiated and eventually die in culture due to a limited replicative life span; (2) cells that integrate the vector in a non-targeted location; these cells could become iPS cells but will be selected against by gancyclovir because they contain the HSV tk gene; and (3) cells that integrate the vector by homologous recombination into the β-globin locus; these cells have lost the HSV tk marker and will therefore survive gancyclovir selection to become iPS cells with a corrected β-globin gene.

PCR reactions were performed using PrimeStar polymerase (Takara Bio Inc.; Otsu, Shiga, Japan). All of the oligos used in this study were synthesized by Integrated DNA Technologies (IDT; Coralville, Iowa) and all DNA gel extractions were performed using QIAquick Gel Extraction Kits (Qiagen; Valencia, Calif.).

Cell Culture and Viral Infections

Embryonic stem (ES) and induced pluripotent stem (iPS) cells were cultured on irradiated murine embryonic fibroblasts (MEFs) in ES cell media consisting of DMEM supplemented with 1× non-essential amino acids, 1× penicillin-streptomycin, 1× L-glutamine (Mediatech; Manassas, Va.), 1× nucleosides (Chemicon; Temecula, Calif.), 15% Fetal Bovine Serum (FBS) (Hyclone; Logan, Utah), 2-ME (Sigma; St. Louis, Mo.) and Leukemia Inhibitory Factor (LIF) (laboratory preparation).

For preparation of lentivirus, 140 µg of the polycistronic vector (pKP332), 70 µg of the envelope plasmid (pMDG), and 105 µg of the packaging plasmid (pCMBVdR8.9.1) were co-transfected into $1.7 \times 10^7$ 293T cells by the $CaCl_2$ method as previously described (Levasseur et al., Blood 102:4312-9 (2003)). Virus-containing supernatant was collected 2 days after transfection, passed through a 0.45 µm filter and concentrated by centrifugation at 26,000 rpm for 90 minutes at 8° C. in an SW-28 rotor using a Beckman XL-100 ultracentrifuge (Beckman; Fullerton, Calif.).

For iPS cell induction, $3 \times 10^5$ mouse tail-tip fibroblasts (TTFs) were seeded onto one well of a 6-well plate. The next day, 2.5 µL of the concentrated virus was mixed with 2 mL of ES cell medium containing 8 µg/mL polybrene and added to the TTFs. Forty-eight hours later, the TTFs were trypsinized and transferred to a 100 mm dish without MEFs and continuously cultured on the same dish for 3 weeks with daily media changes. Potential iPS cell colonies started to appear after 2-3 weeks. These colonies were individually picked and expanded on MEFs for analysis.

To remove the integrated lentiviral and polycistronic sequences, iPS cells were either electroporated with a Cre-expressing plasmid (pCAGGS-Cre) or infected with a Cre-expressing adenovirus (rAd-Cre-IE). Individual colonies were picked and Cre-mediated removal of floxed sequences was verified by PCR and southern blot analysis.

For the construction of rAd-Cre-IE (rAd-Cre-IRES-EGFP), Cre cDNA was PCR amplified from pCAGGS-Cre and inserted between the NheI and EcoRI sites of the expression vector pEC-IE, which contains an IRES-EGFP downstream of the MCS. The Cre-IE expression cassette is flanked by attL1 and attL2 sites, thus allowing transfer of the Cre-IE sequence from pEC-IE to pAd/pl-DEST (Invitrogen; Carlsbad, Calif.) by the LR reaction. The recombinant adenovirus was packaged in 293A cells according to the manufacturer's instructions.

Primary human keratinocytes were isolated from a patient skin biopsy. Briefly, the biopsied tissue was placed into Keratinocyte-SFM (9K-SFM; Invitrogen; Carlsbad, Calif.) supplemented with 10 mg/ml Dispase and 2× Antibiotics/Antimycotics (CELLnTEC CnT-ABM) and incubated overnight at 4° C. The next day, the keratinocyte-containing epidermal layer was isolated from the fibroblast-containing dermal layer with forceps and then trypsinized for 20 minutes at room temperature. Cell clumps were triturated with a pipet and then centrifuged at 200×g for 5 minutes. Cells were resuspended in K-SFM and 1× Antibiotics/Antimycotics, transferred to one well of a six-well plate, and incubated at 37° C. with daily media changes. For transduction, $3 \times 10^5$ keratinocytes were seeded into one well of a six-well plate in K-SFM. The next day the media was removed and replaced with 2 ml of K-SFM containing 5 mg/ml of polybrene and the polycistronic lentivirus. After 24 hours, the transduced cells were trypsinized, centrifuged, resuspended in K-SFM and transferred into a 10 cm tissue culture dish containing γ-irradiated CF-1 murine embryonic fibroblasts (MEFs). The next day, the medium was changed to human ES cell medium (DMEM/F-12, 20% Knockout SR, 2 mM L-glutamine, 1× Pen/Strep, 1× nonessential amino acids (all from Invitrogen; Carlsbad, Calif.), 0.5 mM β-mercaptoethanol (Sigma; St. Louis, Mo.), and 4 ng/ml bFGF (Calbiochem; San Diego, Calif.)). Cells were incubated at 37° C. with daily media changes and after 10 days, CF-1 conditioned medium was added. iPS colonies appeared after about 30 days.

With the exception of the pKP332 construction, all of the PCRs performed used ExTaq polymerase (Takara Bio Inc.; Otsu, Shiga, Japan). All of the sequencing was performed by the Genomics Core Facility of the Howell and Elizabeth Heflin Center for Human Genetics of the University of Alabama at Birmingham using the BigDye Terminator v3.1 Cycle Sequencing Ready Reaction kit as per the manufacture's instructions (Applied Biosystems; Foster City, Calif.). The sequencing products were run following standard protocols on an Applied Biosystems 3730 Genetic Analyzer with POP-7 polymer.

Immunostaining and AP Staining iPS cells were cultured on cover slips pretreated with FBS, fixed with 4% paraformaldehyde and permeabilized with 0.5% Triton X-100. Cells were stained with DAPI and primary antibodies against Nanog and SSEA1 (R&D Systems; Minneapolis, Minn.) and incubated with fluorophore-labeled secondary antibodies (Jackson Immunoresearch; West Grove, Pa.).

For AP staining, 100-200 iPS cells were seeded onto one well of a six-well plate and cultured for one week. iPS cells were then stained using the Vector Blue Alkaline Phosphatase Substrate Kit III (Vector Laboratories; Burlingame, Calif.) according to the manufacturer's instructions.

RT-PCR Analysis

Total RNA was isolated from cells with Trizol reagent (Invitrogen; Carlsbad, Calif.). RNA was pretreated with RQ1 RNase-free DNase (Promega; Madison, Wis.) and reverse transcribed with SuperScript First-Strand Synthesis System (Invitrogen; Carlsbad, Calif.) using oligo d(T)n. Primers for PCR amplification of the cDNA were: polycistronic transgene F, gatgaactgaccaggcacta (SEQ ID NO:16) and polycistronic transgene R, gattatcggaattccctcgag (SEQ ID NO:17); Nanog F, accaaaggatgaagtgcaag (SEQ ID NO:18) and Nanog R, agttttgctgcaactgtacg (SEQ ID NO:19); Oct4 F, agcttgggctagagaaggat (SEQ ID NO:20) and Oct4 R, tcagtttgaatgcatgggag (SEQ ID NO:21); Sox2 F, tgcacatggcccagcacta (SEQ ID NO:22) and Sox2 R, ttctccagttcgcagtccag (SEQ ID NO:23); Cripto F, aacttgctgtctgaatggag (SEQ ID NO:24) and Cripto R, tttgaggtcctggtccatca (SEQ ID NO:25); Klf4 F, cagcagggactgtcaccctg (SEQ ID NO:26) and Klf4 R, ggtcacatccactacgtgggat (SEQ ID NO:27); and Nat1 F, ggagagtgcgattgcagaag (SEQ ID NO:28) and Nat1 R, ggtcacatccactacgtggga (SEQ ID NO:29).

Bisulfite Modification and Sequencing

Bisulfite treatment of DNA was performed with the CpGenome Fast DNA Modification Kit (Chemicon; Temecula, Calif.) according to the manufacturer's instructions. The Oct4 and Nanog gene promoter regions were amplified by nested PCR using the Oct4 primers F1, gttgttttgttttggttttggatat (SEQ ID NO:30), Oct4 F2, atgggttgaaatattgggtttattta (SEQ ID NO:31) and Oct4 R, ccaccctctaaccttaacctctaac (SEQ ID NO:32) or the Nanog primers F1, gaggatgttttttaagttttttt (SEQ ID NO:33), Nanog F2, aatgtttatggtggattttgtaggt (SEQ ID NO:34) and Nanog R, cccacactcatatcaatataaac (SEQ ID NO:35). Amplified PCR products were purified using a QIAgen Gel Extraction Kit (Qiagen; Valencia, Calif.), cloned into a Topo TA vector (Invitrogen; Carlsbad, Calif.), and sequenced with T7 and M13R primers.

Southern Blot Analysis

Ten µg of genomic DNA were digested with BamHI or KpnI (Roche; Indianapolis, Ind.), separated on a 0.8% agarose gel and blotted onto Hybond-N+ membrane (Amersham Biosciences; Piscataway, N.J.). The polycistronic vector served as template to PCR amplify a 0.3 kb SIN LTR probe using the primers SIN LTR F, gctcggtacctttaagaccaatgac (SEQ ID NO:36) and SIN LTR R, atgctgctagagattttccacactg (SEQ ID NO:37). To produce the internal probe, the polycistronic vector was digested with SalI and XhoI (Roche; Indianapolis, Ind.) and the 1 kb fragment containing the EF1α promoter was gel purified. Probes were labeled using the Random Primed DNA Labeling Kit (Roche; Indianapolis, Ind.) with $^{32}$P-α-dCTP and blots were hybridized in Miracle-Hyb solution (Stratagene; La Jolla, Calif.).

Inverse PCR

One to two µg of total genomic DNA were digested with the tetranucleotide-recognizing restriction enzymes MseI or AluI (New England Biolabs (NEB); Ipswich, Mass.). The digested fragments were diluted and incubated with T4 DNA Ligase (Roche; Indianapolis, Ind.) to obtain self-ligated monomers, which were then linearized with the hexanucleotide-recognizing restriction enzymes NcoI or XmnI (NEB; Ipswich, Mass.). These fragments were isolated by ethanol precipitation and used as templates in PCR reactions using the primers 5LentiR1, tgaattgatcccatcttgtcttcg (SEQ ID NO:38) and SLentiF1, tgctgcttttgcttgtactgg (SEQ ID NO:39). PCR products were run on a 2% agarose gel in the presence of ethidium bromide (0.5 µg/mL). All bands visible under UV light were gel purified and sequenced.

Teratoma Formation

One million iPS cells in a 100 µL volume of PBS were injected via a 21 G needle into the dorsal flanks of SCID mice. Teratomas were recovered 4-5 weeks postinjection and processed for histological analysis.

Production and Analysis of Chimeric Mice

C57BL/6 blastocysts were injected with iPS cells and then transferred to pseudopregnant CD-1 females. After two weeks, embryos were collected for photographs and analyzed for chimerism using PCR. Embryos were individually minced and lysed overnight at 55° C. in a solution of Proteinase K and SDS. DNA was then purified from the lysate by phenol/chloroform extraction and ethanol precipitation. PCR was performed using the primers mbeta KI F, ttgagcaatgtggacagagaagg (SEQ ID NO:40), mbeta KI R, gtcagaagcaaatgtgaggagca (SEQ ID NO:41) and 1400gamma R, aattctggcttatcggaggcaag (SEQ ID NO:42).

Figure 2A:
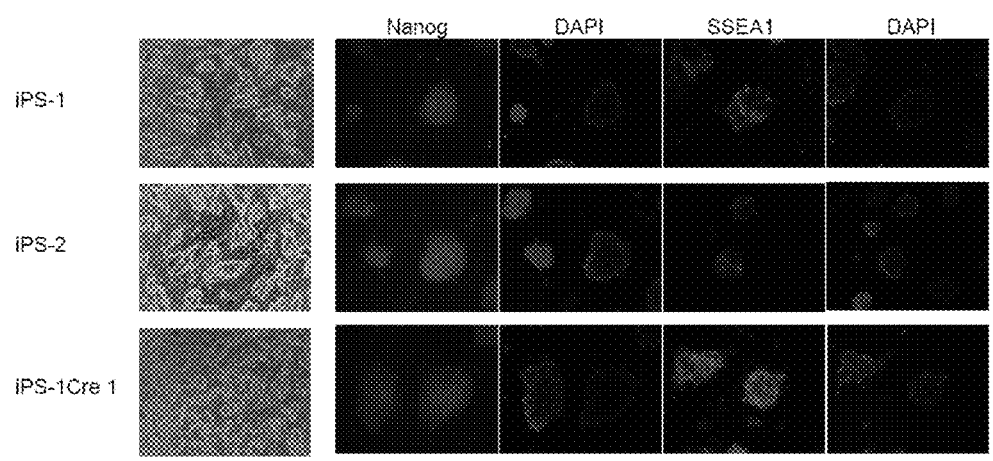
FIG. 2A shows immunofluorescent images of iPS cell colonies stained for Nanog and SSEA1 expression.
Figure 2B:
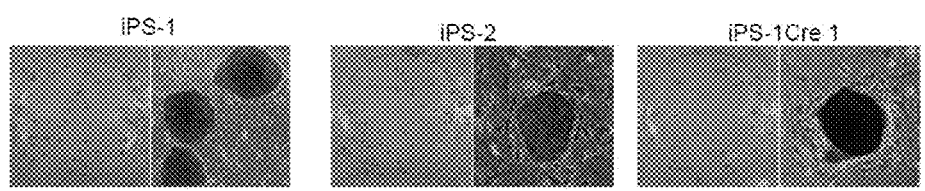
FIG. 2B shows images of iPS cell colonies stained for alkaline phosphatase expression with iPS-1 Cre1 representing a typical colony after Cre recombinase mediated deletion of the OSK vector.

Example 1 iPS Cells Produced by Transduction of Polycistronic Oct4, Sox2, Klf4 (OSK) Vector FIG. 1A illustrates the lentiviral vector constructed for transduction of adult skin fibroblasts. Human Oct4, Sox2 and Klf4 cDNAs (OSK) were linked with porcine teschovirus-1 (PTV1) 2A sequences that function as cis-acting hydrolase elements (CHYSELs) to trigger ribosome skipping (Donnelly et al., J. Gen. Virol. 82:1013-25 (2001); Chinnasamy et al., Virol. J. 3:14 (2006)). The 2A peptide sequences (FIG. 1B) are cleaved during translation and produce Oct4 and Sox2 proteins containing an additional 21 amino acids at the carboxy-termini. A single proline is also appended to the amino-termini of Sox2 and Klf4. The OSK polycistron was subcloned downstream of an EF1α promoter in a self-inactivating (SIN) lentiviral vector containing a loxP site in the truncated 3' LTR (Zuffferey et al., J. Virol. 72:9873-80 (1998); Levasseur et al., Blood 102:4312-9 (2003)). After lentivirus production, one million adult skin fibroblasts derived from tail tips of humanized sickle mice were transduced with the polycistronic vector, and four colonies with highly defined borders and tightly packed cells were picked at 19 to 30 days post-transduction. These colonies were expanded and stained for alkaline phosphatase, Nanog and SSEA1, which are characteristic markers of pluripotent stem cells. FIGS. 2A and 2B illustrate the staining pattern of typical colonies (iPS-1 and iPS-2). The colonies stained intensely for alkaline phosphatase and strongly with antibodies to Nanog and SSEA1.

Figure 3A:
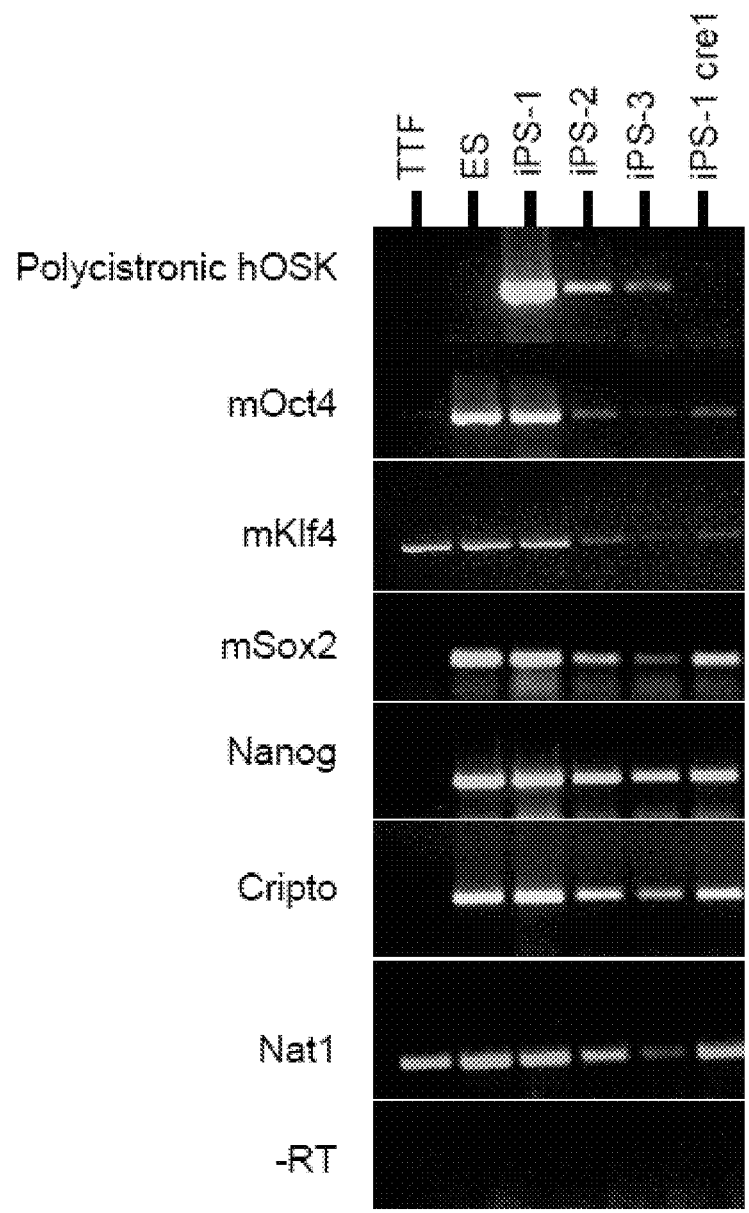
FIG. 3A shows a gel of RT-PCR assays of polycistronic OSK RNA and endogenous Oct4, Sox2, Klf4, Nanog and Cripto RNA in iPS cells from 3 independent colonies (iPS-1, iPS-2, and iPS-3) and from iPS-1 cells post Cre recombinase mediated deletion of the OSK lentiviral vector (iPS-1 Cre1).
Figure 3B:
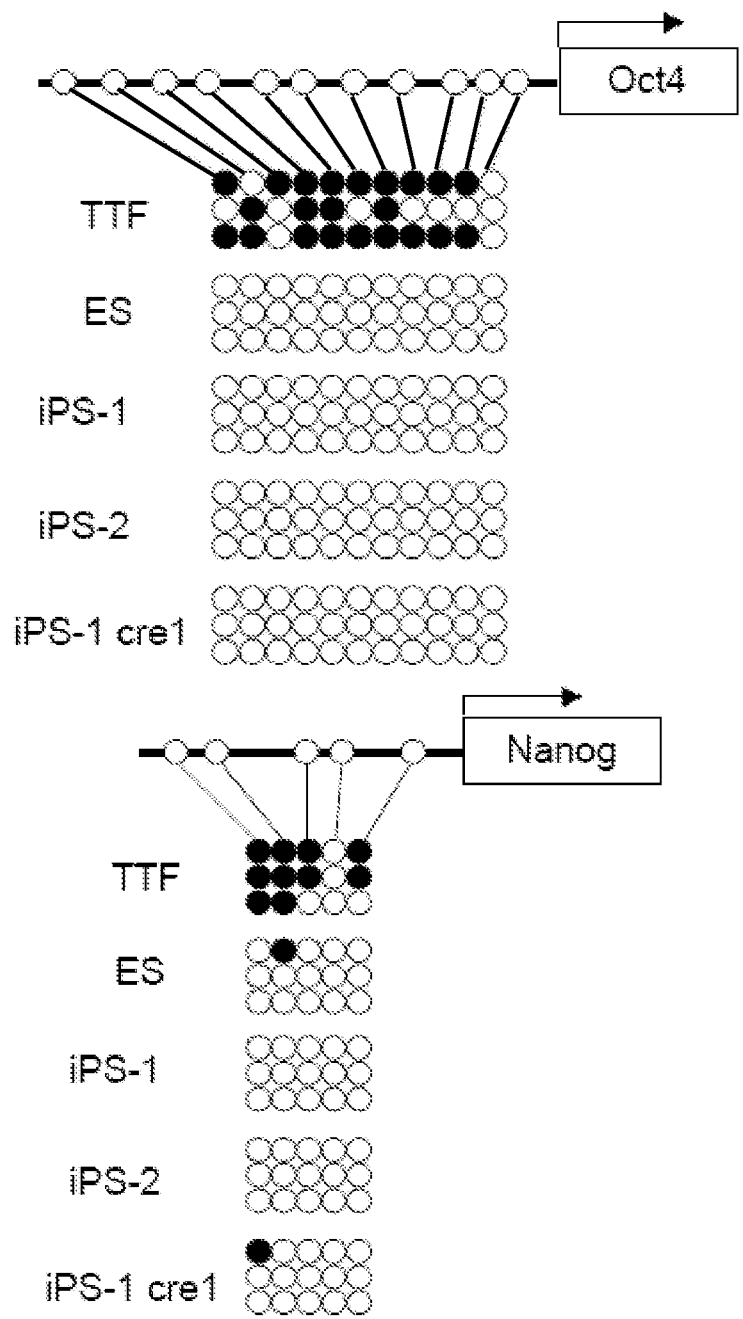
FIG. 3B shows bisulfite sequencing of the endogenous and Oct4 and Nanog promoters in iPS-1, iPS-2, and iPS-1 Cre1 cells. Filled circles represent methylated CpGs and open circles represent unmethylated CpGs.

Reverse transcription-polymerase chain reaction (RT-PCR) assays for expression of additional iPS cell markers are shown in FIG. 3. iPS-1, -2, and -3 cells expressed polycistronic OSK RNA and endogenous Oct4, Sox2, Klf4, Nanog and Cripto RNA (FIG. 3A). Consistent with these results, bisulfite sequencing of the endogenous Oct4 and Nanog promoters in iPS-1 and iPS-2 cells demonstrated effective demethylation of these sequences (FIG. 3B). CpGs in the endogenous Oct4 and Nanog promoters of tail tip fibroblasts (TTFs) were highly methylated (FIG. 3B) and endogenous Oct4, Sox2, Nanog and Cripto RNAs were not detected (FIG. 3A).

Figure 5A:
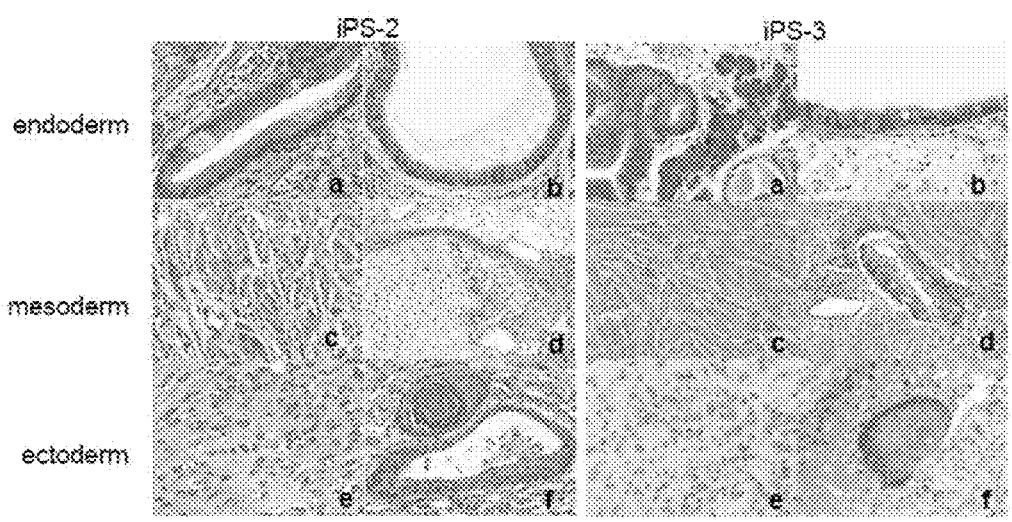
FIG. 5A shows teratomas containing tissue derived from all three germ layers in NOD/SCID IL-2γR −/− mice injected with isolated iPS cells. a, intestine-like epithelium, with pancreatic acini in iPS-3 teratoma; b, respiratory epithelium; c, skeletal muscle; d, bone, with hyaline cartilage in iPS-2 teratoma; e, nervous tissue; f, skin-like stratified squamous epithelium.

When these iPS cells were injected into the dorsal flanks of nonobese diabetic (NOD)/SCID IL-2 γR –/– mice, teratomas containing tissue derived from all three germ layers were obtained (FIG. 5A). These results demonstrate that the polycistronic OSK lentiviral vector effectively reprograms adult skin fibroblasts to induced pluripotent stem cells.

Example 2

Figure 4A:
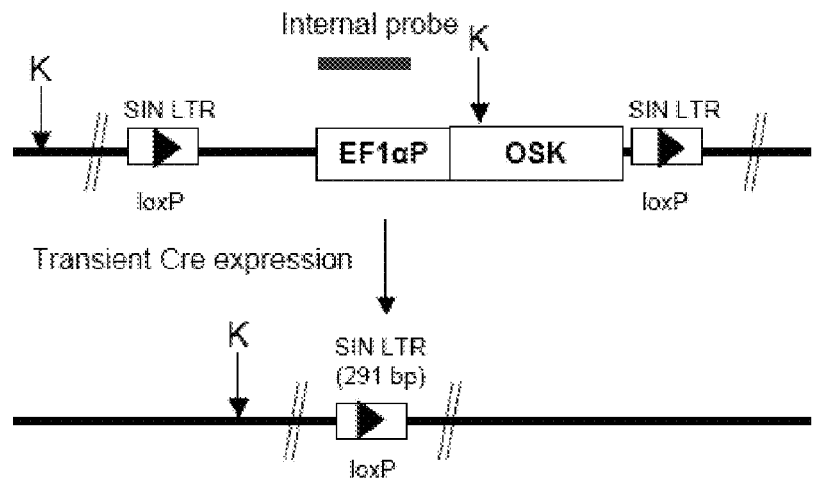
FIG. 4A shows a map of the OSK vector pre- and post-Cre expression. K represents KpnI cleavage sites. The probe binding site is shown.
Figure 4B:
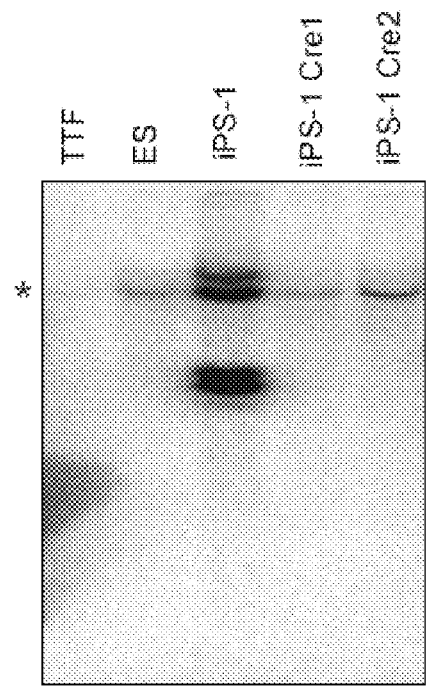
FIG. 4B shows a Southern Blot demonstrating that iPS-1 cells contain 4 copies of the OSK lentiviral vector, and iPS-1 Cre1 cells contain no copies of the vector after transient Cre expression.
Figure 6A:
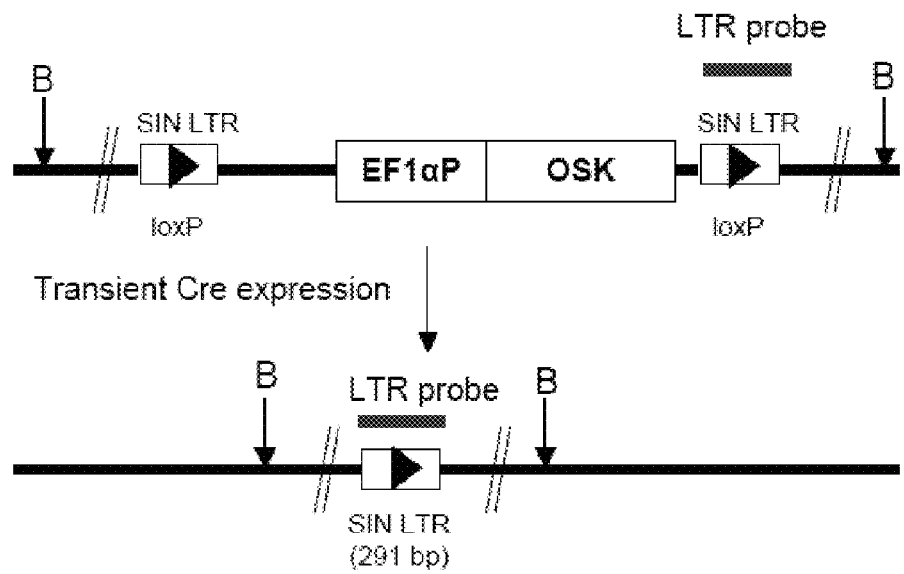
FIG. 6A shows a map of the OSK vector pre- and post-Cre expression. The probe binding site is shown.
Figure 6B:
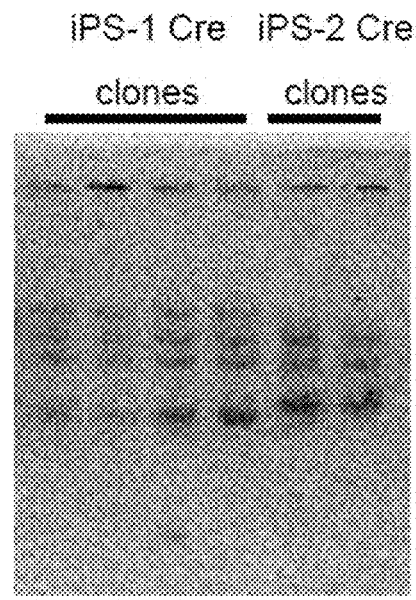
FIG. 6B shows a Southern blot demonstrating that iPS-1 Cre cells contain 4 insertion sites and iPS-2 Cre cells contain 3 insertion sites.

Removal of Polycistronic OSK Vector From iPS Cell Genome by Exogenous Cre Recombinase Expression The polycistronic vector was deleted by electroporation of iPS cells with a Cre recombinase-expressing plasmid or by infection of iPS cells with adenovirus that expresses Cre recombinase (Adeno/Cre). Subsequently, individual colonies were picked, expanded and iPS cell DNA was analyzed by Southern blot hybridization (FIG. 4). DNA isolated before (iPS-1) and after (iPS-1 Cre) Cre expression was digested with Kpn I, which cuts once within the OSK polycistron, and probed with a DNA fragment containing EF1α sequences. Four bands are observed for iPS-1 DNA indicating that four copies of the polycistronic OSK vector are integrated into the genome (also see FIG. 6, iPS-2 cells contain 3 copies of the vector). None of these four bands are observed in iPS-1 Cre DNA; only a band representing endogenous EF1α sequences is detected. These results demonstrate that transient Cre expression effectively deletes all copies of the polycistronic OSK lentiviral vector.

Junctions of the four iPS-1 insertion sites were cloned by inverse PCR and sequenced (Pawlik et al., Gene 165:173-81 (1995); Silver and Keerikatte, J. Virol. 63:1924-8 (1989)). Table 2 lists the locations of these sites. Three of the insertion sites are within introns, and one is located in an intergenic region that is 2 megabases (Mb) downstream of the transcription start site (TSS) of the NMBr gene and 1 Mb upstream of the TSS of the Cited2 gene. These results demonstrate that iPS cells can be readily obtained by this procedure without interruption of coding sequences, promoters or known regulatory elements. Cloning and sequencing of the insertion sites from iPS-1 Cre cells demonstrated that only the 291 base pair (bp) 3' LTR of the polycistronic vector remains in the genome. This small SIN LTR does not contain a promoter or enhancer; therefore, the probability of insertional activation or inactivation of endogenous genes is low.

TABLE 2

OSK lentiviral integration sites.

| iPS Clones | No: | Chrom. | Gene Name | Gene ID | Location | Base from TSS |
|---|---|---|---|---|---|---|
| iPS-1 | 1 | CH2 | RAB14 | MGI: 1915615 | Intron | +8,129 |
| | 2 | CH8 | Cadherin 13 | MGI: 99551 | Intron | +24,738 |
| | 3 | CH10 | Cbp/p300-interacting transactivator | MGI: 1306784 | Intergenic | −966,513 |
| | 4 | CH14 | F-box protein 34 | MGI: 1926188 | Intron | +52,366 |
| iPS-2 | 1 | CH5 | Ribokinase | MGI: 1918586 | Intron | +38,503 |
| | 2 | CH15 | Estrogen receptor-binding fragment associated gene 9 | MGI: 1859920 | Intron | +20,439 |
| | 3 | CH15 | Angiopoietin 1 | MGI: 108448 | Intron | +21,069 |

FIG. 2 demonstrates that iPS-1 Cre cells continue to stain positive for alkaline phosphatase, Nanog and SSEA1 after OSK deletion, and FIG. 3 demonstrates that expression of endogenous Oct4, Sox2, Klf4, Nanog and Cripto was maintained in the absence of OSK expression. As expected, the endogenous Oct4 and Nanog promoters remained demethylated after OSK deletion (FIGS. 3B and 3C).

Figure 5B:
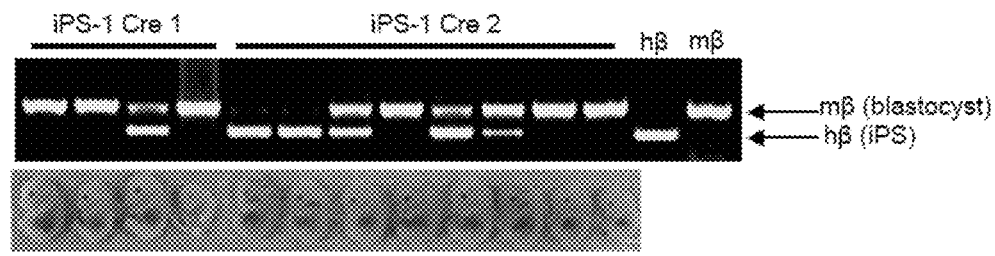
FIG. 5B shows chimeric embryos that were obtained following injection of iPS-1 Cre1 and iPS-1 Cre2 cells into wild type blastocysts. The top panel is a gel showing PCR products demonstrating chimeric embryos as iPS cells contain the human β-globin gene as a marker.
Figure 5C:
FIG. 5C shows an adult chimeric animal (right) compared to an adult non-chimeric littermate (left).

Finally, two iPS-1 Cre cell lines were injected into wild-type blastocysts, and these blastocysts were transferred into the uteri of pseudo-pregnant female mice. After two weeks, embryos were analyzed for chimerism by PCR with primers specific for human and mouse β-globin genes. FIG. 5B demonstrates that several high-level chimeras were obtained; most tissues of these embryos were derived from iPS-1 Cre cells which contain only human β-globin genes. One pregnancy was allowed to proceed to term, and FIG. 5C shows an adult high-level chimera (right) derived from iPS-1 Cre 2 cells. These results demonstrate that adult skin fibroblasts can be effectively reprogrammed to iPS cells with the polycistronic lentiviral vector and that tissues from all three germ layers can be derived from these cells.

Example 3 iPS Cells Derived from Human Keratinocytes

Figure 8:
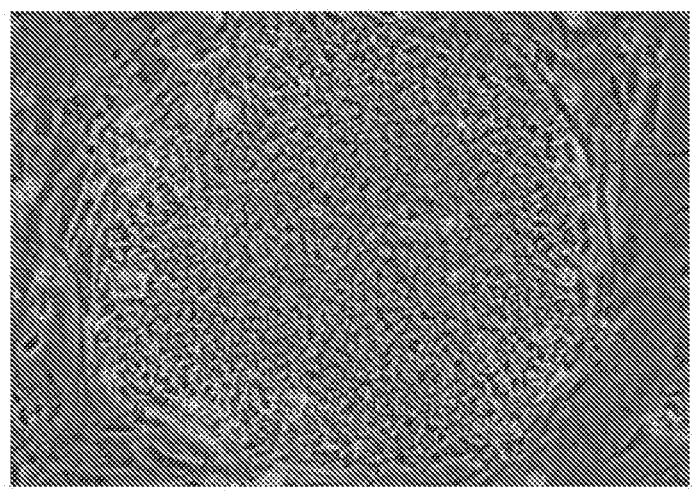
FIG. 8 shows a brightfield image of an iPS cell colony derived from human keratinocytes using a polycistronic lentiviral vector.

To determine whether iPS cells were produced from primary human keratinocytes, primary human keratinocytes were cultured from a patient skin biopsy. The cultured cells were transduced with the vector described above. After 24 hours, the transduced cells were trypsinized, centrifuged, resuspended in media and transferred into a tissue culture dish containing murine embryonic fibroblasts (MEFs). After about 30 days in culture, iPS colonies were produced. The iPS cells from the human keratinocytes were sustainable in culture and were capable of multiple passages. FIG. 8 shows a brightfield image of one of the iPS cell colonies produced. The iPS cell colony was stained with −4, which is an antibody that recognizes human embryonic stem cells, but not differentiated cells, to confirm the presence of embryonic stem cells comprising the iPS cell colony. The same iPS colony was stained with DAPI, which is a general nuclear stain, to confirm the presence of nuclei in the cells of the iPS cell colony.

Example 4

Correction of Sickle Cell Disease (SCD) with Concomitant Formation of iPS Cells

Figure 9:
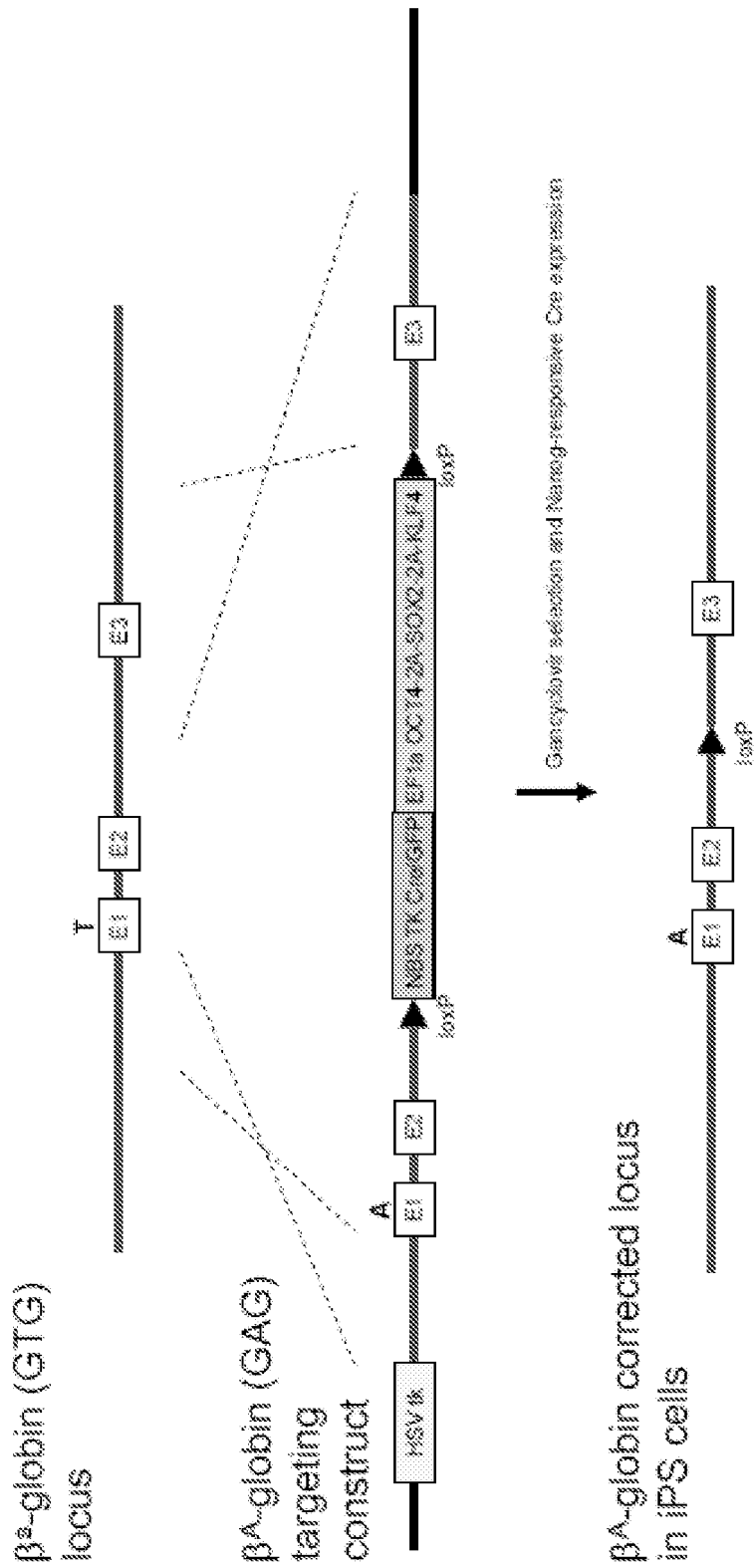
FIG. 9 shows a schematic of a method to correct a β-globin mutation found in sickle cell disease with concomitant formation of iPS cells. The $β^s$-globin locus is depicted at the top of the figure. The β-globin locus has a single nucleotide, A to T transversion in the first exon. The targeting vector is depicted in the middle of the figure. The vector contains the normal GAG codon in the first exon flanked by sequences to effect homologous recombination. A herpes simplex virus thymidine kinase (HSV tk) gene is located outside of the sequences used to effect homologous recombination. Integrated between the homology arms is a floxed cassette (loxP site on either side of cassette) consisting of a Nanog-responsive (NBS) thymidine kinase (TK) promoter driving expression of Cre recombinase and the EF1α promoter driving expression of the Oct4-Sox2-Klf4 polycistronic sequence. The dashed lines show where the homologous recombination occurs. After homologous recombination occurs, the endogenous Nanog gene is expressed. Nanog binds to the NBS sites and forces Cre recombinase expression. Cre recombinase excises the floxed cassette and leaves behind a correct β-globin locus with a single loxP site in between exons 2 and 3 of β-globin.

FIG. 9 shows a schematic of a method to correct a $β^s$-globin mutation in a cell from a subject with sickle cell disease (SCD) while dedifferentiating the cell to a pluripotent state. The method is applicable to a range of genetic mutations.

To determine whether the β-globin locus of a subject with SCD is corrected, cells from a human subject with SCD are collected and expanded in culture. The mutated $β^s$-globin locus is depicted at the top of FIG. 9. The $β^s$-globin mutation is a single nucleotide, A to T transversion, that changes the normal GAG codon to a GTG codon in exon 1 of β-globin. As a result, the sixth amino acid of the $β^s$-globin is a valine instead of the normal glutamic acid.

Once the cells are expanded in culture, the targeting vector (middle of FIG. 9) is introduced into the cells from the subject with SCD. The vector contains the normal GAG nucleotide sequence in the first exon and flanking sequences to effect homologous recombination within the target locus. A herpes simplex virus thymidine kinase (HSV tk) gene is located outside of the sequences used to effect homologous recombination. Integrated between the flanking homology arms is a floxed cassette consisting of a Nanog-responsive thymidine kinase promoter driving expression of a Cre recombinase and the EF1α promoter driving expression of the Oct4-Sox2-Klf4 polycistronic sequence. Alternatively, the floxed cassette can contain a marker gene that can either be an addition to the polycistron or have its own promoter. The marker can be used as a positive selection to select cells that have incorporated the vector.

The targeting vector homologously recombines with the mutated $β^s$-globin locus incorporating the corrected GAG codon. The Oct4-Sox2-Klf4 polycistron is expressed, resulting in the dedifferentiation of the cells. While Oct4, Sox2, and Klf4 are expressed from the EF1α promoter, the TK promoter remains silent. Once the cell begins to dedifferentiate, the endogenous Nanog gene is expressed. Expression of Nanog results in the activation of the TK promoter, which is Nanog responsive. Activation of the TK promoter results in the expression of Cre recombinase. Cre recombinase binds to the loxP sites to effect the deletion of the floxed cassette, resulting in a corrected β-globin locus containing a single loxP site in between the second and third exons of the corrected β-globin locus (bottom of FIG. 9). Excision of the floxed cassette is important for two reasons: (1) it prevents the disregulation of the corrected β-globin gene, and (2) it halts the expression of the vector-introduced reprogramming factors, as their continued expression inhibits the reprogramming process.

What is claimed is:

1. A vector comprising (i) a nucleic acid sequence encoding an Oct4, (ii) a nucleic acid sequence encoding a Sox2, and (iii) a nucleic acid sequence encoding a Klf4, wherein each of the nucleic acid sequences, (i)-(iii), are separated by a first and second nucleic acid encoding sequence a porcine teschovirus-1 (PTV1) 2A sequence, wherein the vector comprises a nucleic acid sequence encoding SEQ ID NO: 9.

2. The vector of claim 1, wherein the vector comprises SEQ ID NO:7.

3. The vector of claim 1, wherein the vector is designed to correct a genetic mutation, the vector further comprising an unmutated nucleic acid sequence of interest and homologous nucleic acid sequences flanking the genetic mutation.

4. The vector of claim 3, wherein the unmutated nucleic acid sequence of interest comprises the nucleic acid sequence encoding β-globin.

5. The vector of claim 4, wherein the vector further comprises a first and second loxP sequence.

6. The vector of claim 5, wherein the vector further comprises a nucleic acid sequence encoding a Cre recombinase operably linked to an inducible promoter.

7. The vector of claim 6, wherein the inducible promoter comprises a Nanog-responsive thymidine kinase promoter.

8. The vector of claim 1, wherein the vector is a plasmid, an adenoviral vector or a retroviral vector.

9. The vector of claim 8, wherein the retroviral vector is a lentiviral vector.

10. The vector of claim 9, wherein the lentiviral vector is a lentiviral SIN vector.

11. The vector of claim 8, wherein the retroviral vector comprises a 3' long terminal repeat.

12. The vector of claim 11, wherein the retroviral vector further comprises a loxP sequence.

13. The vector of claim 12, wherein the loxP sequence is in the 3' long terminal repeat of the lentiviral vector.

14. A kit comprising (i) the vector of claim 1 and (ii) a vector comprising a nucleic acid sequence encoding a Cre recombinase.

15. The vector of claim 1, wherein the vector comprises SEQ ID NO: 43.

* * * * *

SEQUENCE LISTING

<160> NUMBER OF SEQ ID NOS: 44

<210> SEQ ID NO 1
<211> LENGTH: 22
<212> TYPE: PRT
<213> ORGANISM: Artificial sequence
<220> FEATURE:
<223> OTHER INFORMATION: Synthetic construct

<400> SEQUENCE: 1

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 2
<211> LENGTH: 19
<212> TYPE: PRT
<213> ORGANISM: Artificial sequence
<220> FEATURE:
<223> OTHER INFORMATION: Synthetic construct

<400> SEQUENCE: 2

Ala Thr Asn Phe Ser Leu Leu Lys Gln Ala Gly Asp Val Glu Glu Asn
1               5                   10                  15

Pro Gly Pro

<210> SEQ ID NO 3
<211> LENGTH: 18
<212> TYPE: PRT
<213> ORGANISM: Artificial sequence
<220> FEATURE:
<223> OTHER INFORMATION: Synthetic construct

<400> SEQUENCE: 3

Glu Gly Arg Gly Ser Leu Leu Thr Cys Gly Asp Val Glu Glu Asn Pro
1               5                   10                  15

Gly Pro

<210> SEQ ID NO 4
<211> LENGTH: 3
<212> TYPE: PRT
<213> ORGANISM: Artificial sequence
<220> FEATURE:
<223> OTHER INFORMATION: Synthetic construct

<400> SEQUENCE: 4

Gly Ser Gly
1

<210> SEQ ID NO 5
<211> LENGTH: 21
<212> TYPE: PRT
<213> ORGANISM: Artificial sequence
<220> FEATURE:
<223> OTHER INFORMATION: Synthetic construct

<400> SEQUENCE: 5

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 6

```
<211> LENGTH: 34
<212> TYPE: DNA
<213> ORGANISM: Artificial sequence
<220> FEATURE:
<223> OTHER INFORMATION: Synthetic construct

<400> SEQUENCE: 6
ataacttcgt ataatgtatg ctatacgaag ttat                                34

<210> SEQ ID NO 7
<211> LENGTH: 3623
<212> TYPE: DNA
<213> ORGANISM: Artificial sequence
<220> FEATURE:
<223> OTHER INFORMATION: Synthetic construct

<400> SEQUENCE: 7
cacacagcgg ccgcatttaa atccaccatg gcgggacacc tggcttcgga tttcgccttc      60 tcgcccccctc caggtggtgg aggtgatggg ccaggggggc cggagccggg ctgggttgat    120
cctcggacct ggctaagctt ccaaggccct cctggagggc caggaatcgg gccggggtt     180 gggccaggct ctgaggtgtg ggggattccc ccatgccccc cgccgtatga gttctgtggg    240
gggatggcgt actgtgggcc ccaggttgga gtggggctag tgcccaagg cggcttggag     300 acctctcagc ctgagggcga agcaggagtc ggggtggaga gcaactccga tggggcctcc    360
ccggagccct gcaccgtcac ccctggtgcc gtgaagctgg agaaggagaa gctggagcaa    420
aacccggagg agtcccagga catcaaagct ctgcagaaag aactcgagca atttgccaag    480
ctcctgaagc agaagaggat cacccgtgga tatacacagg ccgatgtggg gctcaccctg    540
ggggttctat ttgggaaggt attcagccaa acgaccatct gccgctttga ggctctgcag    600
cttagcttca gaacatgtg taagctgcgg cccttgctgc agaagtgggt ggaggaagct    660
gacaacaatg aaaatcttca ggagatatgc aaagcagaaa ccctcgtgca ggcccgaaag    720
agaaagcgaa ccagtatcga gaaccgagtg agaggcaacc tggagaattt gttcctgcag    780
tgcccgaaac ccacactgca gcagatcagc cacatcgccc agcagcttgg gctcgagaag    840
gatgtggtcc gagtgtggtt ctgtaaccgg cgccagaagg gcaagcgatc aagcagcgac    900
tatgcacaac gagaggattt tgaggctgct gggtctcctt tctcaggggg accagtgtcc    960
tttcctctgg ccccagggcc ccattttggt accccaggct atgggagccc tcacttcact   1020
gcactgtact cctcggtccc tttccctgag ggggaagcct ttccccctgt ctccgtcacc   1080
actctgggct ctcccatgca ttcaaacgga tccggagcca cgaacttctc tctgttaaag   1140
caagcaggag atgttgaaga aaaccccggg cctatgtaca acatgatgga gacggagctg   1200
aagccgccgg gcccgcagca aacttcgggg gcggcggcg gcaactccac cgcggcggcg   1260
gccggcggca accagaaaaa cagcccggac cgcgtcaagc ggcccatgaa tgccttcatg   1320
gtgtggtccc gcgggcagcg gcgcaagatg gcccaggaga accccaagat gcacaactcg   1380
gagatcagca agcgcctggg cgccgagtgg aaacttttgt cggagacgga agcggccg    1440 ttcatcgacg aggctaagcg gctgcgagcg ctgcacatga aggagcaccc ggattataaa   1500
taccggcccc ggcggaaaac caagacgctc atgaagaagg ataagtacac gctgcccggc   1560
gggctgctgg cccccggcgg caatagcatg gcgagcgggg tcgggtggg cgccggcctg   1620 ggcgcgggcg tgaaccagcg catggacagt tacgcgcaca tgaacggctg gagcaacggc   1680
agctacagca tgatgcagga ccagctgggc taccgcagc acccgggcct caatgcgcac   1740
ggcgcagcgc agatgcagcc catgcaccgc tacgacgtga gcgccctgca gtacaactcc   1800
```

```
atgaccagct cgcagaccta catgaacggc tcgcccacct acagcatgtc ctactcgcag    1860
cagggcaccc ctggcatggc tcttggctcc atgggttcgg tggtcaagtc cgaggccagc    1920
tccagccccc ctgtggttac ctcttcctcc cactccaggg cgccctgcca ggccggggac    1980
ctccgggaca tgatcagcat gtatctcccc ggcgccgagg tgccggaacc cgccgccccc    2040
agcagacttc acatgtccca gcactaccag agcggcccgg tgcccggcac ggccattaac    2100
ggcacactgc ccctctcaca catgggatcc ggagccacga acttctctct gttaaagcaa    2160
gcaggagatg ttgaagaaaa ccccgggcct atggctgtca gcgacgcgct gctcccatct    2220
ttctccacgt tcgcgtctgg cccggcggga agggagaaga cactgcgtca gcaggtgcc     2280 ccgaataacc gctggcggga ggagctctcc cacatgaagc gacttccccc agtgcttccc    2340 ggccgccccct atgacctggc ggcggcgacc gtggccacag acctggagag cggcggagcc   2400
ggtgcggctt gcggcggtag caacctggcg ccccctacct ggagagagac cgaggagttc    2460
aacgatctcc tggacctgga ctttattctc tccaattcgc tgacccatcc tccggagtca    2520
gtggccgcca ccgtgtcctc gtcagcgtca gcctcctctt cgtcgtcgcc gtcgagcagc    2580
ggccctgcca gcgcgccctc cacctgcagc ttcacctatc cgatccgggc cgggaacgac    2640
ccgggcgtgg cgccgggcgg cacgggcgga ggcctcctct atggcaggga gtccgctccc    2700
cctccgacgg ctcccttcaa cctggcggac atcaacgacg tgagccctc gggcggcttc     2760 gtggccgagc tcctgcggcc agaattggac ccggtgtaca ttccgccgca gcagccgcag    2820
ccgccaggtg gcgggctgat gggcaagttc gtgctgaagg cgtcgctgag cgcccctggc    2880
agcgagtacg cagcccgtc ggtcatcagc gtcagcaaag cagccctga cggcagccac      2940 ccggtggtgg tggcgcccta acaggcgggg ccgccgcgca cgtgccccaa gatcaagcag    3000
gaggcggtct cttcgtgcac ccacttgggc gctggacccc ctctcagcaa tggccaccgg    3060
ccggctgcac acgactttccc cctggggcgg cagctcccca gcaggactac cccgaccctg    3120
ggtcttgagg aagtgctgag cagcagggac tgtcacccctg ccctgccgct tcctcccggc    3180
ttccatcccc acccggggcc caattaccca tccttcctgc cgatcagat gcagccgcaa     3240 gtcccgccgc tccattacca agagctcatg ccacccggtt cctgcatgcc agaggagccc    3300
aagccaaaga ggggaagacg atcgtggccc cggaaaagga ccgccaccca cacttgtgat    3360
tacgcgggct gcggcaaaac ctacacaaag agttcccatc tcaaggcaca cctgcgaacc    3420
cacacaggtg agaaacctta ccactgtgac tgggacggct gtggatggaa attcgcccgc    3480
tcagatgaac tgaccaggca ctaccgtaaa cacgggggc accgcccgtt ccagtgccaa     3540
aaatgcgacc gagcatttc caggtcggac cacctcgcct acacatgaa gaggcattt      3600 taaatttaaa tgtcgactgt gtg                                            3623
```

<210> SEQ ID NO 8
<211> LENGTH: 3623
<212> TYPE: DNA
<213> ORGANISM: Artificial sequence
<220> FEATURE:
<223> OTHER INFORMATION: synthetic construct

<400> SEQUENCE: 8

```
gtgtgtcgcc ggcgtaaatt taggacctac cgccctgtgg accgaagcct aaagcggaag      60
agcgggggag gtccaccacc tccactaccc ggtccccccg gcctcggccc gacccaacta     120
ggagcctgga ccgattcgaa ggttccggga ggacctcccg gtccttagcc cggccccaa     180
```

```
cccggtccga gactccacac cccctaaggg ggtacgggggg cggcatact caagacaccc      240 ccctaccgca tgacacccgg ggtccaacct cacccgatc acgggttcc gccgaacctc       300 tggagagtcg gactcccgct tcgtcctcag ccccacctct cgttgaggct accccggagg     360
ggcctcggga cgtggcagtg gggaccacgg cacttcgacc tcttcctctt cgacctcgtt    420
ttgggcctcc tcagggtcct gtagtttcga gacgtctttc ttgagctcgt taaacggttc    480
gaggacttcg tcttctccta gtgggaccct atatgtgtcc ggctacaccc cgagtgggac    540
ccccaagata aacccttcca taagtcggtt tgctggtaga cggcgaaact ccgagacgtc    600
gaatcgaagt tcttgtacac attcgacgcc gggaacgacg tcttcaccca cctccttcga    660
ctgttgttac ttttagaagt cctctatacg tttcgtcttt gggagcacgt ccgggctttc    720
tctttcgctt ggtcatagct cttggctcac tctccgttgg acctcttaaa caaggacgtc    780
acgggctttg ggtgtgacgt cgtctagtcg gtgtagcggg tcgtcgaacc cgagctcttc    840
ctacaccagg ctcacaccaa gacattggcc gcggtcttcc cgttcgctag ttcgtcgctg    900
atacgtgttg ctctcctaaa actccgacga cccagaggaa agagtccccc tggtcacagg    960
aaaggagacc ggggtccccgg ggtaaaacca tggggtccga taccctcggg agtgaagtga    1020
cgtgacatga ggagccaggg aaagggactc cccccttcgga aaggggggaca gaggcagtgg    1080 tgagacccga gagggtacgt aagtttgcct aggcctcggt gcttgaagag agacaatttc    1140
gttcgtcctc tacaacttct ttttgggggccc ggatacatgt tgtactacct ctgcctcgac   1200
ttcggcggcc cgggcgtcgt ttgaagcccc ccgccgccgc cgttgaggtg gcgccgccgc    1260
cggccgccgt tggtctttttt gtcgggcctg gcgcagttcg ccgggtactt acggaagtac    1320
cacaccaggg cgcccgtcgc cgcgttctac cgggtcctct tggggttcta cgtgttgagc    1380
ctctagtcgt tcgcggaccc gcggctcacc tttgaaaaca gcctctgcct cttcgccggc    1440
aagtagctgc tccgattcgc cgacgctcgc gacgtgtact tcctcgtggg cctaatattt    1500
atggccgggg ccgccttttg gttctgcgag tacttcttcc tattcatgtg cgacgggccg    1560
cccgacgacc ggggggccgcc gttatcgtac cgctcgcccc agccccaccc gcggccggac    1620 ccgcgccccga acttggtcgc gtacctgtca atgcgcgtgt acttgccgac ctcgttgccg    1680
tcgatgtcgt actacgtcct ggtcgacccg atgggcgtcg tgggcccgga gttacgcgtg    1740
ccgcgtcgcg tctacgtcgg gtacgtggcc atgctgcact cgcgggacgt catgttgagg    1800
tactggtcga gcgtctggat gtacttgccg agcgggtgga tgtcgtacag gatgagcgtc    1860
gtcccgtggg gaccgtaccg agaaccgagg tacccaagcc accagttcag gctccggtcg    1920
aggtcggggg gacaccaatg gagaaggagg gtgaggtccc gcgggacggt ccggcccctg    1980
gaggccctgt actagtcgta catagaggggg ccgcggctcc acggccttgg gcggcggggg    2040
tcgtctgaag tgtacagggt cgtgatggtc tcgccgggcc acgggccgtg ccggtaattg    2100
ccgtgtgacg gggagagtgt gtaccctagg cctcggtgct tgaagagaga caatttcgtt    2160
cgtcctctac aacttctttt gggggcccgga taccgacagt cgctgcgcga cgagggtaga    2220
aagaggtgca agcgcagacc gggccgccct tccctcttct gtgacgcagt tcgtccacgg    2280
ggcttattgg cgaccgccct cctcgagagg gtgtacttcg ctgaaggggg tcacgaaggg    2340
ccggcgggga tactggaccg ccgccgctgg caccggtgtc tggacctctc gccgcctcgg    2400
ccacgccgaa cgccgccatc gttggaccgc ggggatggag cctctctctg gctcctcaag    2460
ttgctagagg acctggacct gaaataagag aggttaagcg actgggtagg aggcctcagt    2520
caccggcggt ggcacaggag cagtcgcagt cggaggagaa gcagcagcgg cagctcgtcg    2580
```

```
ccgggacggt cgcgcgggag gtggacgtcg aagtggatag gctaggcccg gcccttgctg    2640
ggcccgcacc gcggcccgcc gtgcccgcct ccggaggaga taccgtccct caggcgaggg    2700
ggaggctgcc gagggaagtt ggaccgcctg tagttgctgc actcggggag cccgccgaag    2760
caccggctcg aggacgccgg tcttaacctg ggccacatgt aaggcggcgt cgtcggcgtc    2820
ggcggtccac cgcccgacta cccgttcaag cacgacttcc gcagcgactc gcgggaccg     2880 tcgctcatgc cgtcgggcag ccagtagtcg cagtcgtttc cgtcgggact gccgtcggtg    2940
ggccaccacc accgcgggat gttgccgccc ggcggcgcgt gcacggggtt ctagttcgtc    3000
ctccgccaga gaagcacgtg ggtgaacccg cgacctgggg gagagtcgtt accggtggcc    3060
ggccgacgtg tgctgaaggg ggaccccgcc gtcgaggggt cgtcctgatg gggctgggac    3120
ccagaactcc ttcacgactc gtcgtccctg acagtgggac gggacggcga aggagggccg    3180
aaggtagggg tgggccccgg gttaatgggt aggaaggacg ggctagtcta cgtcggcgtt    3240
cagggcggcg aggtaatggt tctcgagtac ggtgggccaa ggacgtacgg tctcctcggg    3300
ttcggtttct cccctctctgc tagcaccggg gcctttcct ggcggtgggt gtgaacacta    3360
atgcgcccga cgccgttttg gatgtgtttc tcaagggtag agttccgtgt ggacgcttgg    3420
gtgtgtccac tctttggaat ggtgacactg accctgccga cacctacctt taagcgggcg    3480
agtctacttg actggtccgt gatggcattt gtgtgccccg tggcgggcaa ggtcacggtt    3540
tttacgctgg ctcgtaaaag gtccagcctg gtggagcgga atgtgtactt ctccgtaaaa    3600
atttaaattt acagctgaca cac                                            3623
```

<210> SEQ ID NO 9
<211> LENGTH: 1191
<212> TYPE: PRT
<213> ORGANISM: Artificial sequence
<220> FEATURE:
<223> OTHER INFORMATION: Synthetic construct

<400> SEQUENCE: 9

```
Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175
```

```
Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
            195                 200                 205

Glu Glu Ala Asp Asn Asn Glu Asn Leu Gln Glu Ile Cys Lys Ala Glu
210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
            275                 280                 285

Ser Ser Asp Tyr Ala Gln Arg Glu Asp Phe Glu Ala Ala Gly Ser Pro
290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn Gly Ser Gly Ala Thr Asn Phe Ser
            355                 360                 365

Leu Leu Lys Gln Ala Gly Asp Val Glu Glu Asn Pro Gly Pro Met Tyr
            370                 375                 380

Asn Met Met Glu Thr Glu Leu Lys Pro Pro Gly Pro Gln Gln Thr Ser
385                 390                 395                 400

Gly Gly Gly Gly Gly Asn Ser Thr Ala Ala Ala Ala Gly Gly Asn Gln
                405                 410                 415

Lys Asn Ser Pro Asp Arg Val Lys Arg Pro Met Asn Ala Phe Met Val
            420                 425                 430

Trp Ser Arg Gly Gln Arg Arg Lys Met Ala Gln Glu Asn Pro Lys Met
            435                 440                 445

His Asn Ser Glu Ile Ser Lys Arg Leu Gly Ala Glu Trp Lys Leu Leu
            450                 455                 460

Ser Glu Thr Glu Lys Arg Pro Phe Ile Asp Glu Ala Lys Arg Leu Arg
465                 470                 475                 480

Ala Leu His Met Lys Glu His Pro Asp Tyr Lys Tyr Arg Pro Arg Arg
                485                 490                 495

Lys Thr Lys Thr Leu Met Lys Lys Asp Lys Tyr Thr Leu Pro Gly Gly
            500                 505                 510

Leu Leu Ala Pro Gly Gly Asn Ser Met Ala Ser Gly Val Gly Val Gly
            515                 520                 525

Ala Gly Leu Gly Ala Gly Val Asn Gln Arg Met Asp Ser Tyr Ala His
            530                 535                 540

Met Asn Gly Trp Ser Asn Gly Ser Tyr Ser Met Met Gln Asp Gln Leu
545                 550                 555                 560

Gly Tyr Pro Gln His Pro Gly Leu Asn Ala His Gly Ala Ala Gln Met
                565                 570                 575

Gln Pro Met His Arg Tyr Asp Val Ser Ala Leu Gln Tyr Asn Ser Met
            580                 585                 590
```

```
Thr Ser Ser Gln Thr Tyr Met Asn Gly Ser Pro Thr Tyr Ser Met Ser
            595                 600                 605

Tyr Ser Gln Gln Gly Thr Pro Gly Met Ala Leu Gly Ser Met Gly Ser
    610                 615                 620

Val Val Lys Ser Glu Ala Ser Ser Pro Val Val Thr Ser Ser
625             630              635                 640

Ser His Ser Arg Ala Pro Cys Gln Ala Gly Asp Leu Arg Asp Met Ile
                645                 650                 655

Ser Met Tyr Leu Pro Gly Ala Glu Val Pro Glu Pro Ala Ala Pro Ser
            660                 665                 670

Arg Leu His Met Ser Gln His Tyr Gln Ser Gly Pro Val Pro Gly Thr
            675                 680                 685

Ala Ile Asn Gly Thr Leu Pro Leu Ser His Met Gly Ser Gly Ala Thr
            690                 695                 700

Asn Phe Ser Leu Leu Lys Gln Ala Gly Asp Val Glu Glu Asn Pro Gly
705                 710                 715                 720

Pro Met Ala Val Ser Asp Ala Leu Leu Pro Ser Phe Ser Thr Phe Ala
                725                 730                 735

Ser Gly Pro Ala Gly Arg Glu Lys Thr Leu Arg Gln Ala Gly Ala Pro
            740                 745                 750

Asn Asn Arg Trp Arg Glu Glu Leu Ser His Met Lys Arg Leu Pro Pro
            755                 760                 765

Val Leu Pro Gly Arg Pro Tyr Asp Leu Ala Ala Ala Thr Val Ala Thr
            770                 775                 780

Asp Leu Glu Ser Gly Gly Ala Gly Ala Ala Cys Gly Gly Ser Asn Leu
785                 790                 795                 800

Ala Pro Leu Pro Arg Arg Glu Thr Glu Glu Phe Asn Asp Leu Leu Asp
                805                 810                 815

Leu Asp Phe Ile Leu Ser Asn Ser Leu Thr His Pro Pro Glu Ser Val
                820                 825                 830

Ala Ala Thr Val Ser Ser Ser Ala Ser Ala Ser Ser Ser Ser Ser Pro
            835                 840                 845

Ser Ser Ser Gly Pro Ala Ser Ala Pro Ser Thr Cys Ser Phe Thr Tyr
850                 855                 860

Pro Ile Arg Ala Gly Asn Asp Pro Gly Val Ala Pro Gly Gly Thr Gly
865                 870                 875                 880

Gly Gly Leu Leu Tyr Gly Arg Glu Ser Ala Pro Pro Thr Ala Pro
            885                 890                 895

Phe Asn Leu Ala Asp Ile Asn Asp Val Ser Pro Ser Gly Gly Phe Val
            900                 905                 910

Ala Glu Leu Leu Arg Pro Glu Leu Asp Pro Val Tyr Ile Pro Pro Gln
            915                 920                 925

Gln Pro Gln Pro Pro Gly Gly Gly Leu Met Gly Lys Phe Val Leu Lys
            930                 935                 940

Ala Ser Leu Ser Ala Pro Gly Ser Glu Tyr Gly Ser Pro Ser Val Ile
945                 950                 955                 960

Ser Val Ser Lys Gly Ser Pro Asp Gly Ser His Pro Val Val Ala
                965                 970                 975

Pro Tyr Asn Gly Gly Pro Pro Arg Thr Cys Pro Lys Ile Lys Gln Glu
            980                 985                 990

Ala Val Ser Ser Cys Thr His Leu Gly Ala Gly Pro Pro Leu Ser Asn
            995                 1000                1005

Gly His Arg Pro Ala Ala His Asp Phe Pro Leu Gly Arg Gln Leu
```

```
                          1010                1015                1020
Pro Ser Arg Thr Thr Pro Thr Leu Gly Leu Glu Glu Val Leu Ser
        1025                1030                1035

Ser Arg Asp Cys His Pro Ala Leu Pro Leu Pro Pro Gly Phe His
    1040                1045                1050

Pro His Pro Gly Pro Asn Tyr Pro Ser Phe Leu Pro Asp Gln Met
1055                1060                1065

Gln Pro Gln Val Pro Pro Leu His Tyr Gln Glu Leu Met Pro Pro
    1070                1075                1080

Gly Ser Cys Met Pro Glu Glu Pro Lys Pro Lys Arg Gly Arg Arg
1085                1090                1095

Ser Trp Pro Arg Lys Arg Thr Ala Thr His Thr Cys Asp Tyr Ala
    1100                1105                1110

Gly Cys Gly Lys Thr Tyr Thr Lys Ser Ser His Leu Lys Ala His
1115                1120                1125

Leu Arg Thr His Thr Gly Glu Lys Pro Tyr His Cys Asp Trp Asp
    1130                1135                1140

Gly Cys Gly Trp Lys Phe Ala Arg Ser Asp Glu Leu Thr Arg His
1145                1150                1155

Tyr Arg Lys His Thr Gly His Arg Pro Phe Gln Cys Gln Lys Cys
    1160                1165                1170

Asp Arg Ala Phe Ser Arg Ser Asp His Leu Ala Leu His Met Lys
1175                1180                1185

Arg His Phe
    1190

<210> SEQ ID NO 10
<211> LENGTH: 47
<212> TYPE: DNA
<213> ORGANISM: Artificial sequence
<220> FEATURE:
<223> OTHER INFORMATION: Synthetic construct

<400> SEQUENCE: 10
cacacagcgg ccgcatttaa atccaccatg gcgggacacc tggcttc            47

<210> SEQ ID NO 11
<211> LENGTH: 59
<212> TYPE: DNA
<213> ORGANISM: Artificial sequence
<220> FEATURE:
<223> OTHER INFORMATION: Synthetic construct

<400> SEQUENCE: 11
agaggacgaa cgaaattgtc tctcttcaag caccgaggca aacttacgta ccctctcgg    59

<210> SEQ ID NO 12
<211> LENGTH: 66
<212> TYPE: DNA
<213> ORGANISM: Artificial sequence
<220> FEATURE:
<223> OTHER INFORMATION: Synthetic construct

<400> SEQUENCE: 12
ctctgttaaa gcaagcagga gatgttgaag aaaaccccgg gcctatgtac aacatgatgg    60
agacgg                                                              66

<210> SEQ ID NO 13
<211> LENGTH: 64
```

<212> TYPE: DNA
<213> ORGANISM: Artificial sequence
<220> FEATURE:
<223> OTHER INFORMATION: Synthetic construct

<400> SEQUENCE: 13
agaggacgaa cgaaattgtc tctcttcaag caccgaggcc tagggtacac actctccccg        60
tcac                                                                    64

<210> SEQ ID NO 14
<211> LENGTH: 63
<212> TYPE: DNA
<213> ORGANISM: Artificial sequence
<220> FEATURE:
<223> OTHER INFORMATION: Synthetic construct

<400> SEQUENCE: 14
ctctgttaaa gcaagcagga gatgttgaag aaaaccccgg gcctatggct gtcagcgacg        60
cgc                                                                     63

<210> SEQ ID NO 15
<211> LENGTH: 44
<212> TYPE: DNA
<213> ORGANISM: Artificial sequence
<220> FEATURE:
<223> OTHER INFORMATION: Synthetic construct

<400> SEQUENCE: 15
gtgtgtcagc tgtaaattta aatttttacg gagaagtaca catt                        44

<210> SEQ ID NO 16
<211> LENGTH: 44
<212> TYPE: DNA
<213> ORGANISM: Artificial sequence
<220> FEATURE:
<223> OTHER INFORMATION: Synthetic construct

<400> SEQUENCE: 16
gtgtgtcagc tgtaaattta aatttttacg gagaagtaca catt                        44

<210> SEQ ID NO 17
<211> LENGTH: 21
<212> TYPE: DNA
<213> ORGANISM: Artificial sequence
<220> FEATURE:
<223> OTHER INFORMATION: Synthetic construct

<400> SEQUENCE: 17
gattatcgga attccctcga g                                                 21

<210> SEQ ID NO 18
<211> LENGTH: 19
<212> TYPE: DNA
<213> ORGANISM: Artificial sequence
<220> FEATURE:
<223> OTHER INFORMATION: Synthetic construct

<400> SEQUENCE: 18
ccaaaggatg aagtgcaag                                                    19

<210> SEQ ID NO 19
<211> LENGTH: 20
<212> TYPE: DNA
<213> ORGANISM: Artificial sequence
<220> FEATURE:

<223> OTHER INFORMATION: Synthetic construct

<400> SEQUENCE: 19
agttttgctg caactgtacg                                             20

<210> SEQ ID NO 20
<211> LENGTH: 20
<212> TYPE: DNA
<213> ORGANISM: Artificial sequence
<220> FEATURE:
<223> OTHER INFORMATION: Synthetic construct

<400> SEQUENCE: 20
agcttgggct agagaaggat                                             20

<210> SEQ ID NO 21
<211> LENGTH: 20
<212> TYPE: DNA
<213> ORGANISM: Artificial sequence
<220> FEATURE:
<223> OTHER INFORMATION: Synthetic construct

<400> SEQUENCE: 21
tcagtttgaa tgcatgggag                                             20

<210> SEQ ID NO 22
<211> LENGTH: 19
<212> TYPE: DNA
<213> ORGANISM: Artificial sequence
<220> FEATURE:
<223> OTHER INFORMATION: Synthetic construct

<400> SEQUENCE: 22
tgcacatggc ccagcacta                                              19

<210> SEQ ID NO 23
<211> LENGTH: 20
<212> TYPE: DNA
<213> ORGANISM: Artificial sequence
<220> FEATURE:
<223> OTHER INFORMATION: Synthetic construct

<400> SEQUENCE: 23
ttctccagtt cgcagtccag                                             20

<210> SEQ ID NO 24
<211> LENGTH: 20
<212> TYPE: DNA
<213> ORGANISM: Artificial sequence
<220> FEATURE:
<223> OTHER INFORMATION: Synthetic construct

<400> SEQUENCE: 24
aacttgctgt ctgaatggag                                             20

<210> SEQ ID NO 25
<211> LENGTH: 20
<212> TYPE: DNA
<213> ORGANISM: Artificial sequence
<220> FEATURE:
<223> OTHER INFORMATION: Synthetic construct

<400> SEQUENCE: 25
tttgaggtcc tggtccatca                                             20

```
<210> SEQ ID NO 26
<211> LENGTH: 20
<212> TYPE: DNA
<213> ORGANISM: Artificial sequence
<220> FEATURE:
<223> OTHER INFORMATION: Synthetic construct

<400> SEQUENCE: 26
cagcagggac tgtcaccctg                                              20

<210> SEQ ID NO 27
<211> LENGTH: 22
<212> TYPE: DNA
<213> ORGANISM: Artificial sequence
<220> FEATURE:
<223> OTHER INFORMATION: Synthetic construct

<400> SEQUENCE: 27
ggtcacatcc actacgtggg at                                           22

<210> SEQ ID NO 28
<211> LENGTH: 20
<212> TYPE: DNA
<213> ORGANISM: Artificial sequence
<220> FEATURE:
<223> OTHER INFORMATION: Synthetic construct

<400> SEQUENCE: 28
ggagagtgcg attgcagaag                                              20

<210> SEQ ID NO 29
<211> LENGTH: 21
<212> TYPE: DNA
<213> ORGANISM: Artificial sequence
<220> FEATURE:
<223> OTHER INFORMATION: Synthetic construct

<400> SEQUENCE: 29
ggtcacatcc actacgtggg a                                            21

<210> SEQ ID NO 30
<211> LENGTH: 25
<212> TYPE: DNA
<213> ORGANISM: Artificial sequence
<220> FEATURE:
<223> OTHER INFORMATION: Synthetic construct

<400> SEQUENCE: 30
gttgttttgt tttggttttg gatat                                        25

<210> SEQ ID NO 31
<211> LENGTH: 26
<212> TYPE: DNA
<213> ORGANISM: Artificial sequence
<220> FEATURE:
<223> OTHER INFORMATION: Synthetic construct

<400> SEQUENCE: 31
atgggttgaa atattgggtt tattta                                       26

<210> SEQ ID NO 32
<211> LENGTH: 25
<212> TYPE: DNA
<213> ORGANISM: Artificial sequence
<220> FEATURE:
<223> OTHER INFORMATION: Synthetic construct
```

<400> SEQUENCE: 32
ccaccctcta accttaacct ctaac                                              25

<210> SEQ ID NO 33
<211> LENGTH: 24
<212> TYPE: DNA
<213> ORGANISM: Artificial sequence
<220> FEATURE:
<223> OTHER INFORMATION: Synthetic construct

<400> SEQUENCE: 33
gaggatgttt tttaagtttt tttt                                               24

<210> SEQ ID NO 34
<211> LENGTH: 25
<212> TYPE: DNA
<213> ORGANISM: Artificial sequence
<220> FEATURE:
<223> OTHER INFORMATION: Synthetic construct

<400> SEQUENCE: 34
aatgtttatg gtggattttg taggt                                              25

<210> SEQ ID NO 35
<211> LENGTH: 25
<212> TYPE: DNA
<213> ORGANISM: Artificial sequence
<220> FEATURE:
<223> OTHER INFORMATION: Synthetic construct

<400> SEQUENCE: 35
cccacactca tatcaatata ataac                                              25

<210> SEQ ID NO 36
<211> LENGTH: 25
<212> TYPE: DNA
<213> ORGANISM: Artificial sequence
<220> FEATURE:
<223> OTHER INFORMATION: Synthetic construct

<400> SEQUENCE: 36
gctcggtacc tttaagacca atgac                                              25

<210> SEQ ID NO 37
<211> LENGTH: 25
<212> TYPE: DNA
<213> ORGANISM: Artificial sequence
<220> FEATURE:
<223> OTHER INFORMATION: Synthetic construct

<400> SEQUENCE: 37
atgctgctag agattttcca cactg                                              25

<210> SEQ ID NO 38
<211> LENGTH: 24
<212> TYPE: DNA
<213> ORGANISM: Artificial sequence
<220> FEATURE:
<223> OTHER INFORMATION: Synthetic construct

<400> SEQUENCE: 38
tgaattgatc ccatcttgtc ttcg                                               24

<210> SEQ ID NO 39
<211> LENGTH: 22

<212> TYPE: DNA
<213> ORGANISM: Artificial sequence
<220> FEATURE:
<223> OTHER INFORMATION: Synthetic construct

<400> SEQUENCE: 39
tgctgctttt tgcttgtact gg            22

<210> SEQ ID NO 40
<211> LENGTH: 23
<212> TYPE: DNA
<213> ORGANISM: Artificial sequence
<220> FEATURE:
<223> OTHER INFORMATION: Synthetic construct

<400> SEQUENCE: 40
ttgagcaatg tggacagaga agg           23

<210> SEQ ID NO 41
<211> LENGTH: 23
<212> TYPE: DNA
<213> ORGANISM: Artificial sequence
<220> FEATURE:
<223> OTHER INFORMATION: Synthetic construct

<400> SEQUENCE: 41
gtcagaagca aatgtgagga gca           23

<210> SEQ ID NO 42
<211> LENGTH: 23
<212> TYPE: DNA
<213> ORGANISM: Artificial sequence
<220> FEATURE:
<223> OTHER INFORMATION: Synthetic construct

<400> SEQUENCE: 42
aattctggct tatcggaggc aag           23

<210> SEQ ID NO 43
<211> LENGTH: 13281
<212> TYPE: DNA
<213> ORGANISM: Artificial sequence
<220> FEATURE:
<223> OTHER INFORMATION: Synthetic construct

<400> SEQUENCE: 43
gttggaaggg ctaattcact cccaaagaag acaagatatc cttgatctgt ggatctacca    60
cacacaaggc tacttccctg attagcagaa ctacacacca gggccagggg tcagatatcc   120
actgaccttt ggatggtgct acaagctagt accagttgag ccagataagg tagaagaggc   180
caataaagga gagaacacca gcttgttaca ccctgtgagc ctgcatggga tggatgaccc   240
ggagagagaa gtgttagagt ggaggtttga cagccgccta gcatttcatc acgtggcccg   300
agagctgcat ccggagtact tcaagaactg ctgatatcga gcttgctaca agggactttc   360
cgctggggac tttccaggga ggcgtggcct gggcgggact ggggagtggc gagccctcag   420
atcctgcata taagcagctg cttttgcct gtactgggtc tctctggtta gaccagatct   480
gagcctggga gctctctggc taactaggga acccactgct taagcctcaa taaagcttgc   540
cttgagtgct tcaagtagtg tgtgcccgtc tgttgtgtga ctctggtaac tagagatccc   600
tcagaccctt ttagtcagtg tggaaaatct ctagcagtgg cgcccgaaca gggacttgaa   660
agcgaaaggg aaaccagagg agctctctcg acgcaggact cggcttgctg aagcgcgcac   720

```
ggcaagaggc gaggggcggc gactggtgag tacgccaaaa attttgacta gcggaggcta    780
gaaggagaga gatgggtgcg agagcgtcag tattaagcgg gggagaatta gatcgcgatg    840
ggaaaaaatt cggttaaggc caggggggaaa gaaaaaatat aaattaaaac atatagtatg   900
ggcaagcagg gagctagaac gattcgcagt taatcctggc ctgttagaaa catcagaagg    960
ctgtagacaa atactgggac agctacaacc atcccttcag acaggatcag aagaacttag   1020
atcattatat aatacagtag caaccctcta ttgtgtgcat caaggataga gataaaaga   1080
caccaaggaa gctttagaca agatagagga gagcaaaac aaaagtaaga ccaccgcaca   1140
gcaagcggcc gctgatcttc agacctggag gaggagatat gagggacaat ggagaagtg   1200
aattatataa atataaagta gtaaaaattg aaccattagg agtagcaccc accaaggcaa   1260
agagaagagt ggtgcagaga gaaaaagag cagtgggaat aggagctttg ttccttgggt    1320
tcttgggagc agcaggaagc actatgggcg cagcgtcaat gacgctgacg gtacaggcca   1380
gacaattatt gtctggtata gtgcagcagc agaacaattt gctgagggct attgaggcgc   1440
aacagcatct gttgcaactc acagtctggg gcatcaagca gctccaggca agaatcctgg   1500
ctgtggaaag atacctaaag gatcaacagc tcctggggat ttggggttgc tctggaaaac   1560
tcatttgcac cactgctgtg ccttggaatg ctagttggag taataaatct ctggaacaga   1620
tttggaatca cacgacctgg atggagtggg acagagaaat taacaattac acaagcttaa   1680
tacactcctt aattgaagaa tcgcaaaacc agcaagaaaa gaatgaacaa gaattattgg   1740
aattagataa atgggcaagt ttgtggaatt ggtttaacat aacaaattgg ctgtggtata   1800
taaaattatt cataatgata gtaggaggct tggtaggttt aagaatagtt tttgctgtac   1860
tttctatagt gaatagagtt aggcagggat attcaccatt atcgtttcag acccacctcc   1920
caaccccgag gggacccgac aggcccgaag gaatagaaga agaaggtgga gagagagaca   1980
gagacagatc cattcgatta gtgaacggat ctcgacggta tcgatgtcga cgataagctt   2040
tgcaaagatg gataaagttt taaacagaga ggaatctttg cagctaatgg accttctagg   2100
tcttgaaagg agtgggaatt ggctccggtg cccgtcagtg gcagagcgc acatcgccca   2160
cagtccccga aagttgggg ggagggggtcg gcaattgaac cggtgcctag agaaggtggc   2220
gcggggtaaa ctgggaaagt gatgtcgtgt actggctccg cctttttccc gagggtgggg   2280
gagaaccgta tataagtgca gtagtcgccg tgaacgttct ttttcgcaac gggtttgccg   2340
ccagaacaca ggtaagtgcc gtgtgtggtt cccgcgggcc tggcctcttt acgggttatg   2400
gcccttgcgt gccttgaatt acttccactg gctgcagtac gtgattcttg atcccgagct   2460
tcgggttgga agtgggtggg agagttcgag gccttgcgct taaggagccc cttcgcctcg   2520
tgcttgagtt gaggcctggc ctgggcgctg gggccgccgc gtgcgaatct ggtggcacct   2580
tcgcgcctgt ctcgctgctt tcgataagtc tctagccatt taaaattttt gatgacctgc   2640
tgcgacgctt ttttttctggc aagatagtct tgtaaatgcg ggccaagatc tgcacactgg   2700
tatttcggtt tttggggccg cgggcggcga cggggcccgt gcgtcccagc gcacatgttc   2760
ggcgaggcgg ggcctgcgag cgcggccacc gagaatcgga cggggtagt ctcaagctgg   2820
ccggcctgct ctggtgcctg gcctcgcgcc gccgtgtatc gccccgccct gggcggcaag   2880
gctggcccgg tcggcaccag ttgcgtgagc ggaaagatgg ccgcttcccg gccctgctgc   2940
agggagctca aaatgagga cgcggcgctc gggagagcgg gcgggtgagt cacccacaca   3000
aaggaaaagg gcctttccgt cctcagccgt cgcttcatgt gactccacgg agtaccgggc   3060
gccgtccagg cacctcgatt agttctcgag cttttggagt acgtcgtctt taggttgggg   3120
```

```
ggaggggttt tatgcgatgg agtttcccca cactgagtgg gtggagactg aagttaggcc   3180
agcttggcac ttgatgtaat tctccttgga atttgcccct tttgagtttg gatcttggtt   3240
cattctcaag cctcagacag tggttcaaag ttttttttctt ccatttcagg tgtcgtgagg  3300
aatttcgaca tttaaatcca ccatggcggg acacctggct tcggatttcg ccttctcgcc   3360
ccctccaggt ggtggaggtg atgggccagg ggggccggag ccgggctggg ttgatcctcg   3420
gacctggcta agcttccaag gccctcctgg agggccagga atcgggccgg gggttgggcc   3480
aggctctgag gtgtggggga ttcccccatg ccccccgccg tatgagttct gtgggggggat 3540
ggcgtactgt gggccccagg ttggagtggg gctagtgccc caaggcggct ggagacctc   3600
tcagcctgag ggcgaagcag gagtcggggt ggagagcaac tccgatgggg cctccccgga  3660
gccctgcacc gtcacccctg gtgccgtgaa gctggagaag gagaagctgg agcaaaaccc  3720
ggaggagtcc caggacatca aagctctgca gaaagaactc gagcaatttg ccaagctcct  3780
gaagcagaag aggatcaccc tgggatatac acaggccgat gtggggctca ccctgggggt  3840
tctatttggg aaggtattca gccaaacgac catctgccgc tttgaggctc tgcagcttag  3900
cttcaagaac atgtgtaagc tgcggccctt gctgcagaag tgggtggagg aagctgacaa  3960
caatgaaaat cttcaggaga tatgcaaagc agaaaccctc gtgcaggccc gaaagagaaa  4020
gcgaaccagt atcgagaacc gagtgagagg caacctggag aatttgttcc tgcagtgccc  4080
gaaacccaca ctgcagcaga tcagccacat cgcccagcag cttgggctcg agaaggatgt  4140
ggtccgagtg tggttctgta accggcgcca aagggcaag cgatcaagca gcgactatgc   4200
acaacgagag gattttgagg ctgctgggtc tccttctca gggggaccag tgtcctttcc   4260
tctggcccca gggcccccatt ttggtacccc aggctatggg agccctcact tcactgcact 4320
gtactcctcg gtccctttcc ctgaggggga agcctttccc cctgtctccg tcaccactct   4380
gggctctccc atgcattcaa acggatccgg agccacgaac ttctctctgt taaagcaagc   4440
aggagatgtt gaagaaaacc ccgggcctat gtacaacatg atggagacgg agctgaagcc  4500
gccgggcccg cagcaaactt cggggggcgg cggcggcaac tccaccgcgg cggcggccgg  4560
cggcaaccag aaaaacagcc cggaccgcgt caagcggccc atgaatgcct tcatggtgtg  4620
gtcccgcggg cagcggcgca agatggccca ggagaacccc aagatgcaca actcggagat  4680
cagcaagcgc ctgggcgccg agtggaaact tttgtcggag acgagaagc ggccgttcat   4740
cgacgaggct aagcggctgc gagcgctgca catgaaggag cacccggatt ataaataccg  4800
gccccggcgg aaaaccaaga cgctcatgaa gaaggataag tacacgctgc ccggcgggct  4860
gctggccccc ggcggcaata gcatggcgag cggggtcggg gtgggcgccg gctgggcgc   4920
gggcgtgaac cagcgcatgg acagttacgc gcacatgaac ggctggagca acggcagcta  4980
cagcatgatg caggaccagc tgggctaccc gcagcacccg ggcctcaatg cgcacggcgc  5040
agcgcagatg cagcccatgc accgctacga cgtgagcgcc ctgcagtaca actccatgac  5100
cagctcgcag acctacatga acggctcgcc cacctacagc atgtcctact cgcagcaggg  5160
caccccctgg catggctctt gctccatggg ttcggtggtc aagtccgagg ccagctccag  5220
ccccccctgtg gttacctctt cctcccactc cagggcgccc tgccaggccg ggacctccg   5280
ggacatgatc agcatgtatc tcccggcgc cgaggtgccg gaacccgccg ccccccagcag  5340
acttcacatg tccagcact accagagcgg cccggtgccc ggcacggcca ttaacggcac  5400
actgcccctc tcacacatgg gatccggagc cacgaacttc tctctgttaa agcaagcagg 5460
```

-continued

```
agatgttgaa gaaaacccecg ggcctatgge tgtcagcgac gcgctgctcec catctttctc    5520
cacgttcgcg tctggcccgg cgggaaggga gaagacactg cgtcaagcag gtgccccgaa    5580
taaccgctgg cgggaggagc tctcccacat gaagcgactt ccccccagtgc ttcccggccg    5640
cccctatgac ctggcggcgg cgaccgtggc cacagacctg gagagcggcg gagccggtgc    5700
ggcttgcggc ggtagcaacc tggcgcccct acctcggaga gagaccgagg agttcaacga    5760
tctcctggac ctggactttta ttctctccaa ttcgctgacc catcctccgg agtcagtggc    5820
cgccaccgtg tcctcgtcag cgtcagcctc ctcttcgtcg tcgccgtcga gcagcggccc    5880
tgccagcgcg ccctccacct gcagcttcac ctatccgatc cgggccggga acgaccgggg    5940
cgtggcgccg ggcggcacgg gcggaggcct cctctatggc agggagtccg ctcccccctcc    6000
gacggctccc ttcaacctgg cggacatcaa cgacgtgagc ccctcgggcg gcttcgtggc    6060
cgagctcctg cggccagaat tggacccggt gtacattccg ccgcagcagc cgcagccgcc    6120
aggtggcggg ctgatgggca agttcgtgct gaaggcgtcg ctgagcgccc ctggcagcga    6180
gtacggcagc ccgtcggtca tcagcgtcag caaaggcagc cctgacggca gccacccggt    6240
ggtggtggcg ccctacaacg gcgggccgcc gcgcacgtgc cccaagatca gcaggaggc    6300
ggtctcttcg tgcacccact gggcgctgg acccecteten agcaatggcc accggccggc    6360
tgcacacgac ttcccectgg ggcggcaget cccecagcagg actaccecga ccctgggtct    6420
tgaggaagtg ctgagcagca gggactgtca ccctgccctg ccgcttcctc ccggcttcca    6480
tccccaccecg gggcccaatt acccatcctt cctgcccgat cagatgcagc cgcaagtccc    6540
gccgctccat taccaagagc tcatgccacc cggttcctgc atgccagagg agcccaagcc    6600
aaagagggga agacgatcgt ggccccggaa aaggaccgcc acccacactt gtgattacgc    6660
gggctgcggc aaaacctaca caaagagttc ccatctcaag gcacacctgc gaacccacac    6720
aggtgagaaa ccttaccact gtgactggga cggctgtgga tggaaattcg cccgctcaga    6780
tgaactgacc aggcactacc gtaaacacac ggggcaccgc ccgttccagt gccaaaaatg    6840
cgaccgagca ttttccaggt cggaccacct cgccttacac atgaagaggc attttttaaat    6900
ttaaatttaa ttaatctcga cggtatcggt taacttttaa agaaaagggg gggattgggg    6960
ggtacagtgc aggggaaaga atagtagaca taatagcaac agacatacaa actaaagaat    7020
tacaaaaaca aattacaaaa attcaaaatt ttccgatcac gagactagcc tcgagggaat    7080
tccgataatc aacctctgga ttacaaaatt tgtgaaagat tgactggtat tcttaactat    7140
gttgctcctt ttacgctatg tggatacgct gctttaatgc cttttgtatca tgctattgct    7200
tcccgtatgg ctttcatttt ctcctccttg tataaatcct ggttgctgtc tctttatgag    7260
gagttgtggc ccgttgtcag gcaacgtggc gtggtgtgca ctgtgtttgc tgacgcaacc    7320
cccactggtt ggggcattgc caccacctgt cagctccttt ccgggacttt cgctttcccc    7380
ctccctattg ccacggcgga actcatcgcc gcctgcttg cccgctgctg acaggggct    7440
cggctgttgg gcactgacaa ttccgtggtg ttgtcgggga agctgacgtc ctttccatgg    7500
ctgctcgcct gtgttgccac ctggattctg cgcgggacgt ccttctgcta cgtcccttcg    7560
gccctcaatc cagcggacct tccttcccgc ggcctgctgc cggctctgcg gcctcttccg    7620
cgtcttcgcc ttcgccctca gacgagtcgg atctccecttt gggccgcctc cccgcatcgg    7680
gaattcgctc aagcttcgaa ttaattctgc agagctcggt accttttaaga ccaatgactt    7740
acaaggcagc tgtagatctt agccactttt taaaagaaaa ggggggactg gaagggctaa    7800
ttcactccca acgaagacaa gatgggatca attcaccatg gaataacctt cgtatagcat    7860
```

```
acattatacg aagttatgct gcttttgct tgtactgggt ctctctggtt agaccagatc    7920
tgagcctggg agctctctgg ctaactaggg aacccactgc ttaagcctca ataaagcttg    7980
ccttgagtgc ttcaagtagt gtgtgcccgt ctgttgtgtg actctggtaa ctagagatcc    8040
ctcagaccct tttagtcagt gtggaaaatc tctagcagca tctagaatta attccgtgta    8100
ttctatagtg tcacctaaat cgtatgtgta tgatacataa ggttatgtat taattgtagc    8160
cgcgttctaa cgacaatatg tacaagccta attgtgtagc atctggctta ctgaagcaga    8220
ccctatcatc tctctcgtaa actgccgtca gagtcggttt ggttggacga accttctgag    8280
tttctggtaa cgccgtcccg cacccggaaa tggtcagcga accaatcagc agggtcatcg    8340
ctagccagat cctctacgcc ggacgcatcg tggccggcat caccggcgcc acaggtgcgg    8400
ttgctggcgc ctatatcgcc gacatcaccg atggggaaga tcgggctcgc cacttcgggc    8460
tcatgagcgc ttgtttcggc gtgggtatgg tggcaggccc cgtggccggg ggactgttgg    8520
gcgccatctc cttgcatgca ccattccttg cggcggcggt gctcaacggc ctcaacctac    8580
tactgggctg cttcctaatg caggagtcgc ataagggaga gcgtcgaatg gtgcactctc    8640
agtacaatct gctctgatgc cgcatagtta agccagcccc gacacccgcc aacacccgct    8700
gacgcgccct gacgggcttg tctgctcccg gcatccgctt acagacaagc tgtgaccgtc    8760
tccgggagct gcatgtgtca gaggttttca ccgtcatcac cgaaacgcgc gagacgaaag    8820
ggcctcgtga tacgcctatt tttataggtt aatgtcatga taataatggt tcttagacg    8880
tcaggtggca cttttcgggg aaatgtgcgc ggaaccccta tttgtttatt tttctaaata    8940
cattcaaata tgtatccgct catgagacaa taaccctgat aaatgcttca ataatattga    9000
aaaaggaaga gtatgagtat tcaacatttc cgtgtcgccc ttattccctt ttttgcggca    9060
ttttgccttc ctgtttttgc tcacccagaa acgctggtga agtaaaaga tgctgaagat    9120
cagttgggtg cacgagtggg ttacatcgaa ctggatctca acagcggtaa gatccttgag    9180
agttttcgcc ccgaagaacg ttttccaatg atgagcactt taaagttct gctatgtggc    9240
gcggtattat cccgtattga cgccgggcaa gagcaactcg gtcgccgcat acactattct    9300
cagaatgact tggttgagta ctcaccagtc acagaaaagc atcttacgga tggcatgaca    9360
gtaagagaat tatgcagtgc tgccataacc atgagtgata acactgcggc caacttactt    9420
ctgacaacga tcggaggacc gaaggagcta accgcttttt tgcacaacat ggggatcat    9480
gtaactcgcc ttgatcgttg ggaaccggag ctgaatgaag ccataccaaa cgacgagcgt    9540
gacaccacga tgcctgtagc aatggcaaca acgttgcgca aactattaac tggcgaacta    9600
cttactctag cttcccggca acaattaata gactggatgg aggcggataa agttgcagga    9660
ccacttctgc gctcggccct tccggctggc tggtttattg ctgataaatc tggagccggt    9720
gagcgtgggt ctcgcggtat cattgcagca ctggggccag atggtaagcc ctcccgtatc    9780
gtagttatct acacgacggg gagtcaggca actatggatg aacgaaatag acagatcgct    9840
gagataggtg cctcactgat taagcattgg taactgtcag accaagttta ctcatatata    9900
ctttagattg atttaaaact tcattttaa tttaaaagga tctaggtgaa gatcctttt    9960
gataatctca tgaccaaaat cccttaacgt gagttttcgt tccactgagc gtcagacccc   10020
gtagaaaaga tcaaaggatc ttcttgagat cctttttttc tgcgcgtaat ctgctgcttg   10080
caaacaaaaa aaccaccgct accagcggtg gtttgtttgc cggatcaaga gctaccaact   10140
ctttttccga aggtaactgg cttcagcaga gcgcagatac caaatactgt ccttctagtg   10200
```

-continued

```
tagccgtagt taggccacca cttcaagaac tctgtagcac cgcctacata cctcgctctg   10260
ctaatcctgt taccagtggc tgctgccagt ggcgataagt cgtgtcttac cgggttggac   10320
tcaagacgat agttaccgga taaggcgcag cggtcgggct gaacgggggg ttcgtgcaca   10380
cagcccagct tggagcgaac gacctacacc gaactgagat acctacagcg tgagcattga   10440
gaaagcgcca cgcttcccga agggagaaag gcggacaggt atccggtaag cggcagggtc   10500
ggaacaggag agcgcacgag ggagcttcca gggggaaacg cctggtatct ttatagtcct   10560
gtcgggtttc gccacctctg acttgagcgt cgattttttgt gatgctcgtc aggggggcgg   10620
agcctatgga aaaacgccag caacgcggcc ttttttacggt tcctggcctt ttgctggcct   10680
tttgctcaca tgttctttcc tgcgttatcc cctgattctg tggataaccg tattaccgcc   10740
tttgagtgag ctgataccgc tcgccgcagc cgaacgaccg agcgcagcga gtcagtgagc   10800
gaggaagcgg aagagcgccc aatacgcaaa ccgcctctcc ccgcgcgttg gccgattcat   10860
taatgcagct gtggaatgtg tgtcagttag ggtgtggaaa gtccccaggc tccccagcag   10920
gcagaagtat gcaaagcatg catctcaatt agtcagcaac caggtgtgga agtccccag   10980
gctcccagc aggcagaagt atgcaaagca tgcatctcaa ttagtcagca accatagtcc   11040
cgcccctaac tccgcccatc ccgcccctaa ctccgcccag ttccgcccat tctccgcccc   11100
atggctgact aatttttttt atttatgcag aggccgaggc cgcctcggcc tctgagctat   11160
tccagaagta gtgaggaggc ttttttggag gcctaggctt ttgcaaaaag cttgacaca   11220
agacaggctt gcgagatatg tttgagaata ccactttatc ccgcgtcagg gagaggcagt   11280
gcgtaaaaag acgcggactc atgtgaaata ctggttttta gtgcgccaga tctctataat   11340
ctcgcgcaac ctattttccc ctcgaacact ttttaagccg tagataaaca ggctgggaca   11400
cttcacatga gcgaaaaata catcgtcacc tgggacatgt tgcagatcca tgcacgtaaa   11460
ctcgcaagcc gactgatgcc ttctgaacaa tggaaaggca ttattgccgt aagccgtggc   11520
ggtctgtacc gggtgcgtta ctggcgcgtg aactgggtat tcgtcatgtc gataccgttt   11580
gtatttccag ctacgatcac gacaaccagc gcgagcttaa agtgctgaaa cgcgcagaag   11640
gcgatggcga aggcttcatc gttattgatg acctggtgga taccggtggt actgcggttg   11700
cgattcgtga atgtatcca aaagcgcact tgtcaccat cttcgcaaaa ccggctggtc   11760
gtccgctggt tgatgactat gttgttgata tcccgcaaga tacctggatt gaacagccgt   11820
gggatatggg cgtcgtattc gtcccgccaa tctccggtcg ctaatctttt caacgcctgg   11880
cactgccggg cgttgttctt tttaacttca ggcgggttac aatagtttcc agtaagtatt   11940
ctggaggctg catccatgac acaggcaaac ctgagcgaaa ccctgttcaa accccgcttt   12000
aaacatcctg aaacctcgac gctagtccgc cgctttaatc acggcgcaca accgcctgtg   12060
cagtcggccc ttgatggtaa aaccatccct cactggtatc gcatgattaa ccgtctgatg   12120
tggatctggc gcggcattga cccacgcgaa atcctcgacg tccaggcacg tattgtgatg   12180
agcgatgccg aacgtaccga cgatgattta cgatacgg tgattggcta ccgtggcggc   12240
aactggattt atgagtgggc cccggatctt tgtgaaggaa ccttacttct gtggtgtgac   12300
ataattggac aaactaccta cagagattta aagctctaag gtaaatataa aattttttaag   12360
tgtataatgt gttaaactac tgattctaat tgtttgtgta ttttagattc caacctatgg   12420
aactgatgaa tgggagcagt ggtggaatgc ctttaatgag gaaaacctgt tttgctcaga   12480
agaaatgcca tctagtgatg atgaggctac tgctgactct caacattcta ctcctccaaa   12540
aaagaagaga aaggtagaag accccaagga cttttccttca gaattgctaa gtttttttgag   12600
```

```
tcatgctgtg tttagtaata gaactcttgc ttgctttgct atttacacca caaaggaaaa    12660
agctgcactg ctatacaaga aaattatgga aaaatattct gtaaccttta taagtaggca    12720
taacagttat aatcataaca tactgttttt tcttactcca cacaggcata gagtgtctgc    12780
tattaataac tatgctcaaa aattgtgtac ctttagcttt ttaatttgta aaggggttaa    12840
taaggaatat ttgatgtata gtgccttgac tagagatcat aatcagccat accacatttg    12900
tagaggtttt acttgcttta aaaaacctcc cacacctccc cctgaacctg aaacataaaa    12960
tgaatgcaat tgttgttgtt aacttgttta ttgcagctta taatggttac aaataaagca    13020
atagcatcac aaatttcaca ataaaagcat ttttttcact gcattctagt tgtggtttgt    13080
ccaaactcat caatgtatct tatcatgtct ggatcaactg gataactcaa gctaaccaaa    13140
atcatcccaa acttcccacc ccatacccta ttaccactgc caattaccta gtggtttcat    13200
ttactctaaa cctgtgattc ctctgaatta ttttcatttt aaagaaattg tatttgttaa    13260
atatgtacta caaacttagt a                                             13281

<210> SEQ ID NO 44
<211> LENGTH: 21697
<212> TYPE: DNA
<213> ORGANISM: Artificial sequence
<220> FEATURE:
<223> OTHER INFORMATION: Synthetic construct

<400> SEQUENCE: 44
cgggaagcgt ggcgctttct catagctcac gctgtaggta tctcagttcg gtgtaggtcg      60
ttcgctccaa gctgggctgt gtgcacgaac ccccgttca gcccgaccgc tgcgccttat     120
ccggtaacta tcgtcttgag tccaacccgg taagacacga cttatcgcca ctggcagcag    180
ccactggtaa caggattagc agagcgaggt atgtaggcgg tgctacagag ttcttgaagt    240
ggtggcctaa ctacggctac actagaagga cagtatttgg tatctgcgct ctgctgaagc    300
cagttacctt cggaaaaaga gttggtagct cttgatccgg caaacaaacc accgctggta    360
gcggtggttt ttttgtttgc aagcagcaga ttacgcgcag aaaaaaagga tctcaagaag    420
atcctttgat cttttctacg gggtctgacg ctcagtggaa cgaaaactca cgttaaggga    480
ttttggtcat gagattatca aaaaggatct tcacctagat ccttttaaat taaaaatgaa    540
gttttaaatc aatctaaagt atatatgagt aaacttggtc tgacagttac caatgcttaa    600
tcagtgaggc acctatctca gcgatctgtc tatttcgttc atccatagtt gcctgactcc    660
ccgtcgtgta gataactacg atacgggagg gcttaccatc tggccccagt gctgcaatga    720
taccgcgaga cccacgctca ccggctccag atttatcagc aataaaccag ccagccggaa    780
gggccgagcg cagaagtggt cctgcaactt tatccgcctc catccagtct attaattgtt    840
gccgggaagc tagagtaagt agttcgccag ttaatagttt gcgcaacgtt gttgccattg    900
ctacaggcat cgtggtgtca cgctcgtcgt ttggtatggc ttcattcagc tccggttccc    960
aacgatcaag gcgagttaca tgatccccca tgttgtgcaa aaaagcggtt agctccttcg    1020
gtcctccgat cgttgtcaga agtaagttgg ccgcagtgtt atcactcatg gttatggcag    1080
cactgcataa ttctcttact gtcatgccat ccgtaagatg cttttctgtg actggtgagt    1140
actcaaccaa gtcattctga gaatagtgta tgcggcgacc gagttgctct tgcccggcgt    1200
caatacggga taataccgcg ccacatagca gaactttaaa agtgctcatc attggaaaac    1260
gttcttcggg gcgaaaactc tcaaggatct taccgctgtt gagatccagt tcgatgtaac    1320
```

```
ccactcgtgc acccaactga tcttcagcat ctttttacttt caccagcgtt tctgggtgag   1380
caaaaacagg aaggcaaaat gccgcaaaaa agggaataag ggcgacacgg aaatgttgaa   1440
tactcatact cttccttttt caatattatt gaagcattta tcagggttat tgtctcatga   1500
gcggatacat atttgaatgt atttagaaaa ataaacaaat aggggttccg cgcacatttc   1560
cccgaaaagt gccacctaaa ttgtaagcgt taatattttg ttaaaattcg cgttaaattt   1620
ttgttaaatc agctcatttt ttaaccaata ggccgaaatc ggcaaaatcc cttataaatc   1680
aaaagaatag accgagatag ggttgagtgt tgttccagtt tggaacaaga gtccactatt   1740
aaagaacgtg gactccaacg tcaaagggcg aaaaaccgtc tatcagggcg atggcccact   1800
acgtgaacca tcaccctaat caagtttttt ggggtcgagg tgccgtaaag cactaaatcg   1860
gaaccctaaa gggagccccc gatttagagc ttgacgggga agccggcga acgtggcgag   1920 aaaggaaggg aagaaagcga aaggagcggg cgctagggcg ctggcaagtg tagcggtcac   1980
gctgcgcgta accaccacac ccgccgcgct taatgcgccg ctacagggcg cgtcccattc   2040
gccattcagg ctgcgcaact gttgggaagg gcgatcggtg cgggcctctt cgctattacg   2100
ccagctggcg aaagggggat gtgctgcaag gcgattaagt tgggtaacgc cagggttttc   2160
ccagtcacga cgttgtaaaa cgacggccag tgaattgtaa tacgactcac tatagggcga   2220
attgggtacc gggccccccc tcgagcagtg tggttttcaa gaggaagcaa aaagcctctc   2280
cacccaggcc tggaatgttt ccacccaatg tcgagcagtg tggtttgca agaggaagca   2340 aaaagcctct ccacccaggc ctggaatgtt tccacccaat gtcgagcaaa ccccgcccag   2400
cgtcttgtca ttggcgaatt cgaacacgca gatgcagtcg gggcggcgcg gtccgaggtc   2460
cacttcgcat attaaggtga cgcgtgtggc ctcgaacacc gagcgaccct gcagcgaccc   2520
gcttaacagc gtcaacagcg tgccgcagat cttggtggcg tgaaactccc gcacctcttc   2580
ggccagcgcc ttgtagaagc gcgtatggct tcgtaccccg gccatcaaca cgcgtctgcg   2640
ttcgaccagg ctgcgcgttc tcgcggccat agcaaccgac gtacggcgtt gcgcctcgc   2700 cggcagcaag aagccacgga agtccgcccg gagcagaaaa tgcccacgct actgcgggtt   2760
tatatagacg gtccccacgg gatggggaaa accaccacca cgcaactgct ggtggccctg   2820
ggttcgcgcg acgatatcgt ctacgtaccc gagccgatga cttactggcg ggtgctgggg   2880
gcttccgaga caatcgcgaa catctacacc acacaacacc gcctcgacca gggtgagata   2940
tcggccgggg acgcggcggt ggtaatgaca agcgcccaga taacaatggg catgccttat   3000
gccgtgaccg acgccgttct ggctcctcat atcgggggg aggctgggag ctcacatgcc   3060 ccgccccgg ccctcaccct catcttcgac cgccatccca tcgccgccct cctgtgctac   3120
ccggccgcgc ggtaccttat gggcagcatg accccccagg ccgtgctggc gttcgtggcc   3180
ctcatcccgc cgaccttgcc cggcaccaac atcgtgcttg ggcccttcc ggaggacaga   3240 cacatcgacc gcctggccaa acgccagcgc cccggcgagc ggctggacct ggctatgctg   3300
gctgcgattc gccgcgttta cggctactt gccaatacgg tgcggtatct gcagtgcggc   3360
gggtcgtggc gggaggactg gacagctt cggggacgg ccgtgccgcc caggtgcc   3420 gagccccaga gcaacgcggg cccacgaccc catatcgggg acacgttatt taccctgttt   3480
cgggcccccg agttgctggc ccccaacggc gacctgtata acgtgtttgc ctgggccttg   3540
gacgtcttgg ccaaacgcct ccgttccatg cacgtcttta tcctggatta cgaccaatcg   3600
cccgccggct gccgggacgc cctgctgcaa cttacctccg ggatggtcca gacccacgtc   3660 accaccccg gctccatacc gacgatatgc gacctggcgc gcacgtttgc ccgggagatg   3720
```

```
ggggaggcta actgaaacac ggaaggagac aataccggaa ggaacccgcg ctatgacggc    3780
aataaaaaga cagaataaaa cgcacgggtg ttgggtcgtt tgttcataaa cgcggggttc    3840
ggtcccaggg ctggcactct gtcgataccc caccgagacc ccattggggc caatacgccc    3900
gcgtttcttc cttttcccca ccccacccc caagttcggg tgaaggccca gggctcgcag    3960
ccaacgtcgg ggcggcaggc cctgccatag ccactggccc cgtgggttag ggacggggtc    4020
ccccatgggg aatggtttat ggttcgtggg ggttattatt ttgggcgttg cgtgggtca    4080 ggtccacgac cctaagcttg atatcgaatt cctgcagccc ggggatcct cctccttcct    4140 ttgcctgcac attgtagccc ataatactat accccatcaa gtgttcctgc tccaagaaat    4200
agcttcctcc tcttacttgc cccagaacat ctctgtaaag aatttcctct tatcttccca    4260
tatttcagtc aagattcatt gctcacgtat tacttgtgac ctctcttgac cccagccaca    4320
ataaacttct ctatactacc caaaaaatct ttccaaaccc tccccgacac catattttta    4380
tatttttctt atttatttca tgcacacaca cacactccgt gctttataag caattctgcc    4440
tattctctac cttcttacaa tgcctactgt gcctcatatt aaattcatca atgggcagaa    4500
agaaaatatt tattcaagaa aacagtgaat gaatgaacga atgagtaaat gagtaaatga    4560
aggaatgatt attccttgct ttagaacttc tggaattaga ggacaatatt aataatacca    4620
tcgcacagtg tttctttgtt gttaatgcta caacatacaa agaggaagca tgcagtaaac    4680
aaccgaacag ttatttcctt tctgatcata ggagtaatat ttttttcctt gagcacattt    4740
ttgccatagg taaaattaga aggattttta gaactttctc agttgtatac atttttaaaa    4800
atctgtatta tatgcatgtt gattaatttt aaacttactt gaatacctaa acagaatctg    4860
ttgtttcctt gtgtttgaaa gtgctttcac agtaactctg tctgtactgc cagaatatac    4920
tgacaatgtg ttatagttaa ctgttttgat cacaacattt tgaattgact ggcagcagaa    4980
gctcttttta tatccatgtg ttttccttaa gtcattatac atagtaggca tgagactctt    5040
tatactgaat aagatattta ggaaccactg gtttacatat cagaagcaga gctactcagg    5100
gcatttgggg gaagatcact ttcacattcc tgagcatagg gaagttctca taagagtaag    5160
atattaaaag gagatacttg tgtggtattc gaaagacagt aagagagatt gtagaccta    5220 tgatcttgat agggaaaaca aactacattc ctttctccaa aagtcaaaaa aaaagagcaa    5280
atatagctta ctataccttc tattcctaca ccattagaag tagtcagtga gtctaggcaa    5340
gatgttggcc ctaaaaatcc aaataccaga gaattcatga gaacatcacc tggatgggac    5400
atgtgccgag caacacaatt actatatgct aggcattgct atcttcatat tgaagatgag    5460
gaggtcaaga gatgaaaaaa gacttggcac cttgttgtta tattaaaatt atttgttaga    5520
gtagagcttt tgtaagagtc taggagtgtg ggagctaaat gatgatacac atggacacaa    5580
agaatagatc aacagacacc caggcctact tgagggttga gggtgggaag agggagacga    5640
tgaaaaagaa cctattgggt attaagttca tcactgagtg atgaaataat ctgtacatca    5700
agacccagtg atatgcaatt tacctatata acttgtacat gtaccccaa atttaaaata    5760 aagttaaaac aaagtatagg aatggaatta attcctcaag atttggcttt aattttattt    5820
gataatttat caaatggttg ttttctttt ctcactatgg cgttgcttta taaactatgt    5880
tcagtatgtc tgaatgaaag ggtgtgtgtg tgtgtgaaag agagggagag aggaagggaa    5940
gagaggacga ataatgtgaa atttgagttc atgaaaattt ttcaataaaa taatttaatg    6000
tcaggagaat taagcctaat agtctcctaa atcatccatc tcttgagctt cagagcagtc    6060
```

```
ctctgaatta atgcctacat gtttgtaaag ggtgttcaga ctgaagccaa gattctacct    6120
ctaaagagat gcaatctcaa atttatctga agactgtacc tctgctctcc ataaattgac    6180
accatggccc acttaatgag gttaaaaaaa agctaattct gaatgaaaat ctgagcccag    6240
tggaggaaat attaatgaac aaggtgcaga ctgaaatata aattttctgt aataattatg    6300
catatacttt agcaaagttc tgtctatgtt gactttattg cttttggtaa gaaatacaac    6360
tttttaaagt gaactaaact atcctatttc caaactattt tgtgtgtgtg cggtttgttt    6420
ctatgggttc tggttttctt ggagcatttt tatttcattt taattaatta attctgagag    6480
ctgctgagtt gtgtttactg agagattgtg tatctgcgag agaagtctgt agcaagtagc    6540
tagactgtgc ttgacctagg aacatataca gtagattgct aaaatgtctc acttggggaa    6600
ttttagacta acagtagag catgtataaa aatactctag tcaagtgctg cttttgaaac    6660
aaatgataaa accacactcc catagatgag tgtcatgatt ttcatggagg aagttaatat    6720
tcatcctcta agtataccca gactagggcc attctgatat aaaacattag gacttaagaa    6780
agattaatag actggagtaa aggaaatgga cctctgtctc tctcgctgtc tcttttttga    6840
ggacttgtgt gtgtgtgtgt gtgtgtgtgt gtgtgtgttg tggtcagtgg ggctggaata    6900
aaagtagaat agacctgcac ctgctgtggc atccattcac agagtagaag caagctcaca    6960
atagtgaaga tgtcagtaag cttgaatagt ttttcaggaa ctttgaatgc tgatttagat    7020
ttgaaactga ggctctgacc ataaccaaat ttgcactatt tattgcttct tgaaacttat    7080
ttgcctggta tgcctgggct tttgatggtc ttagtatagc ttgcagcctt gtccctgcag    7140
ggtattatgg gtaatagaaa gaaagtctg cgttacactc tagtcacact aagtaactac    7200
cattggaaaa gcaacccctg ccttgaagcc aggatgatgg tatctgcagc agttgccaac    7260
acaagagaag gatccatagt tcatcattta aaaagaaaa caaatagaa aaggaaaac     7320
tatttctgag cataagaagt tgtagggtaa gtctttaaga aggtgacaat ttctgccaat    7380
caggatttca aagctcttgc tttgacaatt ttggtctttc agaatactat aaatataacc    7440
tatattataa tttcataaag tctgtgcatt ttctttgacc caggatattt gcaaaagaca    7500
tattcaaact tccgcagaac actttatttc acatatacat gcctcttata tcagggatgt    7560
gaaacagggt cttgaaaact gtctaaatct aaaacaatgc taatgcaggt ttaaatttaa    7620
taaaataaaa tccaaaatct aacagccaag tcaaatctgt atgttttaac atttaaaata    7680
ttttaaagac gtcttttccc aggattcaac atgtgaaatc ttttctcagg gatacacgtg    7740
tgcctagatc ctcattgctt tagttttttta cagaggaatg aatataaaaa gaaaatactt    7800
aaattttatc cctcttacct ctataatcat acataggcat aattttttaa cctaggctcc    7860
agatagccat agaagaacca aacactttct gcgtgtgtga gaataatcag agtgagattt    7920
tttcacaagt acctgatgag ggttgagaca ggtagaaaaa gtgagagatc tctatttatt    7980
tagcaataat agaaaagca tttaagaaa taaagcaatg gaaataagaa atttgtaaat    8040
ttccttctga taactagaaa tagaggatcc agtttctttt ggttaaccta aattttattt    8100
cattttattg ttttatttta ttttatttta tttatttttg tgtaatcgta gtttcagagt    8160
gttagagctg aaaggaagaa gtaggagaaa catgcaaagt aaaagtataa cactttcctt    8220
actaaaccga ctgggtttcc aggtaggggc aggattcagg atgactgaca gggcccttag    8280
ggaacactga gacccctacgc tgacctcata aatgcttgct accttgctg ttttaattac    8340
atcttttaat agcaggaagc agaactctgc acttcaaaag ttttcctca cctgaggagt     8400
taatttagta caaggggaaa aagtacaggg ggatgggaga aaggcgatca cgttgggaag    8460
```

```
ctatagagaa agaagagtaa attttagtaa aggaggttta aacaaacaaa atataaagag    8520
aaataggaac ttgaatcaag gaaatgattt taaaacgcag tattcttagt ggactagagg    8580
aaaaaaataa tctgagccaa gtagaagacc ttttcccctc ctacccctac tttctaagtc    8640
acagaggctt tttgttcccc cagacactct tgcagattag tccaggcaga aacagttaga    8700
tgtccccagt taacctccta tttgacacca ctgattaccc cattgatagt cacactttgg    8760
gttgtaagtg actttttatt tatttgtatt tttgactgca ttaagaggtc tctagttttt    8820
tatctcttgt ttcccaaaac ctaataagta actaatgcac agagcacatt gatttgtatt    8880
tattctatt ttagacataa tttattagca tgcatgagca aattaagaaa aacaacaaca     8940
aatgaatgca tatatatgta tatgtatgtg tgtatatata cacatatata tatatatttt    9000
ttttctttc ttaccagaag gttttaatcc aaataaggag aagatatgct tagaactgag     9060
gtagagtttt catccattct gtcctgtaag tattttgcat attctggaga cgcaggaaga    9120
gatccatcta catatcccaa agctgaatta tggtagacaa agctcttcca cttttagtgc    9180
atcaatttct tatttgtgta ataagaaaat tgggaaaacg atcttcaata tgcttaccaa    9240
gctgtgattc caaatattac gtaaatacac ttgcaaagga ggatgttttt agtagcaatt    9300
tgtactgatg gtatggggcc aagagatata tcttagaggg agggctgagg gtttgaagtc    9360
caactcctaa gccagtgcca gaagagccaa ggacaggtac ggctgtcatc acttagacct    9420
caccctgtgg agccacaccc tagggttggc caatctactc ccaggagcag ggagggcagg    9480
agccagggct gggcataaaa gtcagggcag agccatctat tgcttacatt tgcttctgac    9540
acaactgtgt tcactagcaa cctcaaacag acaccatggt gcacctgact cctgaggaga    9600
agtctgccgt tactgccctg tggggcaagg tgaacgtgga tgaagttggt ggtgaggccc    9660
tgggcaggtt ggtatcaagg ttacaagaca ggtttaagga gaccaataga aactgggcat    9720
gtggagacag agatagtgga tccataactt cgtatagcat acattatacg aagttatgtc    9780
gacactagtg tcgagtcgcc gattaagtac tgtcgagtcg ccgattaagt actgtcgagt    9840
cgccgattaa gtactgtcga gtcgccgatt aagtactgtc gagtcgccga ttaagtactg    9900
tcgagccgag gtccacttcg catattaagg tgacgcgtgt ggcctcgaac accgagcgac    9960
cctgcagcga cccgcttaac ctgcagggcc gccaccatgg ccaatttact gaccgtacac   10020
caaaatttgc ctgcattacc ggtcgatgca acgagtgatg aggttcgcaa gaacctgatg   10080
gacatgttca gggatcgcca ggcgttttct gagcatacct ggaaaatgct tctgtccgtt   10140
tgccggtcgt gggcggcatg gtgcaagttg aataaccgga aatggtttcc cgcagaacct   10200
gaagatgttc gcgattatct tctatatctt caggcgcgcg gtctggcagt aaaaactatc   10260
cagcaacatt gggccagct aaacatgctt catcgtcggt ccgggctgcc acgaccaagt    10320
gacagcaatg ctgtttcact ggttatgcgg cggatccgaa agaaaacgt tgatgccggt     10380
gaacgtgcaa aacaggctct agcgttcgaa cgcactgatt tcgaccaggt tcgttcactc   10440
atggaaaata gcgatcgctg ccaggatata cgtaatctgg catttctggg gattgcttat   10500
aacaccctgt tacgtatagc cgaaattgcc aggatcaggg ttaaagatat ctcacgtact   10560
gacggtggga gaatgttaat ccatattggc agaacgaaaa cgctggttag caccgcaggt   10620
gtagagaagg cacttagcct gggggtaact aaactggtcg agcgatggat tccgtctct    10680
ggtgtagctg atgatccgaa taactacctg ttttgccggg tcagaaaaaa tggtgttgcc   10740
gcgccatctg ccaccagcca gctatcaact cgcgccctgg aagggatttt tgaagcaact   10800
```

```
catcgattga tttacggcgc taaggatgac tctggtcaga gatacctggc ctggtctgga   10860
cacagtgccc gtgtcggagc cgcgcgagat atggcccgcg ctggagtttc aataccggag   10920
atcatgcaag ctggtggctg gaccaatgta aatattgtca tgaactatat ccgtaacctg   10980
gatagtgaaa cagggggcaat ggtgcgcctg ctggaagatg cgatggacc ggtcgccacc   11040 atggtgagca agggcgagga gctgttcacc ggggtggtgc ccatcctggt cgagctggac   11100
ggcgacgtaa acggccacaa gttcagcgtg tccggcgagg gcgagggcga tgccacctac   11160
ggcaagctga ccctgaagtt catctgcacc accggcaagc tgcccgtgcc ctggcccacc   11220
ctcgtgacca ccctgaccta cggcgtgcag tgcttcagcc gctacccga ccacatgaag   11280 cagcacgact tcttcaagtc cgccatgccc gaaggctacg tccaggagcg caccatcttc   11340
ttcaaggacg acggcaacta caagacccgc gccgaggtga agttcgaggg cgacaccctg   11400
gtgaaccgca tcgagctgaa gggcatcgac ttcaaggagg acggcaacat cctggggcac   11460
aagctggagt acaactacaa cagccacaac gtctatatca tggccgacaa gcagaagaac   11520
ggcatcaagg tgaacttcaa gatccgccac aacatcgagg acggcagcgt gcagctcgcc   11580
gaccactacc agcagaacac ccccatcggc gacggccccg tgctgctgcc cgacaaccac   11640
tacctgagca cccagtccgc cctgagcaaa gaccccaacg agaagcgcga tcacatggtc   11700
ctgctggagt tcgtgaccgc cgccgggatc actctcggca tggacgagct gtacaagtaa   11760
catatgctcg acgataagct tgcaaagat ggataaagtt ttaaacagag aggaatcttt   11820
gcagctaatg gaccttctag gtcttgaaag gagtgggaat tggctccggt gcccgtcagt   11880
gggcagagcg cacatcgccc acagtccccg agaagttggg gggagggtc ggcaattgaa   11940 ccggtgccta gagaaggtgg cgcggggtaa actgggaaag tgatgtcgtg tactggctcc   12000 gccttttcc cgagggtggg ggagaaccgt atataagtgc agtagtcgcc gtgaacgttc   12060
tttttcgcaa cgggtttgcc gccagaacac aggtaagtgc cgtgtgtggt tcccgcgggc   12120
ctggcctctt tacgggttat ggcccttgcg tgccttgaat tacttccact ggctgcagta   12180
cgtgattctt gatcccgagc ttcgggttgg aagtgggtgg gagagttcga ggccttgcgc   12240
ttaaggagcc ccttcgcctc gtgcttgagt tgaggcctgg cctgggcgct ggggccgccg   12300
cgtgcgaatc tggtggcacc ttcgcgcctg tctcgctgct ttcgataagt ctctagccat   12360
ttaaaatttt tgatgacctg ctgcgacgct ttttttctgg caagatagtc ttgtaaatgc   12420
gggccaagat ctgcacactg gtatttcggt ttttggggcc gcgggcggcg acggggcccg   12480
tgcgtcccag cgcacatgtt cggcgaggcg gggcctgcga gcgcggccac cgagaatcgg   12540 acggggtag tctcaagctg gccggcctgc tctggtgcct ggcctcgcgc cgccgtgtat   12600
cgccccgccc tgggcggcaa ggctggcccg gtcggcacca gttgcgtgag cggaaagatg   12660
gccgcttccc ggccctgctg cagggagctc aaaatggagg acgcggcgct cgggagagcg   12720
ggcgggtgag tcacccacac aaaggaaaag ggcctttccg tcctcagccg tcgcttcatg   12780
tgactccacg gagtaccggg cgccgtccag gcacctcgat tagttctcga cttttggag   12840 tacgtcgtct ttaggttggg gggagggggtt ttatgcgatg gagtttcccc acactgagtg   12900
ggtggagact gaagttaggc cagcttggca cttgatgtaa ttctccttgg aatttgccct   12960
ttttgagttt ggatcttggt tcattctcaa gcctcagaca gtggttcaaa gttttttct   13020 tccattcag gtgtcgtgag gaatttcgac atttaaatcc accatggcgg acacctggc   13080 ttcgatttc gccttctcgc cccctccagg tggtggaggt gatgggccag gggggccgga   13140
gccgggctgg gttgatcctc ggacctggct aagcttccaa ggccctcctg gagggccagg   13200
```

```
aatcgggccg ggggttgggc caggctctga ggtgtggggg attccccat gccccccgcc   13260
gtatgagttc tgtgggggga tggcgtactg tgggcccag gttggagtgg ggctagtgcc   13320
ccaaggcggc ttggagacct ctcagcctga gggcgaagca ggagtcgggg tggagagcaa   13380
ctccgatggg gcctccccgg agccctgcac cgtcacccct ggtgccgtga agctggaaa    13440
ggagaagctg gagcaaaacc cggaggagtc ccaggacatc aaagctctgc agaaagaact   13500
cgagcaattt gccaagctcc tgaagcagaa gaggatcacc ctgggatata cacaggccga   13560
tgtgggctc accctggggg ttctatttgg gaaggtattc agccaaacga ccatctgccg    13620
ctttgaggct ctgcagctta gcttcaagaa catgtgtaag ctgcggccct tgctgcagaa   13680
gtgggtggag gaagctgaca acaatgaaaa tcttcaggag atatgcaaag cagaaaccct   13740
cgtgcaggcc cgaaagagaa agcgaaccag tatcgagaac cgagtgagag gcaacctgga   13800
gaatttgttc ctgcagtgcc cgaaacccac actgcagcag atcagccaca tcgcccagca   13860
gcttgggctc gagaaggatg tggtccgagt gtggttctgt aaccggcgcc agaagggcaa   13920
gcgatcaagc agcgactatg cacaacgaga ggattttgag gctgctgggt ctcctttctc   13980
aggggggacca gtgtccttc ctctggcccc agggccccat tttggtaccc caggctatgg    14040
gagccctcac ttcactgcac tgtactcctc ggtccctttc cctgagggg aagcctttcc     14100
ccctgtctcc gtcaccactc tgggctctcc catgcattca aacggatccg gagccacgaa   14160
cttctctctg ttaaagcaag caggagatgt tgaagaaaac cccgggccta tgtacaacat   14220
gatggagacg gagctgaagc cgccgggccc gcagcaaact tcggggggcg gcggcggcaa   14280
ctccaccgcg gcggcggccg gcggcaacca gaaaaacagc ccggaccgcg tcaagcggcc   14340
catgaatgcc ttcatggtgt ggtcccgcgg gcagcggcgc aagatggccc aggagaaccc   14400
caagatgcac aactcggaga tcagcaagcg cctgggcgcc gagtggaaac ttttgtcgga   14460
gacggagaag cggccgttca tcgacgaggc taagcggctg cgagcgctgc acatgaagga   14520
gcacccggat tataaatacc ggccccggcg gaaaaccaag acgctcatga agaaggataa   14580
gtacacgctg cccggcgggc tgctggcccc cggcggcaat agcatggcga gcggggtcgg   14640
ggtgggcgcc ggcctgggcg cgggcgtgaa ccagcgcatg gacagttacg cgcacatgaa   14700
cggctggagc aacggcagct acagcatgat gcaggaccag ctgggctacc cgcagcaccc   14760
gggcctcaat gcgcacggcg cagcgcagat gcagcccatg caccgctacg acgtgagcgc   14820
cctgcagtac aactccatga ccagctcgca gacctacatg aacggctcgc ccacctacag   14880
catgtcctac tcgcagcagg gcaccctgg catggctctt ggctccatgg gttcggtggt    14940
caagtccgag gccagctcca gcccccctgt ggttacctct tcctcccact ccagggcgcc   15000
ctgccaggcc gggaccctcc gggacatgat cagcatgtat ctccccggcg ccgaggtgcc   15060
ggaacccgcc gcccccagca gacttcacat gtcccagcac taccagagcg gcccggtgcc   15120
cggcacggcc attaacggca cactgccccct ctcacacatg ggatccggag ccacgaactt   15180
ctctctgtta aagcaagcag gagatgttga agaaaacccc gggcctatgg ctgtcagcga   15240
cgcgctgctc ccatctttct ccacgttcgc gtctggcccg gcgggaaggg agaagacact   15300
gcgtcaagca ggtgccccga ataaccgctg gcggagga ctctcccaca tgaagcgact     15360
tcccccagtg cttcccggcc gccctatga cctggcggcg gcgaccgtgg ccacagacct   15420
ggagagcggc ggagccggtg cggcttgcgg cggtagcaac ctggcgcccc tacctcggag   15480
agagaccgag gagttcaacg atctcctgga cctggacttt attctctcca attcgctgac   15540
```

-continued

```
ccatcctccg gagtcagtgg ccgccaccgt gtcctcgtca gcgtcagcct cctcttcgtc   15600
gtcgccgtcg agcagcggcc ctgccagcgc gccctccacc tgcagcttca cctatccgat   15660
ccgggccggg aacgacccgg gcgtggcgcc gggcggcacg ggcggaggcc tcctctatgg   15720
cagggagtcc gctcccccte cgacggctcc cttcaacctg gcggacatca acgacgtgag   15780
cccctcgggc ggcttcgtgg ccgagctcct gcggccagaa ttggaccegg tgtacattcc   15840 gccgcagcag ccgcagccgc caggtggcgg gctgatgggc aagttcgtgc tgaaggcgtc   15900
gctgagcgcc cctggcagcg agtacggcag cccgtcggtc atcagcgtca gcaaaggcag   15960
ccctgacggc agccacccgg tggtggtggc gccctacaac ggcgggccgc cgcgcacgtg   16020
ccccaagatc aagcaggagg cggtctcttc gtgcacccac ttgggcgctg acccctct     16080 cagcaatggc caccggccgg ctgcacacga cttcccctg gggcggcagc tccccagcag   16140 gactacccg accctgggtc ttgaggaagt gctgagcagc agggactgtc accctgccct   16200
gccgcttcct cccggcttcc atccccaccc gggccaat tacccatcct tcctgcccga     16260
tcagatgcag ccgcaagtcc cgccgctcca ttaccaagag ctcatgccac ccggttcctg   16320
catgccagag gagcccaagc caaagagggg aagacgatcg tggccccgga aaaggaccgc   16380
cacccacact tgtgattacg cgggctgcgg caaaacctac acaaagagtt cccatctcaa   16440
ggcacacctg cgaacccaca caggtgagaa accttaccac tgtgactggg acggctgtgg   16500
atggaaattc gcccgctcag atgaactgac caggcactac cgtaaacaca cggggcaccg   16560
cccgttccag tgccaaaaat gcgaccgagc attttccagg tcggaccacc tcgccttaca   16620
catgaagagg catttttaag gcgcgccata acttcgtata gcatacatta tacgaagtta   16680
tctgcaggaa gactcttggg tttctgatag gcactgactc tctctgccta ttggtctatt   16740
ttcccaccct taggctgctg gtggtctacc cttggaccca gaggttcttt gagtcctttg   16800
gggatctgtc cactcctgat gctgttatgg gcaaccctaa ggtgaaggct catggcaaga   16860
aagtgctcgg tgcctttagt gatggcctgg ctcacctgga caacctcaag ggcacctttg   16920
ccacactgag tgagctgcac tgtgacaagc tgcacgtgga tcctgagaac ttcagggtga   16980
gtctatggga cccttgatgt tttcttccc cttcttttct atggttaagt tcatgtcata    17040
ggaaggggag aagtaacagg gtacagttta gaatgggaaa cagacgaatg attgcatcag   17100
tgtggaagtc tcaggatcgt tttagttct tttatttgct gttcataaca attgttttct    17160
tttgtttaat tcttgctttc ttttttttc ttctccgcaa tttttactat tatacttaat    17220
gccttaacat tgtgtataac aaaaggaaat atctctgaga tacattaagt aacttaaaaa   17280
aaaactttac acagtctgcc tagtacatta ctatttggaa tatatgtgtg cttatttgca   17340
tattcataat ctccctactt tattttcttt tattttaat tgatacataa tcattataca    17400
tatttatggg ttaaagtgta atgttttaat atgtgtacac atattgacca aatcagggta   17460
attttgcatt tgtaatttta aaaatgctt tcttctttta atatacttt tgtttatct      17520 tatttctaat actttcccta atctctttct ttcagggcaa taatgataca atgtatcatg   17580
cctctttgca ccattctaaa gaataacagt gataatttct gggttaaggc aatagcaata   17640
tttctgcata taaatatttc tgcatataaa ttgtaactga tgtaagaggt ttcatattgc   17700
taatagcagc tacaatccag ctaccattct gcttttattt tatggttggg ataaggctgg   17760
attattctga gtccaagcta ggccttttg ctaatcatgt tcatacctct tatcttcctc    17820
ccacagctcc tgggcaacgt gctggtctgt gtgctggccc atcactttgg caaagaattc   17880
accccaccag tgcaggctgc ctatcagaaa gtggtggctg gtgtggctaa tgccctggcc   17940
```

```
cacaagtatc actaagctcg ctttcttgct gtccaatttc tattaaaggt tcctttgttc   18000
cctaagtcca actactaaac tgggggatat tatgaagggc cttgagcatc tggattctgc   18060
ctaataaaaa acatttattt tcattgcaat gatgtattta aattatttct gaatatttta   18120
ctaaaagggg aatgtgggag gtcagtgcat ttaaaacata agaaatgaa gagctagttc    18180 aaaccttggg aaaatacact atatcttaaa ctccatgaaa gaaggtgagg ctgcaaacag   18240
ctaatgcaca ttggcaacag ccctgatgcc tatgccttat tcatccctca gaaaggatt   18300 caagtagagg cttgatttgg aggttaaagt tttgctatgc tgtattttac attacttatt   18360
gttttagctg tcctcatgaa tgtcttttca ctacccattt gcttatcctg catctctcag   18420
ccttgactcc actcagttct cttgcttaga gataccacct ttcccctgaa gtgttccttc   18480
catgttttac ggcgagatgg tttctcctcg cctggccact cagccttagt tgtctctgtt   18540
gtcttataga ggtctacttg aagaaggaaa acagggggc atggtttgac tgtcctgtga    18600
gcccttcttc cctgcctccc ccactcacag tgacccggaa tctgcagtgc tagtctcccg   18660
gaactatcac tctttcacag tctgctttgg aaggactggg cttagtatga aaagttagga   18720
ctgagaagaa tttgaaaggg ggcttttgt agcttgatat tcactactgt cttattaccc    18780
tatcataggc ccaccccaaa tggaagtccc attcttcctc aggatgttta agattagcat   18840
tcaggaagag atcagaggtc tgctggctcc cttatcatgt cccttatggt gcttctggct   18900
ctgcagttat tagcatagtg ttaccatcaa ccaccttaac ttcattttc ttattcaata    18960 cctaggtagg tagatgctag attctggaaa taaaatatga gtctcaagtg gtccttgtcc   19020
tctctcccag tcaaattctg aatctagttg gcaagattct gaaatcaagg catataatca   19080
gtaataagtg atgatagaag ggtatataga agaattttat tatatgagag ggtgaaacct   19140
aaaatgaaat gaaatcagac ccttgtctta caccataaac aaaaataaat ttgaatgggt   19200
taaagaatta aactaagacc taaaaccata aaaatttta aagaaatcaa agaagaaaa     19260 ttctaatatt catgttgcag ccgttttttg aatttgatat gagaagcaaa ggcaacaaaa   19320
ggaaaaataa agaagtgagg ctacatcaaa ctaaaaaatt tccacacaaa aaagaaaaca   19380
atgaacaaat gaaggtgaa ccatgaaatg gcatatttgc aaaccaaata tttcttaaat    19440
attttggtta atatccaaaa tatataagaa acacagatga ttcaataaca aacaaaaaat   19500
taaaaatagg aaaataaaaa aattaaaaag aagaaaatcc tgccatttat gcgagaattg   19560
atgaacctgg aggatgtaaa actaagaaaa ataagcctga cacaaaaaga caaatactac   19620
acaaccttgc tcatatgtga aacataaaaa agtcactctc atggaaacag acagtagagg   19680 tatggttttcc aggggttggg ggtgggagaa tcaggaaact attactcaaa gggtataaaa  19740
tttcagttat gtgggatgaa taaattctag atatctaatg tacagcatcg tgactgtagt   19800
taattgtact gtaagtatat ttaaaatttg caaagagagt agattttttt gttttttag    19860 atggagtttt gctcttgttg tccaggctgg agtgcaatgg caagatcttg gctcactgca   19920
acctccgcct cctgggttca agcaaatctc ctgcctcagc ctcccgagta gctgggatta   19980
caggcatgcg acaccatgcc cagctaattt tgtattttta gtagagacgg gtttctcca    20040 tgttggtcag gctgatccgc ctcctcggcc accaaagggc tgggattaca ggcgtgacca   20100
ccgggcctgg ccgagagtag atcttaaaag catttaccac aagaaaaagg taactatgtg   20160
agataatggg tatgttaatt agcttgattg tggtaatcat ttcacaaggt atacatatat   20220
taaaacatca tgttgtacac cttaaatata tacaattttt atttgtgaat gatacctcaa   20280
```

```
-continued taaagttgaa gaataataaa aaagaataga catcacatga attaaaaaac taaaaaataa  20340
aaaaatgcat cttgatgatt agaattgcat tcttgatttt tcagatacaa atatccattt  20400
gactgtttac tcttttccaa aacaatacaa taaattttag cactttatct tcattttccc  20460
cttcccaatc tataatttta tatatatata ttttagatat tttgtatagt tttactccct  20520
agattttcta gtgttattat taaatagtga agaaatgttt acacttatgt acaaaatgtt  20580
ttgcatgctt ttcttcattt ctaacattct ctctaagttt attctatttt ttcctgatta  20640
tccttaatat tatctctttc tgctggaaat atattgttac ttttggttta tctaaaaatg  20700
gcttcatttt cttcattcta aaatcatgtt aaattaatac cactcatgtg taagtaagat  20760
agtggaataa atagaaatcc aaaaactaaa tctcacaaaa tataataatg tgatatataa  20820
aaatatagct tttaaattta gcttggaaat aaaaaacaaa cagtaattga acaactatac  20880
tttttgaaaa gagtaaagtg aaatgcttaa ctgcatatac cacaatcgat tacacaatta  20940
ggtgtgaagg taaaattcag tcacgaaaaa actagaataa aaatatggga agacatgtat  21000
ataatcttag agataacagt gttatttaat tatcaactag ttctagagcg gccgccaccg  21060
cggtggagct ccagcttttg ttcccttta g tgagggttaa tttcgagctt ggcgtaatca  21120
tggtcatagc tgtttcctgt gtgaaattgt tatccgctca caattccaca caacatacga  21180
gccggaagca taaagtgtaa agcctggggt gcctaatgag tgagctaact cacattaatt  21240
gcgttgcgct cactgcccgc tttccagtcg ggaaacctgt cgtgccagct gcattaatga  21300
atcggccaac gcgcggggag aggcggtttg cgtattgggc gctcttccgc ttcctcgctc  21360
actgactcgc tgcgctcggt cgttcggctg cggcgagcgg tatcagctca ctcaaaggcg  21420
gtaatacggt tatccacaga atcagggga t aacgcaggaa agaacatgtg agcaaaaggc  21480
cagcaaaagg ccaggaaccg taaaaaggcc gcgttgctgg cgtttttcca taggctccgc  21540
ccccctgacg agcatcacaa aaatcgacgc tcaagtcaga ggtggcgaaa cccgacagga  21600
ctataaagat accaggcgtt tccccctgga agctccctcg tgcgctctcc tgttccgacc  21660
ctgccgctta ccggatacct gtccgccttt ctccctt                           21697
```